(12) United States Patent
Murooka et al.

(10) Patent No.: US 10,724,892 B2
(45) Date of Patent: Jul. 28, 2020

(54) MEASUREMENT SYSTEM, MEASUREMENT METHOD, AND MEASUREMENT PROGRAM

(71) Applicant: FUJIFILM Corporation, Tokyo (JP)

(72) Inventors: Takashi Murooka, Ashigarakami-gun (JP); Yi Hu, Ashigarakami-gun (JP); Yasutomo Goto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 429 days.

(21) Appl. No.: 15/697,671

(22) Filed: Sep. 7, 2017

(65) Prior Publication Data

US 2018/0058902 A1 Mar. 1, 2018

Related U.S. Application Data

(63) Continuation of application No. PCT/JP2016/055382, filed on Feb. 24, 2016.

(30) Foreign Application Priority Data

Mar. 10, 2015 (JP) ................. 2015-047623

(51) Int. Cl.
*G01N 21/49* (2006.01)
*G01F 23/292* (2006.01)
(Continued)

(52) U.S. Cl.
CPC .......... *G01F 23/292* (2013.01); *A61M 37/00* (2013.01); *G01B 11/00* (2013.01); *G01B 11/24* (2013.01);
(Continued)

(58) Field of Classification Search
CPC ........ A61M 37/00; G01B 11/00; G01B 11/24; G01F 22/00; G01F 23/292
(Continued)

(56) References Cited

U.S. PATENT DOCUMENTS 5,959,738 A 9/1999 Hafeman et al.
7,323,705 B2 1/2008 Haga et al.
(Continued)

FOREIGN PATENT DOCUMENTS

JP 58-100713 A 6/1983
JP H04-328449 A 11/1992
(Continued)

OTHER PUBLICATIONS

International Preliminary Report on Patentability dated Sep. 12, 2017, in counterpart International Application No. PCT/JP2016/055382.
(Continued)

*Primary Examiner* — Georgia Y Epps
(74) *Attorney, Agent, or Firm* — Sughrue Mion, PLLC

(57) ABSTRACT

A measurement system that measures an amount of a drug solution in each needle-shaped recess of a mold in which a plurality of needle-shaped recesses are formed, or an amount of a drug after drying the drug solution, includes: a first detection unit that detects position information regarding each needle-shaped recess in a state where the drug solution does not fill the needle-shaped recess; a first measurement unit that measures a shape of the needle-shaped recess; a second detection unit that detects position information regarding a surface of the drug solution or the drug; a second measurement unit that measures a shape of the surface of the drug solution or the drug; and a calculation unit that calculates a volume of the drug solution or the drug based on the shape of the needle-shaped recess and the shape of the surface of the drug solution or the drug.

9 Claims, 39 Drawing Sheets

(51) Int. Cl.
*G01B 11/00* (2006.01)
*A61M 37/00* (2006.01)
*G01F 22/00* (2006.01)
*G01B 11/24* (2006.01)

(52) U.S. Cl.
CPC ......... *G01F 22/00* (2013.01); *A61M 37/0015* (2013.01); *A61M 2037/0023* (2013.01); *A61M 2037/0053* (2013.01); *A61M 2205/3306* (2013.01); *A61M 2205/3382* (2013.01); *A61M 2207/10* (2013.01)

(58) Field of Classification Search
USPC ........................................................ 250/577
See application file for complete search history.

(56) References Cited

U.S. PATENT DOCUMENTS

| | | | |
|---|---|---|---|
| 2008/0304082 | A1 | 12/2008 | Gotz et al. |
| 2010/0182136 | A1 | 7/2010 | Pryor |
| 2012/0051660 | A1 | 3/2012 | Lee et al. |
| 2014/0313524 | A1 | 10/2014 | Banyay et al. |
| 2017/0205270 | A1* | 7/2017 | Luedemann .......... G01F 23/292 |

FOREIGN PATENT DOCUMENTS

| | | |
|---|---|---|
| JP | H11-218437 A | 8/1999 |
| JP | 2000-283734 A | 10/2000 |
| JP | 2001-133309 A | 5/2001 |
| JP | 2002-098633 A | 4/2002 |
| JP | 2008-224673 A | 9/2008 |
| JP | 2011-224332 A | 11/2011 |
| JP | 2012-254952 A | 12/2012 |
| JP | 2013-162982 A | 8/2013 |
| JP | 2014-174047 A | 9/2014 |
| JP | 2014-531578 A | 11/2014 |
| WO | 2015/012112 A1 | 1/2015 |
| WO | 2016/143515 A1 | 9/2016 |

OTHER PUBLICATIONS

Translation of Written Opinion of the International Searching Authority dated May 24, 2016, in counterpart International Application No. PCT/JP2016/055382.
International Search Report dated May 24, 2016, issued by the International Searching Authority in corresponding application No. PCT/JP2016/055382.
Communication dated Jun. 7, 2018 from the Japanese Patent Office in counterpart Application No. 2015-047623.
Communication dated Jan. 31, 2018, from Japanese Patent Office in counterpart application No. 2015-047623.
Communication dated Apr. 10, 2018 from the European Patent Office in counterpart application No. 16761486.6.
Berkovic et al., "Optical methods for distance and displacement measurements", Advances in Optics and Photonics, vol. 4, Sep. 12, 2012, pp. 441-471.
"Bioassay", Wikipedia, Jan. 27, 2015, Retrieved from the internet on Feb. 9, 2018, URL: https://en.wikipedia.org/w/index.php?title=Bioassay&oldid=644423738. (4 pages total).
Communication dated Mar. 10, 2020, from the European Patent Office in Application No. 16761486.6.

* cited by examiner

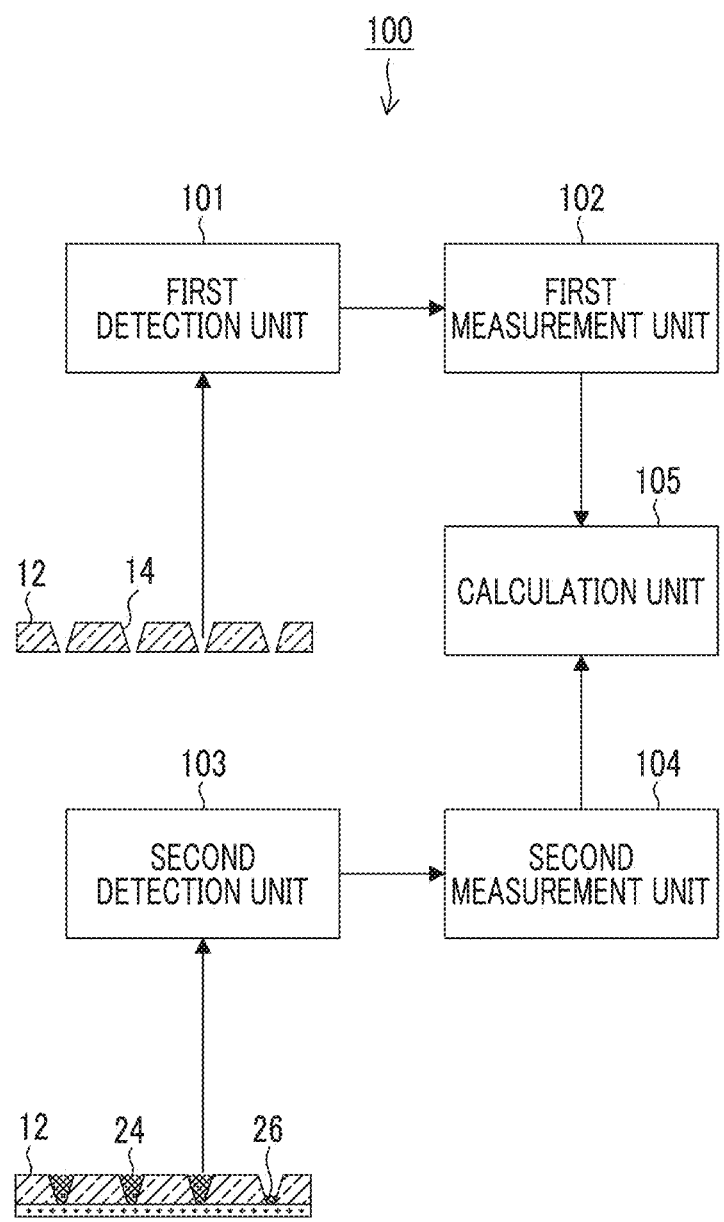

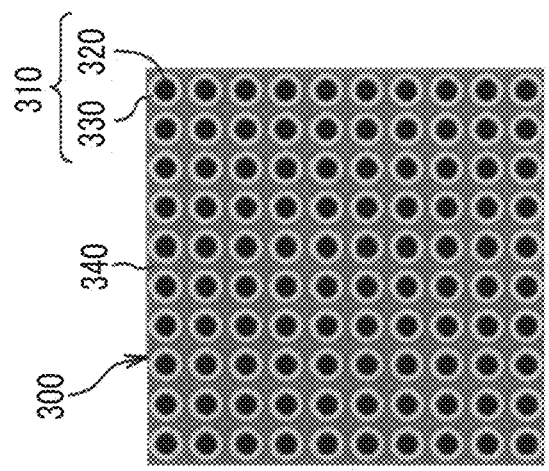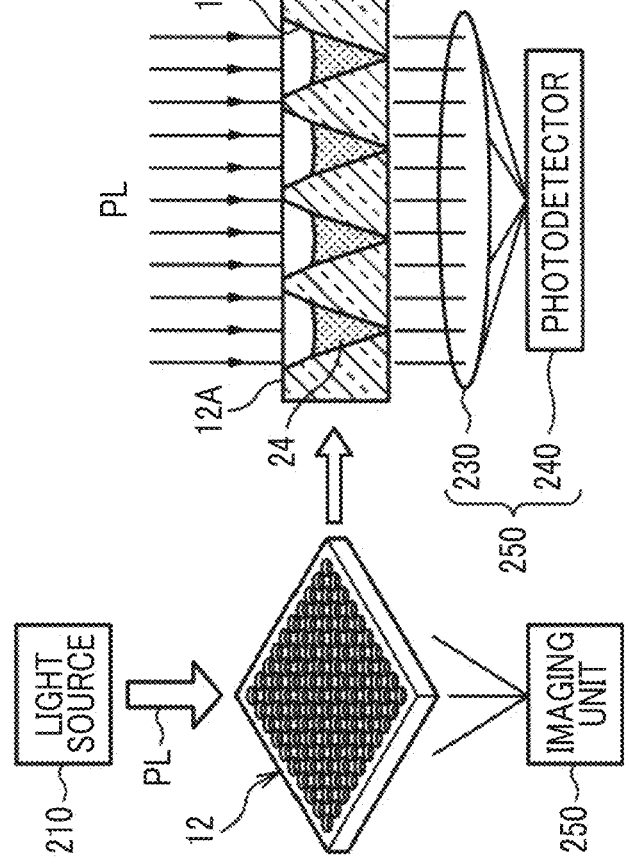

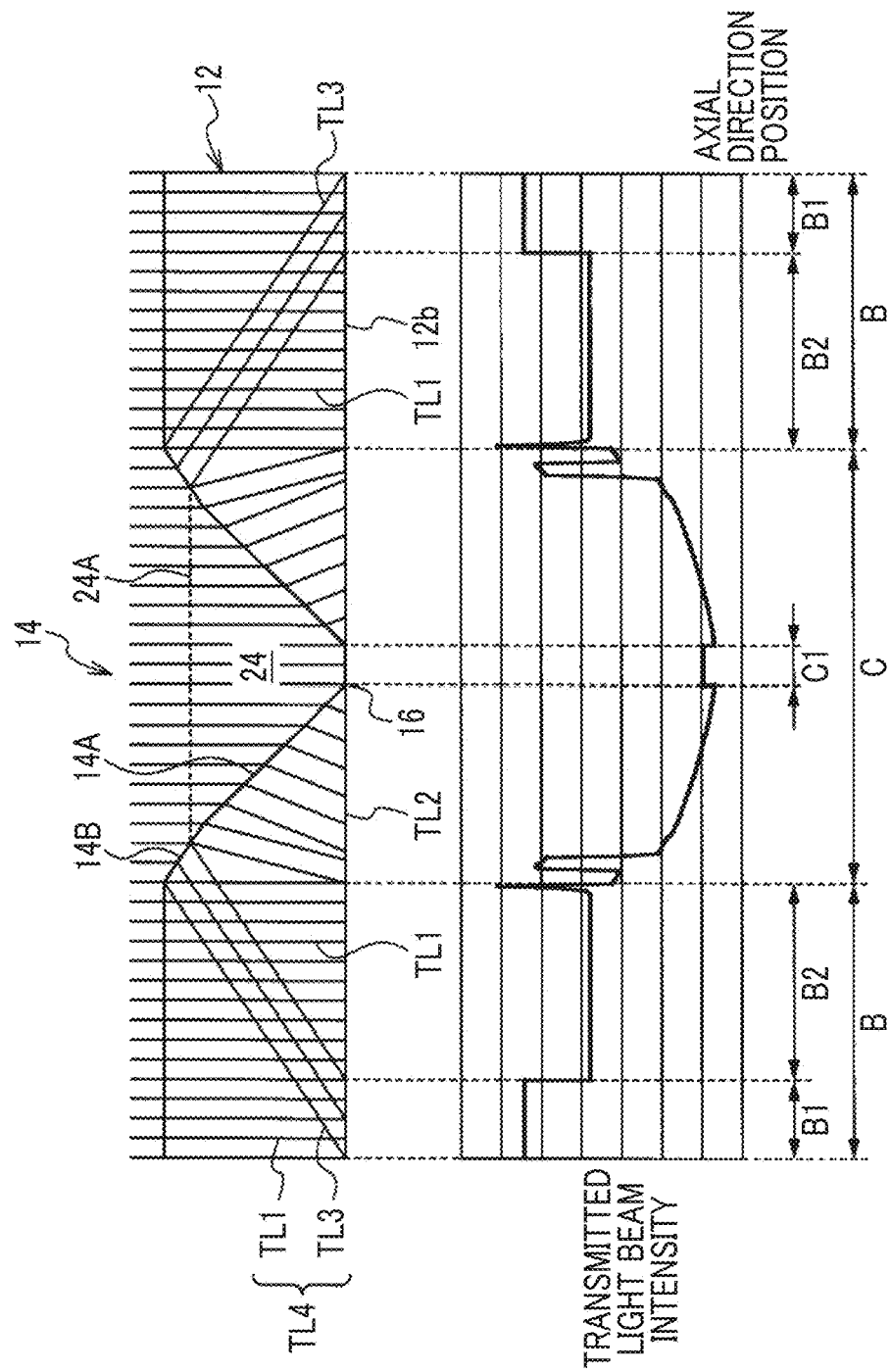

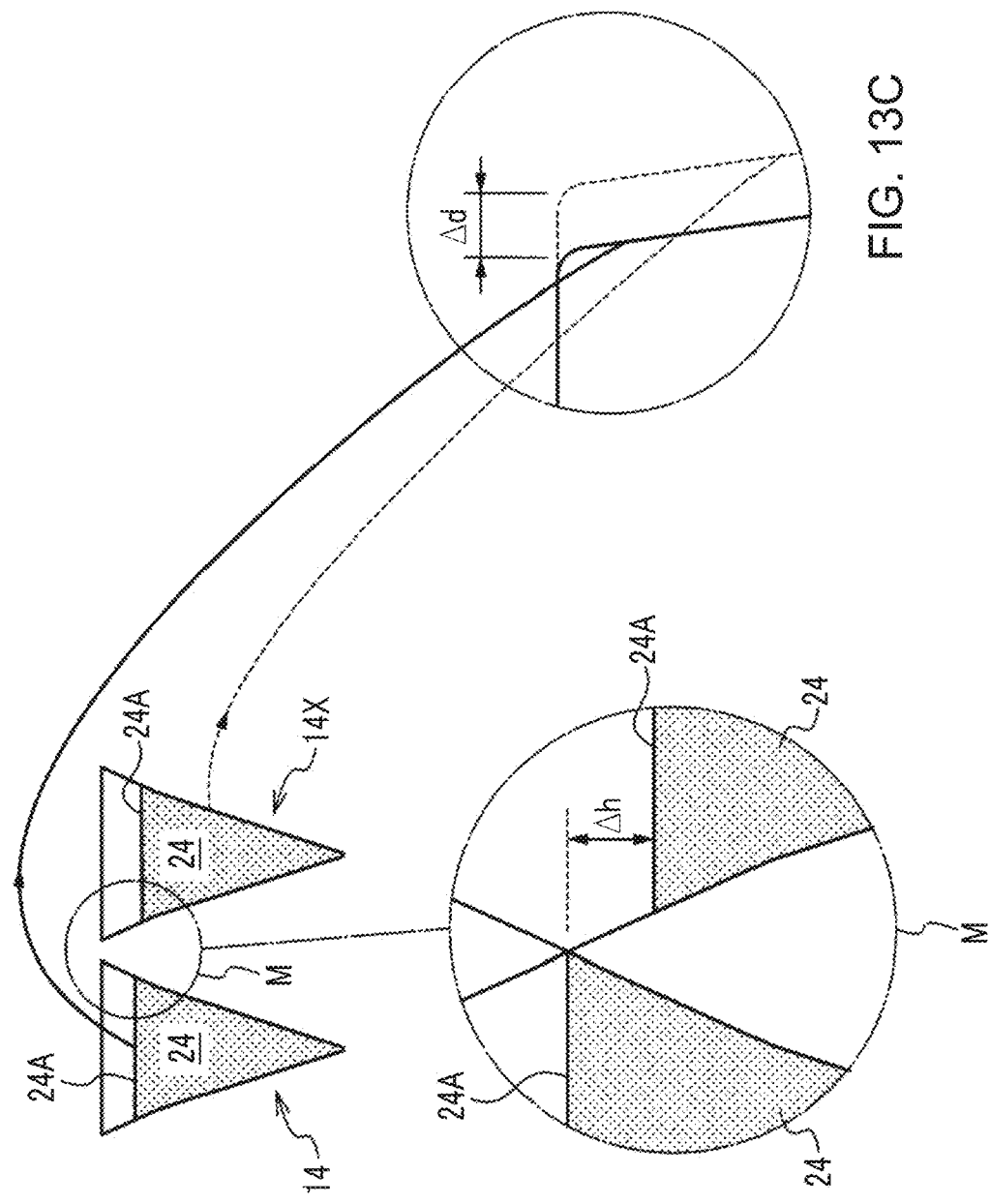

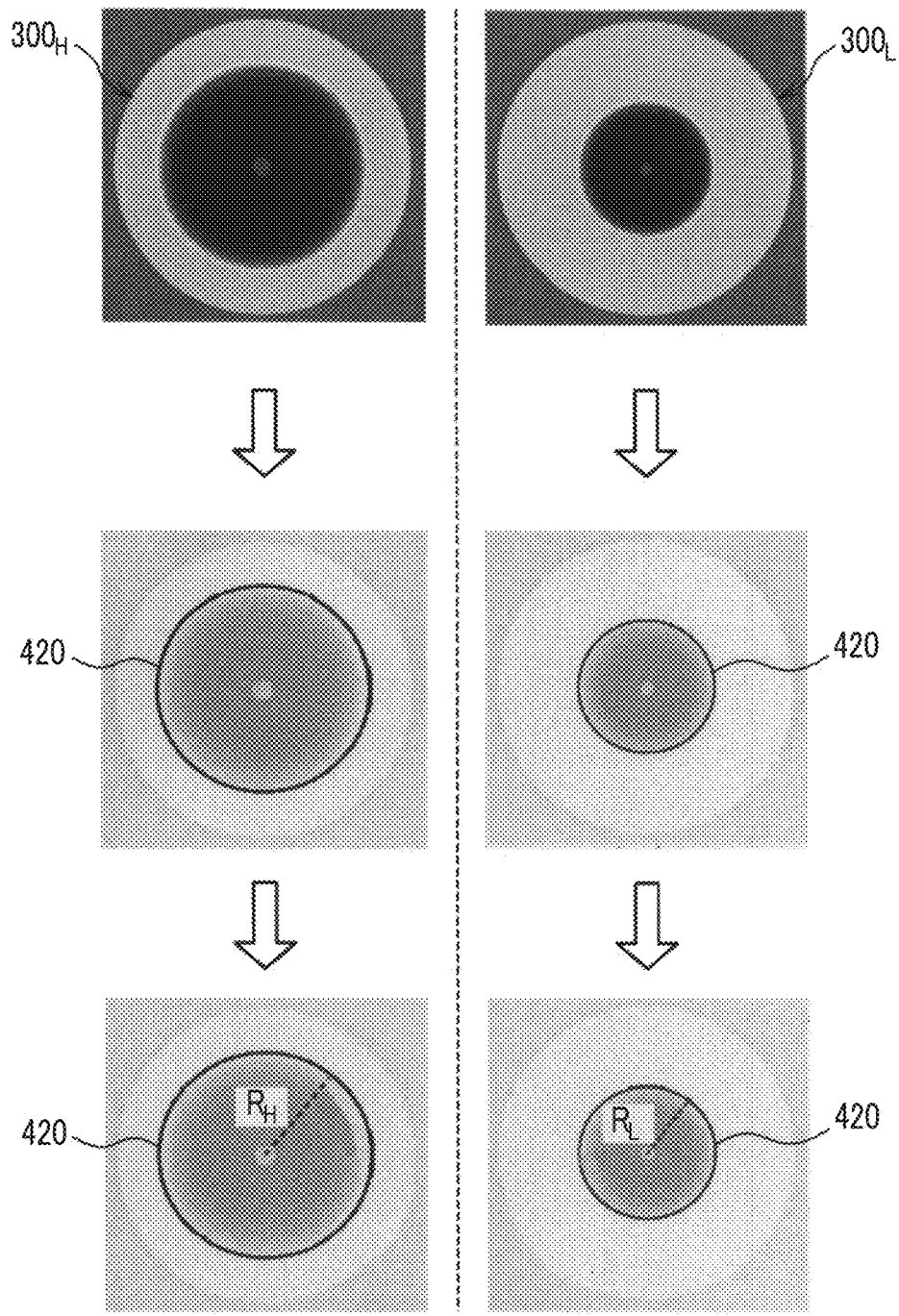

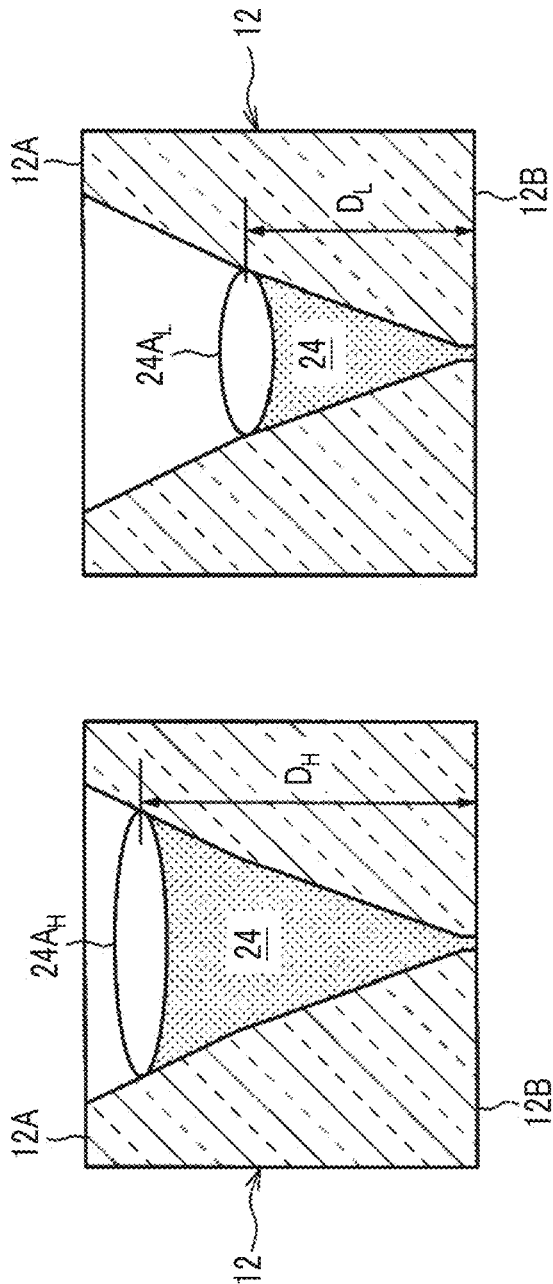

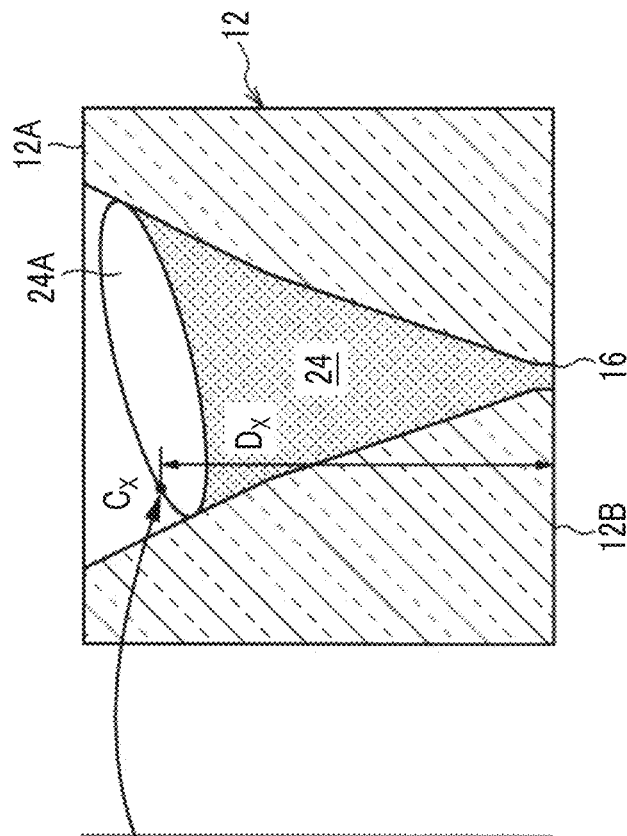
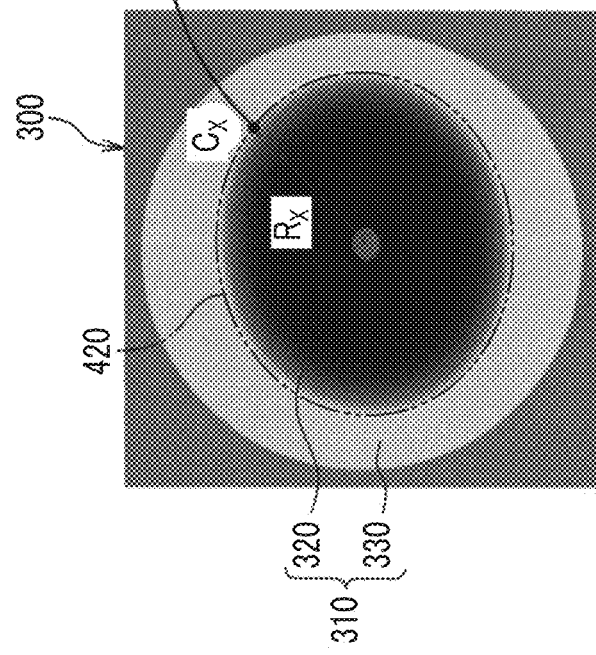
FIG. 19A
FIG. 19B

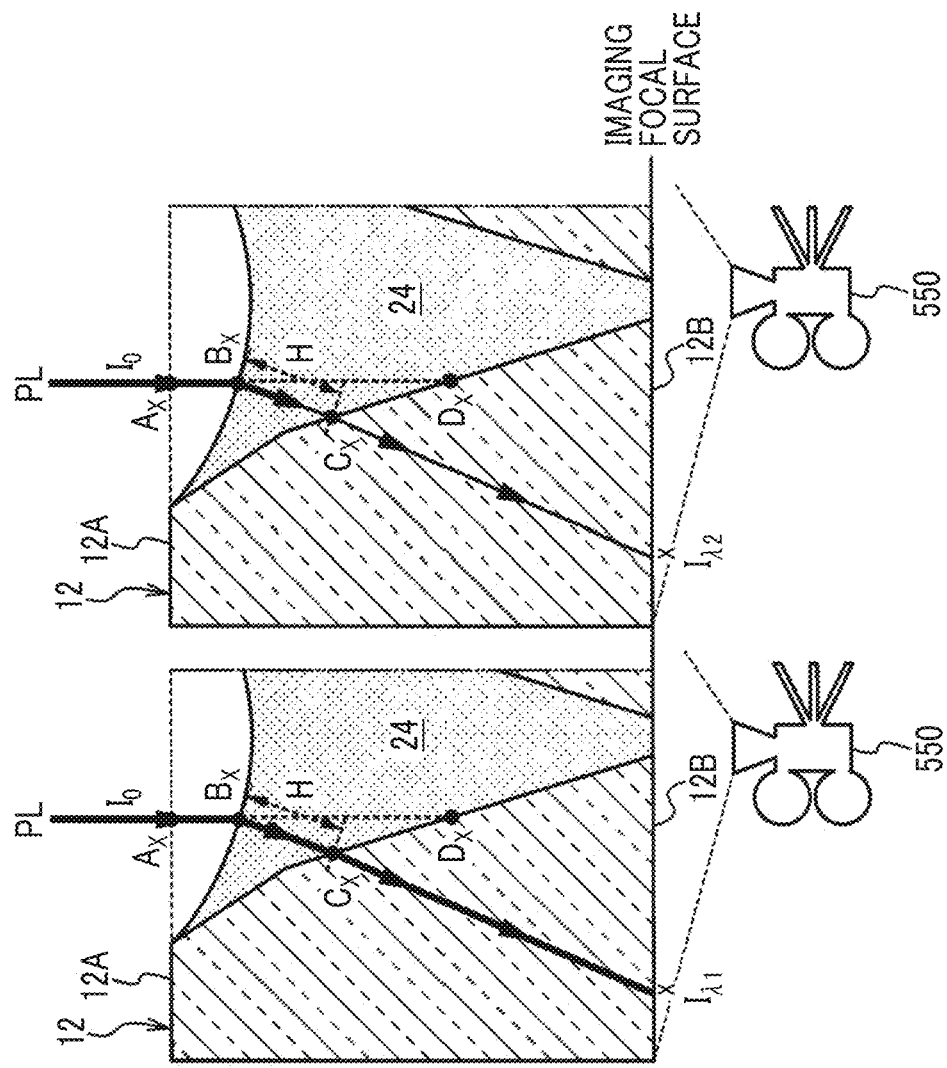

MEASUREMENT SYSTEM, MEASUREMENT METHOD, AND MEASUREMENT PROGRAM

CROSS-REFERENCE TO RELATED APPLICATIONS

This application is a Continuation of PCT International Application No. PCT/JP2016/055382 filed on Feb. 24, 2016, which claims priorities under 35 U.S.C. § 119(a) to Japanese Patent Application No. 2015-047623 filed on Mar. 10, 2015. Each of the above applications is hereby expressly incorporated by reference, in their entirety, into the present application.

BACKGROUND OF THE INVENTION

1. Field of the Invention

The present invention relates to a measurement system, a measurement method, and a measurement program, and particularly, to a technique that measures the amount of a drug solution that fills each needle-shaped recess of a sheet-shaped mold in which a plurality of needle-shaped recesses, the needle-shaped recess being an inverted type of a micro-needle, are formed or the amount of a drug after the filled drug solution is dried.

2. Description of the Related Art

In recent years, as a new agent mold capable of dosing a drug such as insulin, vaccines, or human growth hormone (hGH) into the skin without causing pains, a micro-needle array (hereinafter, simply referred to as an "MNA") is known. The MNA is a device that contains a drug, in which biodegradable micro-needles (also referred to as fine needles) are arranged in an array shape. By attaching the MNA to the skin, each micro-needle pierces the skin, and thus, the micro-needles are absorbed into the skin. Thus, it is possible to dose the drug contained in each micro-needle into the skin.

As a method for manufacturing such an MNA, a method for filling a solution drug (a drug solution obtained by dissolving a drug or the like into water) in each needle-shaped recess of a mold having multiple needle-shaped recesses, the needle-shaped recess being an inverted type of a micro-needle, drying the solution drug to form an MNA, and then, separating the MNA from the mold (JP2013-162982A). In manufacturing the MNA, it is necessary to strictly manage the amount of a drug dosed in the skin by the MNA.

As a method for measuring the amount of a drug contained in the MNA, for example, the method for measuring the weight of a mold before filling of the drug and the amount of the mold after filling of the drug using a highly accurate electronic balance, and then calculating a weight difference before filling and after filling to measure the weight of the drug is known.

On the other hand, JP2011-224332A discloses a method for dissolving an MNA into the water to measure the amount of a drug contained in the MNA.

Further, JP2012-254952A discloses a method for observing a two-layer micro-needle including a first portion that contains a drug and a second portion that does not contain a drug using a video microscope, and measuring the length of the first portion colored with blue from a tip thereof.

SUMMARY OF THE INVENTION

However, in a case where measurement of the weight of a drug is performed using the above-described electronic balance with high accuracy, since the weight of the drug is small compared with the weight of the mold, for example, since the weight of the drug is one several hundredths of the weight of the mold, it is not possible to measure the weight of the drug with high accuracy on the basis of a weight difference between the mold before filling of the drug and the mold after filling of the drug.

Further, in the method disclosed in JP2011-224332A, since it is necessary to perform destructive measurement in which the MNA is dissolved into water, there is a problem in that the manufactured MNA is destroyed.

In addition, if the shape of a two-layer micro-needle including a first portion that contains a drug and a second portion that does not contain a drug is already known, as disclosed in JP2012-254952A, it is possible to calculate the volume of the first portion by measuring the length of the first portion colored with blue from the tip thereof. Ideally, it is desirable that the shape of the needle-shaped recess of the mold has a reversed shape of an MNA. However, in the reversed shape of the MNA, needle-shaped recesses of an actual mold have irregularities. In a case where the volume is calculated from the length of the first portion colored with blue from the tip thereof, there are also irregularities in shapes of micro-needles, and thus, there is a concern that an error occurs in the volume of the calculated drug solution.

The invention has been made in consideration of such a problem, an object of the invention is to provide a measurement system, a measurement method, and a measurement program capable of measuring the amount of a drug solution that fills each needle-shaped recess of a mold or the amount of a drug after the filled drug solution is dried in a non-destructive manner with high accuracy before a micro-needle array is separated from the mold.

According to a first aspect of the invention, there is provided a measurement system that measures an amount of a drug solution that fills each needle-shaped recess of a mold in which a plurality of needle-shaped recesses are formed and which includes a first surface and a second surface, the needle-shaped recess being an inverted type of a micro-needle, or am amount of a drug after the filled drug solution is dried, the system comprising: a first detection unit that detects position information regarding each needle-shaped recess of the mold in a state where the drug solution does not fill the needle-shaped recess; a first measurement unit that measures the shape of the needle-shaped recess on the basis of a detection result of the first detection unit; a second detection unit that detects position information regarding the drug solution that fills the needle-shaped recess or the drug after the filled drug solution is dried; a second measurement unit that measures the shape of the drug solution or the drug on the basis of a detection result of the second detection unit; and a calculation unit that calculates the volume of the drug solution that fills the needle-shaped recess or the drug after the filled drug solution is dried on the basis of the shape of the needle-shaped recess measured by the first measurement unit and the shape of the drug solution or the drug measured by the second measurement unit.

Preferably, the first detection unit is a confocal microscope that includes at least a confocal optical system and a photodetector.

Preferably, the first detection unit includes at least a triangulation type displacement meter.

Preferably, the second detection unit is a confocal microscope that includes a confocal optical system and a photodetector.

Preferably, the second detection unit includes at least a triangulation type displacement meter.

Preferably, the second detection unit includes a light source that allows parallel light beams to be vertically incident to the first surface of the mold on a side where the drug solution is filled, and a photodetector that images transmitted light beams of the parallel light beams emitted from the second surface on a side opposite to the first surface, and the transmitted light beams include a first transmitted light beam that goes straight inside the mold and is output from a first region of the second surface, a second transmitted light beam that is incident to a first wall surface portion in the mold, is refracted by the first wall surface portion, and is output from a second region, corresponding to the needle-shaped recess, of the second surface, and a third transmitted light beam that is incident to a second wall surface in the mold, is refracted by the second wall surface portion at a refractive angle larger than that of the first transmitted light beam, and is output from a part of the first region.

Preferably, the second detection unit includes a light source that allows parallel light beams having a first wavelength band and a second wavelength band to be vertically incident to the second surface, a photodetector that images a first transmitted light beam of the first wavelength band and a second transmitted light beam of the second wavelength band output from the first surface on a side opposite to the second surface, and an image analysis unit that analyzes images of the first transmitted light beam and the second transmitted light beam, and the second measurement unit includes a distance measurement unit that measures a distance at each position in the surface of the drug solution on the basis of a detection result of the image analysis unit.

According to a second aspect of the invention, there is provided a measurement method for measuring an amount of a drug solution that fills each needle-shaped recess of a mold in which a plurality of needle-shaped recesses are formed, the needle-shaped recess being an inverted type of a micro-needle, or an amount of a drug after the filled drug solution is dried, the method comprising: a first detection step of detecting position information regarding each needle-shaped recess of the mold in a state where the drug solution does not fill the needle-shaped recess; a first measurement step of measuring the shape of the needle-shaped recess on the basis of a detection result in the first detection step; a second detection step of detecting position information regarding a surface of the drug solution that fills the needle-shaped recess or the drug after the filled drug solution is dried; a second measurement step of measuring the shape of the surface of the drug solution or the surface of the drug on the basis of a detection result in the second detection step; and a calculation step of calculating the volume of the drug solution that fills the needle-shaped recess or the drug after the filled drug solution is dried on the basis of the shape of the needle-shaped recess measured in the first measurement step and the shape of the surface of the drug solution or the drug measured in the second measurement step.

According to a third aspect of the invention, there is provided a measurement program for measuring an amount of a drug solution that fills each needle-shaped recess of a mold in which a plurality of needle-shaped recesses are formed, the needle-shaped recess being an inverted type of a micro-needle, or an amount of a drug after the filled drug solution is dried, the program causing a computer to execute: a first detection step of detecting position information regarding each needle-shaped recess of the mold in a state where the drug solution does not fill the needle-shaped recess; a first measurement step of measuring the shape of the needle-shaped recess on the basis of a detection result in the first detection step; a second detection step of detecting position information regarding a surface of the drug solution that fills the needle-shaped recess or the drug after the filled drug solution is dried; a second measurement step of measuring the shape of the surface of the drug solution or the surface of the drug on the basis of a detection result in the second detection step; and a calculation step of calculating the volume of the drug solution that fills the needle-shaped recess or the drug after the filled drug solution is dried on the basis of the shape of the needle-shaped recess measured in the first measurement step and the shape of the surface of the drug solution or the drug measured in the second measurement step. A computer-readable non-transitory tangible recording medium on which the measurement program is recorded is also included in an aspect of the invention.

According to the invention, it is possible to measure the amount of a drug solution that fills each needle-shaped recess of a mold or the amount of a drug after the filled drug solution is dried in a non-destructive manner with high accuracy before a micro-needle array is separated from the mold.

BRIEF DESCRIPTION OF THE DRAWINGS

FIG. 5 is a diagram showing a configuration of a measurement system.

FIGS. 10A to 10C are diagrams illustrating acquisition of a transmitted light beam pattern image in a measurement apparatus.

FIG. 12A is a cross-sectional view of needle-shaped recesses of a mold, and FIG. 12B is a graph illustrating intensity distributions (transmitted light beam intensity distributions) of transmitted light beams of parallel light beams which pass through the mold.

FIG. 13A is a cross-sectional view of needle-shaped recesses in which volumes of drug solutions are different from each other, FIG. 13B is an enlarged view of a region M in FIG. 13A, and FIG. 13C is an enlarged view in which a transmitted light beam intensity of a boundary portion on the left side in the figure between partial regions B1 and B2 shown in FIG. 12B is enlarged.

FIG. 17A is a diagram illustrating the measurement of the radius of a surface feature line of the first surface, and FIG. 17B is a diagram illustrating measurement of the radius of a surface feature line of the second surface.

FIGS. 18A and 18B are diagrams illustrating detection of a surface height of the first surface and detection of a surface height of the second surface.

FIG. 19A is a diagram illustrating a surface feature line radius detection process in a radius detection unit, and FIG. 19B is a diagram illustrating a surface height detection process in a surface height detection unit.

FIGS. 29A and 29B are diagrams in a case where a position relationship between a light source and an imaging unit is reversed to the present embodiment, in which FIG. 29A is a diagram illustrating an optical path in a comparative example in which the measurement light beam of the wavelength band $\lambda 1$ passes through a drug solution in a needle-shaped recess of the mold, and FIG. 29B is a diagram illustrating an optical path in a comparative example in which the measurement light beam of the wavelength band $\lambda 2$ passes through a drug solution in a needle-shaped recess of the mold.

DESCRIPTION OF THE PREFERRED EMBODIMENTS

Hereinafter, preferred embodiments of the invention will be described with reference to the accompanying drawings. The invention will be described based on the following preferred embodiments. Modifications may be made using various methods and embodiments other than the present embodiments may be used in a range without departing from the scope of the invention.

Here, in the figures, portions indicated by the same reference sign represent the same element having the same function. Further, in this specification, in a case where a numerical value range is expressed using the form of "A to B", it is assumed that numerical values of an upper limit and a lower limit indicated by "A to B" are included in the numerical value range.

Hereinafter, preferred embodiments of a measurement system, a measurement method, and a measurement program according to the invention will be described with reference to the accompanying drawings.

First, a method for manufacturing a percutaneous absorption sheet (an MNA sheet) including a first polymer layer that contains a drug and a second polymer layer that does not contain a drug in a micro-needle array (MNA) will be described.

Figure 1:
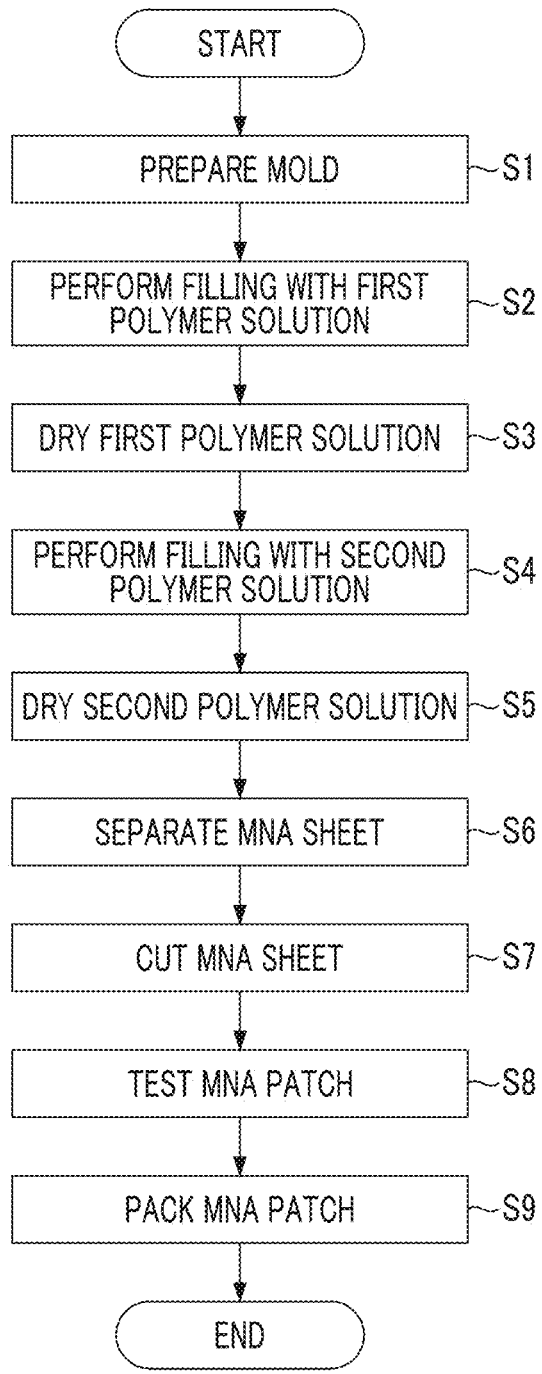
FIG. 1 is a flowchart showing a method for manufacturing an MNA sheet.

FIG. 1 is a flowchart of a method for manufacturing an MNA sheet. As shown in FIG. 1, the method for manufacturing the MNA sheet includes a process of preparing a mold having needle-shaped recesses (step S1), a process of filling the needle-shaped recesses with a first polymer solution (hereinafter, may be simply referred to as a "drug solution") that contains a drug (step S2), a process of drying the first polymer solution to obtain a drug (step S3), a process of filling a second polymer solution that does not contain a drug on the dried first polymer solution (step S4), a process of drying a second polymer solution (step S5), a process of separating the MNA sheet from the mold (step S6), a step of cutting the MNA sheet into an MNA patch (step S7), a step of testing the MNA patch (step S8), and a step of packing the MNA patch (step S9).

Figure 2A:
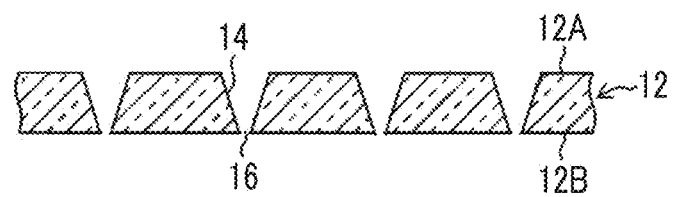
FIGS. 2A to 2D are diagrams showing a part of a procedure of the method for manufacturing the MNA sheet.

As shown in FIG. 2A, a mold 12 on which a plurality of needle-shaped recesses 14 which a reverse mold of the MNA mold is prepared. The needle-shaped recess 14 has, for example, a conical shape that is gradually tapered from a first surface 12A of the mold 12 to a second surface 12B opposite to the first surface 12A. On the second surface 12B of the mold 12 which corresponds to a tapered tip of the needle-shaped recess 14, a communication hole 16 that is continuous to each needle-shaped recess 14 is formed. The size of the communication hole 16 is 1 μm to 100 μm in diameter, for example.

The communication hole 16 is covered with a gas transmission sheet 18 formed of a material that transmits a gas but does not transmit a liquid. A suction force may be given to the needle-shaped recess 14 through the gas transmission sheet 18 by a suction device (not shown).

Figure 2B:
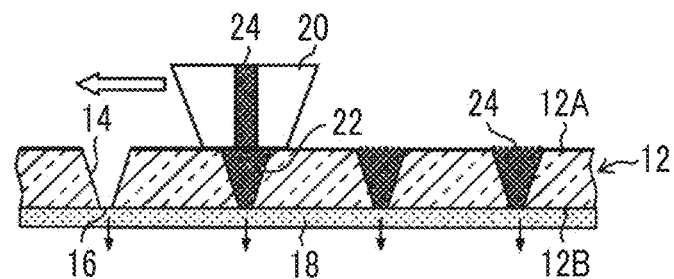

Subsequently, as shown in FIG. 2B, a drug solution 24 is supplied to the needle-shaped recess 14 from a discharge port 22 of a nozzle 20 while moving the nozzle 20 along the first surface 12A of the mold 12.

The drug solution 24 is scratched by the movement of the nozzle 20. The communication hole 16 is covered with the gas transmission sheet 18 formed of a material that transmits a gas but does not transmit a liquid. A suction force may be given to the needle-shaped recess 14 through the gas transmission sheet 18 through the communication hole 16 by a suction device (not shown). By giving the suction force to the needle-shaped recess 14 through the gas transmission sheet 18, it is possible to fill the inside of the needle-shaped recess 14 with the drug solution 24 by the suction force.

Figure 2C:
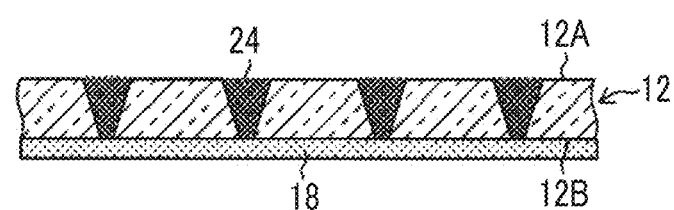

FIG. 2C shows a status immediately after the drug solution 24 fills the needle-shaped recess 14 of the mold 12.

Figure 2D:
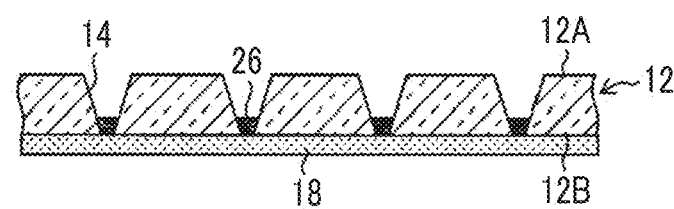

Then, as shown in FIG. 2D, by drying the drug solution 24 that fills the needle-shaped recess 14, a dried drug (a first polymer layer) 26 is formed in a tip portion of the needle-shaped recess 14.

Figure 3A:
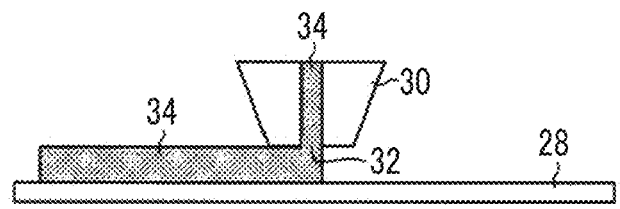
FIGS. 3A to 3D are diagrams showing a part of the procedure of the method for manufacturing the MNA sheet.

Subsequently, as shown in FIG. 3A, a second polymer solution (hereinafter, may be simply referred to as a "base solution") 34 that does not contain a drug from a discharge port 32 of a nozzle 30 is coated on a support 28 made of a resin.

Figure 3B:
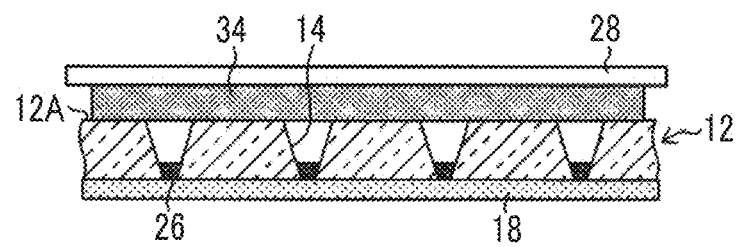

Then, as shown in FIG. 3B, the base solution 34 coated on the support 28 is overlaid on the first surface 12A of the mold 12 in which the drug 26 is formed inside the needle-shaped recess 14.

Figure 3C:
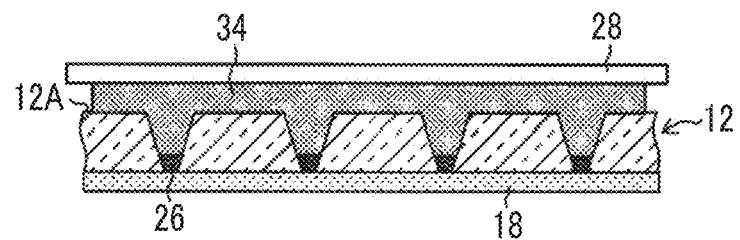

Then, as shown in FIG. 3C, the base solution 34 coated on the support 28 is provided on the drug 26 in the needle-shaped recess 14.

Figure 3D:
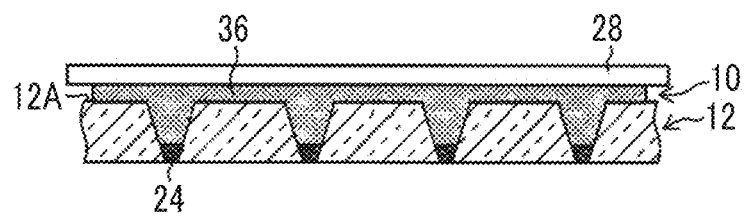

Then, as shown in FIG. 3D, by drying the base solution 34 that fills the needle-shaped recess 14, a dried base material (a second polymer layer) 36 is formed on the drug solution 24. Thus, an MNA sheet 10 is manufactured.

Figure 4A:
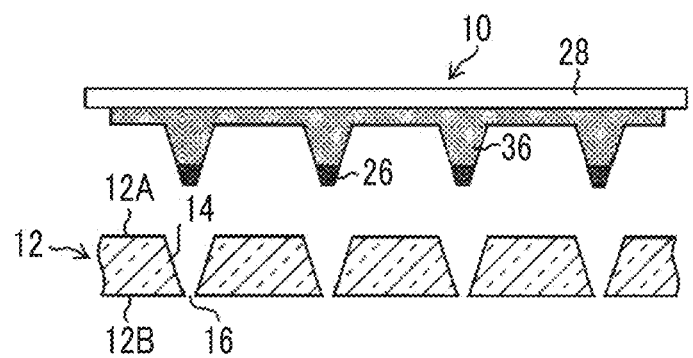
FIGS. 4A to 4D are diagrams showing a part of the procedure of the method for manufacturing the MNA sheet.

Subsequently, as shown in FIG. 4A, the MNA sheet 10 that is configured by the drug 26 (the first polymer layer), the base 36 (the second polymer layer), and the support 28 is separated from the mold 12.

Figure 4B:
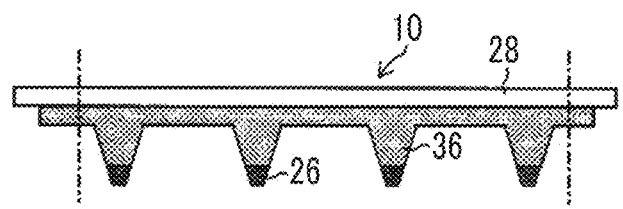

Then, as shown in FIG. 4B, the MNA sheet 10 is cut and divided into an MNA patch 10A which is a product unit.

Figure 4C:
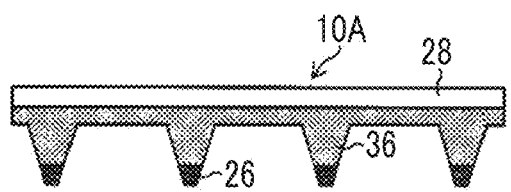

Then, as shown in FIG. 4C, the cut MNA patch 10A is set in a test device (not shown), and a quality test or the like is performed with respect to the MNA patch 10A.

Figure 4D:
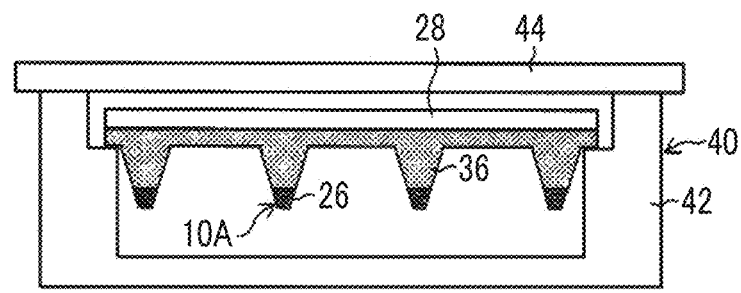

Finally, as shown in FIG. 4D, the MNA patch 10A that passes the quality test or the like is packed in a packaging container 40. In this state, storage, shipping, or the like is performed. The packaging container 40 includes a box-like body 42 formed by a bottom surface and side surfaces, for example, and a cover that covers an opening of an upper surface of the box-like body 42.

In the MNA sheet 10 (MNA sheet 10A), in order to manage the amount of a drug to be administered into the skin, it is necessary to correctly measure the amount of a drug that fills a needle-shaped recess of a mold.

The invention is configured to acquire shape data of the needle-shaped recess 14 of the mold 12 in a state where the drug solution 24 does not fill the needle-shaped recess 14, to acquire shape data of the drug solution 24 or the drug 26 in a state where the drug solution 24 or the drug 26 fills the needle-shaped recess 14 of the mold 12, and to measure the amount of the drug solution 24 that fills the needle-shaped recess or the amount of the drug 26 after the filled drug solution 24 is dried from the shape data of the needle-shaped recess and the shape data of the drug solution or the drug.

[Measurement System]

FIG. 5 is a diagram showing a configuration of a measurement system according to the invention. A measurement system 100 includes a first detection unit 101 and a first measurement unit 102 that acquire shape data of the needle-shaped recess 14 of the mold 12, a second detection unit 103 and a second measurement unit 104 that acquire shape data of the drug solution 24 or the drug 26 of the mold 12, and a calculation unit 105 that calculates the volume of the drug solution 24 or the drug 26 using the shape of the needle-shaped recess 14 and the shape of the surface of the drug solution 24 or the drug 26.

First, acquisition of the shape data of the needle-shaped recess 14 will be described. In this embodiment, the first detection unit 101 detects position information regarding the needle-shaped recess 14 of the mold 12 in a state where the drug solution 24 does not fill the needle-shaped recess 14, and for example, a method using a confocal optical system may be applied thereto. The confocal optical system is an optical system in which a pinhole is disposed on an imaging surface.

Figure 6:
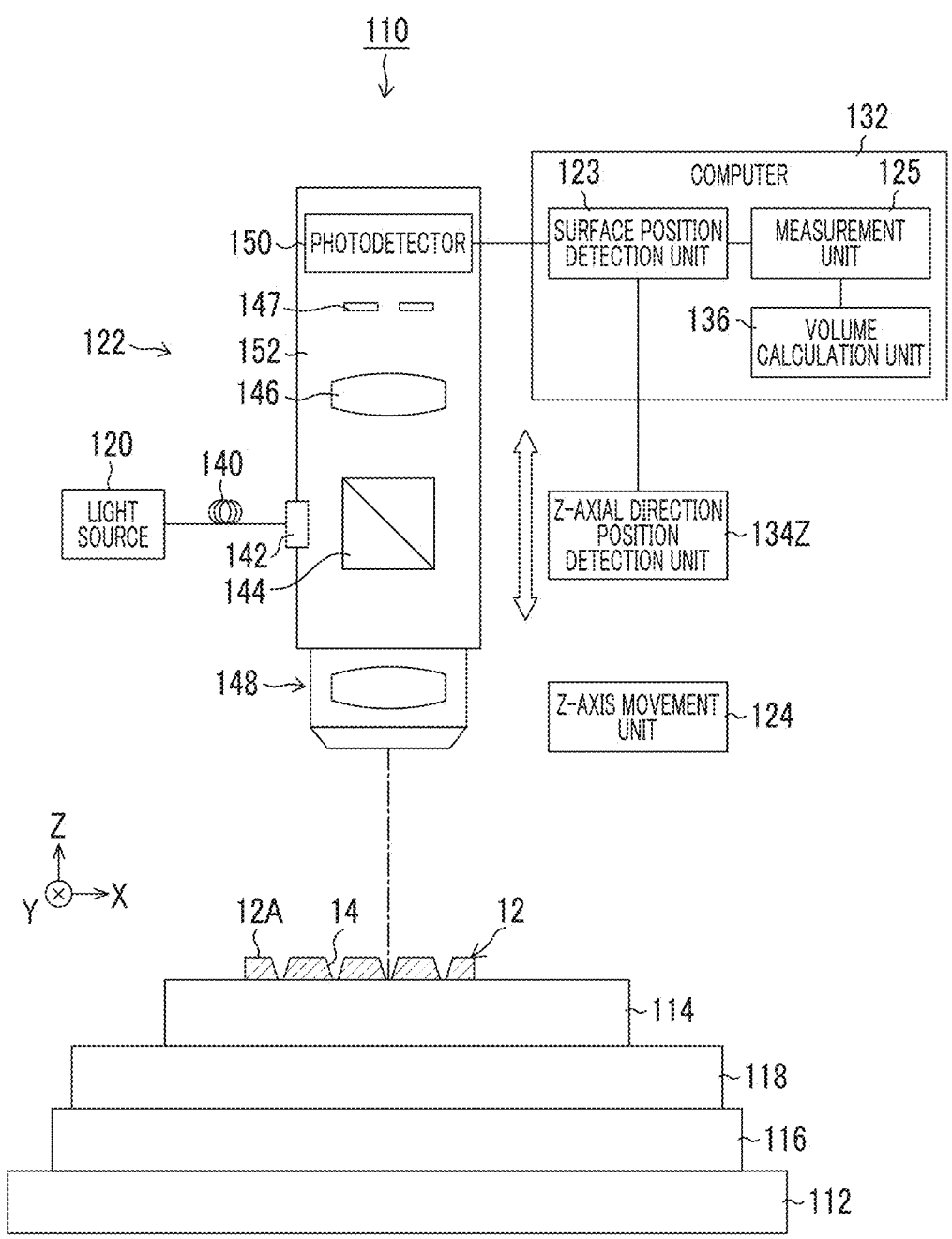
FIG. 6 is a diagram showing a schematic configuration of a confocal microscope in which a needle-shaped recess is a measurement target.

FIG. 6 is a diagram showing a schematic configuration of a measurement unit main body 122 including a light source 120 of a confocal microscope 110 having the confocal optical system which is the first detection unit 101. The confocal microscope 110 shown in FIG. 6 is a device that measures position information of a measurement target (a needle-shaped recess 14 of an empty mold 12 that is not filled with a drug solution 24) using the confocal optical system in a non-contact manner, and is disposed on the first surface 12A of the mold 12.

The confocal microscope 110 includes, as main components, a base 112, a table 114 that supports a measurement target, a table movement unit 116 that moves the table 114 along an X-axial direction and a Y-axial direction on an XY plane (horizontal surface), a position detection unit (not shown) that detects the position of the table 114 in the X-axial direction and the Y-axial direction, a table tilt unit 118 that tilts the table 114 around an X-axis and a Y-axis, a tilt angle detection unit (not shown) that detects tilt angles of the table 114 around the X-axis and the Y-axis, the light source 120 that emits laser light, the measurement unit main body 122, a Z-axis movement unit 124 that moves the measurement unit main body 122 along a Z-axial direction (vertical direction), a Z-axial direction position detection unit 134Z that detects the position of the measurement unit main body 122 in the Z-axial direction, and a computer 132 that controls entire operations and performs various calculation processes. A display which serves as a display unit, a keyboard and a mouse which serve as an operation unit, and a hard disk drive device which serves as a storage unit are connected to the computer 132.

The measurement unit main body 122 includes a collimator 142, a beam splitter 144, an imaging lens 146, a pinhole plate 147, an objective lens 148, and a photodetector 150. The respective components of the measurement unit main body 122 are integrally provided in the measurement unit main body 152.

The light source 120 includes a light source that emits monochromatic light, and for example, is configured with a monochromatic laser light source. Light emitted from the light source 120 propagates to the measurement unit main body 122 through a light guide 140.

The collimator 142 converts the light propagated from the light source 120 through the light guide 140 into parallel light to be then incident to the beam splitter 144. The beam splitter 144 reflects the light output from the collimator 142 to be incident to the objective lens 148.

The objective lens 148 concentrates the light output from the beam splitter 144 to be then irradiated onto a surface of the needle-shaped recess 14 of the mold 12, which is a measurement target surface.

The light reflected from the surface of the needle-shaped recess 14 is incident to the beam splitter 144 through the objective lens 148 again, and passes through the beam splitter 144 to be then incident to the imaging lens 146. The imaging lens 146 concentrates the light passed through the beam splitter 144 to be then incident to the photodetector 150.

The pinhole plate 147 includes a pinhole and is disposed at a focal position of the imaging lens 146. The light concentrated by the imaging lens 146 passes through the pinhole of the pinhole plate 147 to be then incident to the photodetector 150. The photodetector 150 converts the intensity of the received light into an electric signal and outputs the result to the computer 132.

Using the confocal optical system having the above-described configuration, it is possible to obtain information about the height (position in the Z-axial direction) of the surface of the needle-shaped recess 14. Hereinafter, its principle will be briefly described.

If the measurement unit main body 122 is moved in the Z-axial direction by the Z-axis movement unit 124, the focal position of the objective lens 148 is changed.

If the focus of the objective lens 148 is formed on the surface of the needle-shaped recess 14, the light concentrated by the imaging lens 146 forms a focus at the position of the pinhole of the pinhole plate 147. Thus, almost the entirety of the light reflected from the surface of the needle-shaped recess 14 passes through the pinhole of the pinhole plate 147. Accordingly, if the focus of the objective lens 148 is formed on the surface of the needle-shaped recess 14, the intensity of the light received by the photodetector 150 becomes a maximum.

On the other hand, in a state where the focus of the objective lens 148 deviates from the surface of the needle-shaped recess 14, the light concentrated by the imaging lens 146 is focused at a position that deviates from the pinhole plate 147. Thus, part of the light reflected from the surface of the needle-shaped recess 14 cannot pass through the pinhole. Accordingly, if the focus of the objective lens 148 deviates from the surface of the needle-shaped recess 14, the intensity of the light received by the photodetector 150 is noticeably lowered.

In this way, the intensity of the light detected by the photodetector 150 becomes a maximum when the focus of the objective lens 148 is formed on the surface of the needle-shaped recess 14. Accordingly, if the Z-axial direction position of the measurement unit main body 122 is detected when the intensity of the light detected by the photodetector 150 becomes a maximum, it is possible to unmistakably calculate the Z-axial direction position of the measurement point of the surface of the needle-shaped recess 14.

The computer 132 executes a predetermined program to function as the surface position detection unit 123, and detect a position z of the measurement point in the Z-axial direction on the basis of the intensity of the light detected by the photodetector 150 and the position of the measurement unit main body 122 in the Z-axial direction detected by the Z-axial direction position detection unit 134Z.

Further, the computer 132 executes a predetermined program to function as a scanning control unit that moves the table movement unit 116 and irradiates a measurement light beam to a desired measurement point (a measurement point (x, y) on the XY plane) on the surface of the needle-shaped recess 14. Thus, it is possible to detect a three-dimensional position (x, y, z) on the surface of the needle-shaped recess 14 from the position (x, y) of the measurement point on the XY plane where the measurement light beam is irradiated and the position z of the measured measurement point in the Z-axial direction.

Here, the surface of the needle-shaped recess 14 is scanned to measure the three-dimensional positions (x, y, z) of multiple measurement points, to thereby obtain the shape (three-dimensional shape) of the surface of the needle-shaped recess 14.

The detection unit is able to acquire position information of a measurement target, that is, information regarding a three-dimensional position (x, y, z) thereof. A first detection unit 101 detects position information using the needle-shaped recess 14 as a measurement target, and a second detection unit 103 (which will be described later) detects position information using the drug solution 24 that fills the needle-shaped recess 14 or the drug 26 as a measurement target. That is, the "first" and the "second" with respect to the detection unit are used for representing a difference between measurement targets.

The position information (x, y, z) obtained by the surface position detection unit 123 is output to the measurement unit 125 of the computer 132. The measurement unit 125 measures the shape of the needle-shaped recess 14, that is, the three-dimensional shape of the needle-shaped recess 14 on the basis of the position information (x, y, z) which is a detection result based on the confocal microscope 110. The measurement unit 125 may obtain the three-dimensional shape of the needle-shaped recess 14 by connecting the position information (x, y, z) with respect to the entirety of a field of vision.

The confocal microscope 110 including the components up to the surface position detection unit 123 forms the first detection unit 101. Further, the measurement unit 125 calculates the three-dimensional shape on the basis of the position information (x, y, z) which is a detection result. In this embodiment, since the measurement target is the needle-shaped recess 14, the measurement unit 125 forms the first measurement unit 102.

In a case where multiple measurement points are measured, there is a concern that a measurement time becomes long. Accordingly, a method for reducing the number of the measurement points as much as possible and calculating a z coordinate at a different position through interpolation on the basis of the measurement points may be used. As the interpolation method, a known method, for example, any interpolation among polynomial interpolation of a two or higher order, spline interpolation (including B-spline curve interpolation), and Lagrange interpolation may be used.

In this embodiment, the detection of the position information of the needle-shaped recess 14 is performed by the confocal microscope 110, but the invention is not limited thereto, and a different method may be used. For example, a triangulation type displacement meter formed by combination of a light emitting element and a light receiving element, or the like may be used.

It is preferable that the acquisition of the shape data of the needle-shaped recess 14 based on the confocal microscope 110 and the measurement unit 125 is performed in the process (step S1) of preparing the mold in FIG. 1.

The size, the angle of a tilt surface, or the like of the needle-shaped recess 14 is calculated from the three-dimensional shape of the needle-shaped recess 14. The calculation result is output to the volume calculation unit 136 as needle-shaped recess shape data, and is stored in the volume calculation unit 136 as the needle-shaped recess shape data. The volume calculation unit 136 corresponds to the calculation unit 105 in the measurement system 100.

Then, the acquisition of the shape data of the drug solution 24 or the drug 26 that fills the needle-shaped recess 14 will be described. In this embodiment, the second detection unit 103 detects position information of the drug solution 24 or the drug 26 that fills the needle-shaped recess 14, and for example, a displacement meter of a method using a confocal optical system, a method using refraction of light incident to a drug solution, a method using absorption of light incident to a drug solution, and a triangulation method formed by combination of a light emitting element and a light receiving element may be applied thereto.

<First Aspect>

Figure 7:
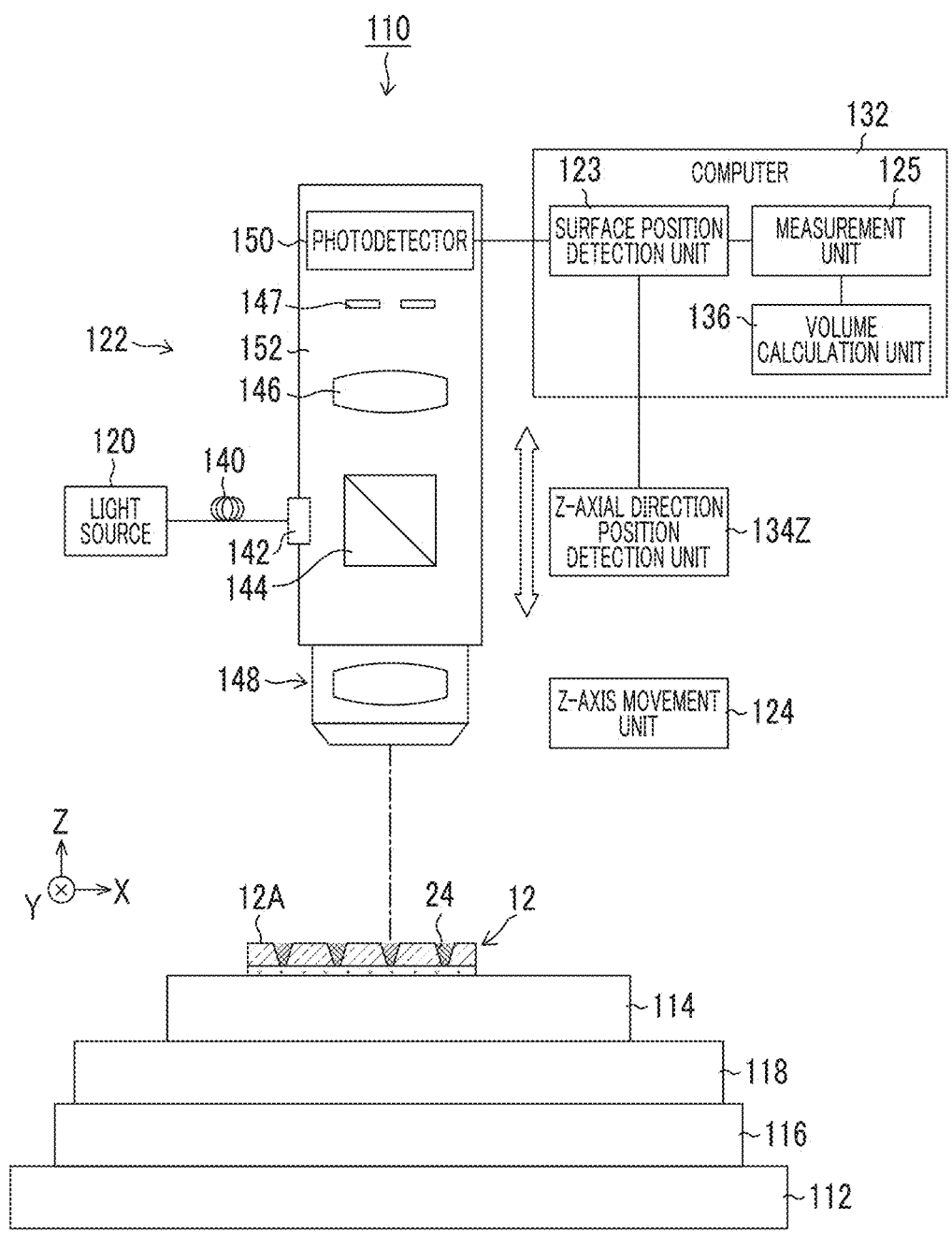
FIG. 7 is a diagram showing a schematic configuration of a confocal microscope in which a drug solution that fills a needle-shaped recess is a measurement target.

A first aspect relates to a method using a confocal optical system. FIG. 7 is a diagram showing a schematic configuration of the measurement unit main body 122 that includes the light source 120 of the confocal microscope 110 that includes a confocal optical system as the second detection unit 103. The confocal microscope 110 in FIG. 7 has substantially the same configuration as that of the confocal microscope 110 described in FIG. 6, and has a different measurement target.

The confocal microscope 110 shown in FIG. 7 is a device that measures position information of a measurement target (drug solution 24) using a confocal optical system in a non-contact manner and is disposed on the first surface 12A of the mold 12.

Using the confocal optical system with such a configuration, it is possible to obtain information regarding the height of the surface of the drug solution 24 (position in the z-axial direction). Its principle is basically the same as in a case where the needle-shaped recess described in FIG. 6 is obtained.

That is, by detecting the z-axial direction position of the measurement unit main body 122 when the intensity of light detected by the photodetector 150 becomes a maximum, it is possible to unmistakably calculate positions of measurement points of the surface of the drug solution 24 in the z-axial direction.

The computer 132 executes a predetermined program to function as the surface position detection unit 123, and detects the position z of the measurement point in the z-axial direction on the basis of the intensity of the light detected by the photodetector 150 and the position of the measurement unit main body 122 in the Z-axial direction detected by the Z-axial direction position detection unit 134Z.

Further, the computer 132 executes a predetermined program to function as a scanning control unit that moves the table movement unit 116 and irradiates a measurement light beam to a desired measurement point (a measurement point (x, y) on the XY plane) on the surface of the drug solution 24. Thus, it is possible to detect a three-dimensional position (x, y, z) on the surface of the drug solution 24 from the position (x, y) of the measurement point on the XY plane where the measurement light beam is irradiated and the position z of the measured measurement point in the Z-axial direction.

It is possible to calculate the shape (three-dimensional shape) of the surface of the drug solution 24 by scanning the surface of the drug solution 24 and measuring three-dimensional positions (x, y, z) of multiple measurement points.

The position information (x, y, z) obtained by the surface position detection unit 123 is output to the measurement unit 125 of the computer 132. The measurement unit 125 measures the shape (three-dimensional shape) of the surface of the drug solution 24 on the basis of the position information (x, y, z) which is the detection result based on the confocal microscope 110. The measurement unit 125 measures the shape (three-dimensional shape) of the surface of the drug solution 24 on the basis of the position information (x, y, z) which is a detection result based on the confocal microscope 110. The measurement unit 125 may obtain the three-dimensional shape of the needle-shaped recess 24 by connecting the position information (x, y, z) with respect to the entirety of a field of vision.

The confocal microscope 110 including the components up to the surface position detection unit 123 forms the second detection unit 103. Further, since the measurement target is the drug solution 24 that fills the needle-shaped recess 14, the measurement unit 125 forms the second measurement unit 104.

Even in the measurement of the three-dimensional shape of the surface of the drug solution 24, it is possible to reduce the number of measurement points as much as possible and to calculate z coordinates of other positions on the basis of the measurement points through spline interpolation. As the interpolation method, any interpolation among known methods, for example, polynomial interpolation of a two or higher order, spline interpolation (including B-spline curve interpolation), and Lagrange interpolation may be used.

As a different method, a method for measuring surface shapes of a plurality of drug solutions 24 in advance and setting the measured surface shapes as predict information for surface shapes of a plurality of models measured with high accuracy may be used. By performing fitting to a model including a feature amount of the three-dimensional shape of the surface of the drug solution 24 on the basis of the predict information and the three-dimensional information of the surface of the drug solution 24, it is possible to calculate the three-dimensional shape of the surface of the drug solution 24 even in a case where the number of measurement points is small.

Figure 8A:
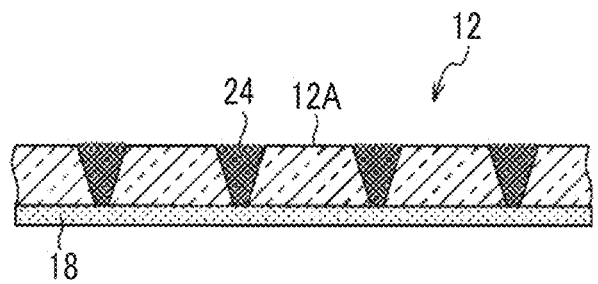
FIGS. 8A to 8D are diagrams illustrating state changes of a drug solution that fills a needle-shaped recess.
Figure 8B:
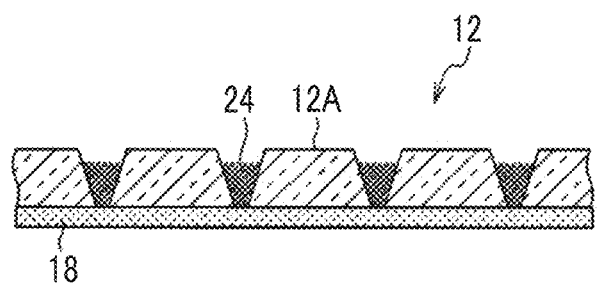
Figure 8C:
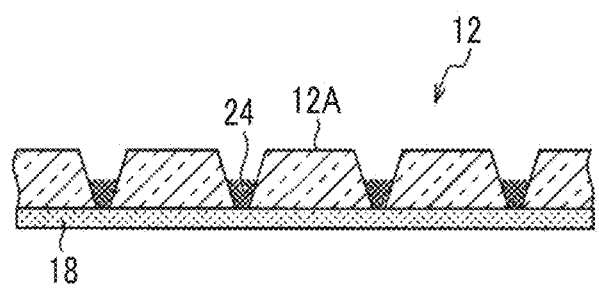
Figure 8D:
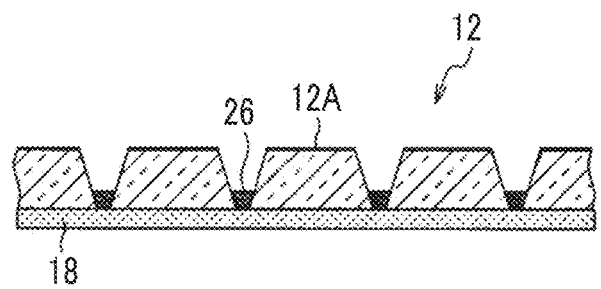

FIGS. 8A to 8D show state changes of the drug solution 24 from the process (step S2 in FIG. 1) of filling the needle-shaped recess 14 of the mold 12 with the drug solution 24 to the process (step S3 in FIG. 1) of drying the drug solution 24 to form the drug 26 in the needle-shaped recess 14. Here, FIG. 8A shows a state immediately after the drug solution 24 is provided in the needle-shaped recess 14, FIG. 8B shows a first drying state where the drug solution 24 in the mold 12 is being dried, FIG. 8C shows a second drying state where the drug solution 24 in the mold 12 is being further dried, and FIG. 8D shows a state in which the drug solution 24 of the mold 12 is completely dried to obtain the drug 26.

The acquisition of the shape data of the drug solution 24 and the drug 26 of the needle-shaped recess 14 in the confocal microscope 110 and the measurement unit 125 is performed between the states from FIG. 8A to FIG. 8D, that is, between the process (step S2 in FIG. 1) of filling the needle-shaped recess 14 of the mold 12 with the drug solution 24 to the process (step S3 in FIG. 1) of drying the drug solution 24 to form the drug 26 in the needle-shaped recess 14.

A surface shape is calculated from the three-dimensional shape of the drug solution 24 or the drug 26. Then, the calculated surface shape is output to the volume calculation unit 136 as surface shape data and is stored in the volume calculation unit 136 as the surface shape data. The volume calculation unit 136 corresponds to the calculation unit 105 of the measurement system 100.

Information about the three-dimensional shape of the needle-shaped recess 14 of the mold 12 calculated from the confocal microscope 110 shown in FIG. 6 is stored in the volume calculation unit 136. The volume calculation unit 136 calculates a space (that is, the volume of the drug solution 24) formed by the three-dimensional shape of the surface of the drug solution 24 and the three-dimensional shape (shape data) of the needle-shaped recess 14.

<Second Aspect>

Figure 9:
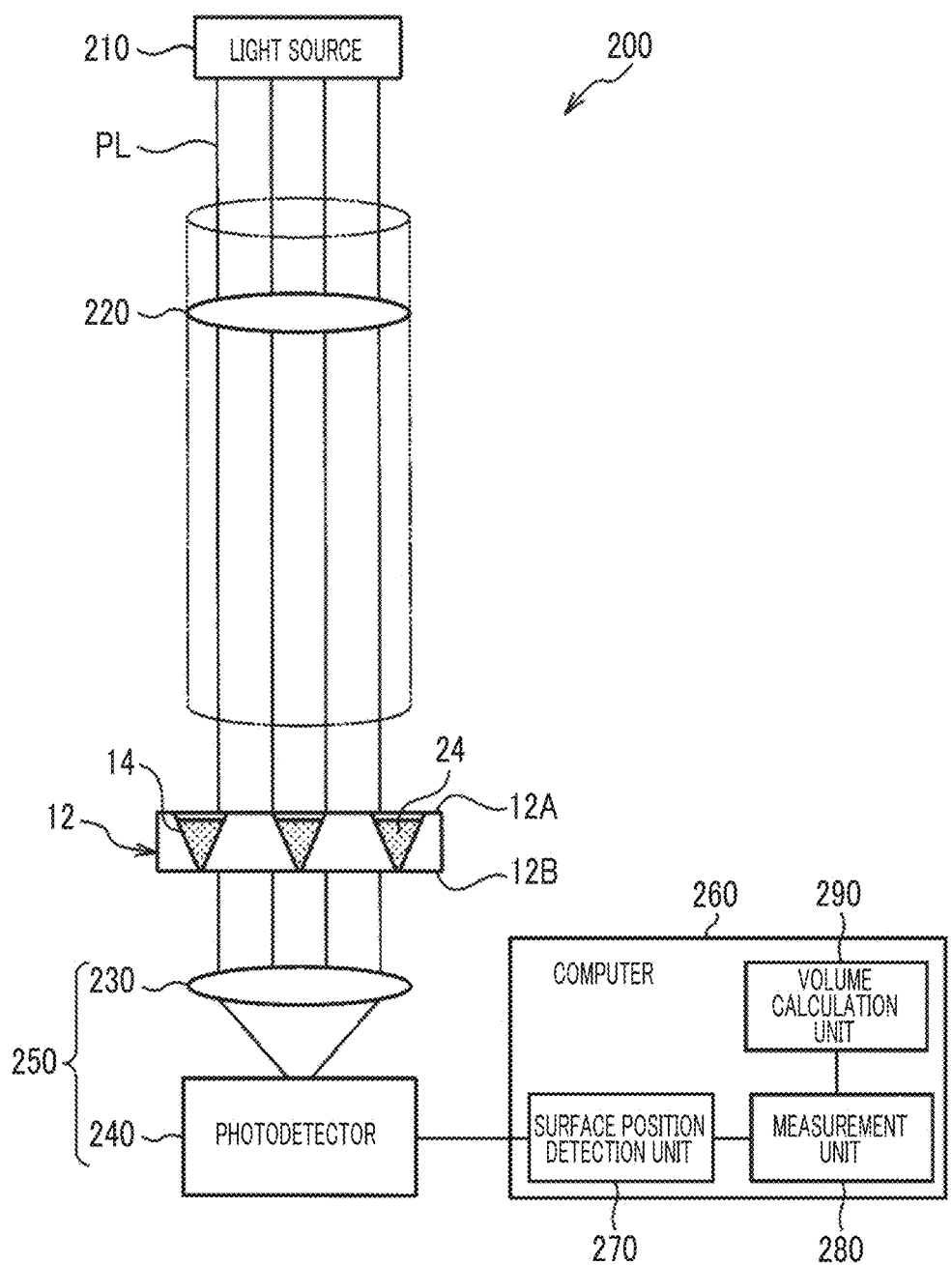
FIG. 9 is a schematic diagram of a measurement apparatus that measures the volume of a drug solution that fills a needle-shaped recess of a mold.

A second aspect relates to a method using refraction of light incident to a drug solution. FIG. 9 is a schematic diagram of a measurement apparatus 200. The measurement apparatus 200 measures the volume of the drug solution 24 that fills the needle-shaped recess 14 of the mold 12. The measurement apparatus 200 includes a light source 210 corresponding to an emission unit, an interference filter 220, and an imaging unit 250 including a lens 230 and a photodetector 240, and a computer 260 that controls entire operations and performs various calculation processes. Further, in the measurement apparatus 200, a stage (not shown) that supports the mold 12 between the interference filter 220 and the imaging unit 250 is provided.

The measurement apparatus 200 acquires and analyzes a transmitted light beam pattern image indicating a transmitted light beam intensity distribution of transmitted light beams of parallel light beams PL which are vertically incident to the first surface 12A of the mold 12 and is emitted from the second surface 12B, to thereby measure the volume of the drug solution 24 for each needle-shaped recess 14. Details thereof will be described later, but since a refractive index of parallel light beams PL which are incident to a wall surface of the needle-shaped recess 14 in the drug solution 24 and a refractive index of parallel light beams PL which are incident to a wall surface of the needle-shaped recess 14 outside the drug solution 24 (on a solution surface) are different from each other, the transmitted light beam pattern image reflects the shape of the surface of the drug solution 24 in the needle-shaped recess 14 and the height of the surface. Thus, it is possible to measure the volume of the drug solution 24 for each needle-shaped recess 14 by analyzing the transmitted light beam pattern image. The height of the surface of the drug solution 24 refers to the height to the surface with reference to the second surface 12B. Since the parallel light beams PL are vertically incident, it is preferable that the light source 210 is a surface light source.

FIGS. 10A to 10C are diagrams illustrating acquisition of a transmitted light beam pattern image 300 in the measurement apparatus 200. Here, FIG. 10A is a perspective view of the mold 12 which is set in the above-described stage, FIG. 10B is a cross-sectional view of the mold 12, and FIG. 10C is a front view of the transmitted light beam pattern image 300.

As shown in FIG. 9 and FIG. 10A, the light source 210 is disposed above the mold 12. The light source 210 emits the parallel light beams PL orthogonal (including approximately orthogonal) to the first surface 12A toward the first surface 12A of the mold 12 after filling of the drug solution 24. The parallel light beams PL have a central wavelength of $\lambda$ (which will be described later).

The interference filter 220 (see FIG. 9) is disposed between the light source 210 and the first surface 12A of the mold 12. The interference filter 220 allows parallel light beams PL of the wavelength $\lambda$ which is a specific wavelength band among the parallel light beams PL incident from the light source 210 to pass therethrough. Thus, the parallel light beams PL of the wavelength $\lambda$ are incident to the first surface 12A of the mold 12. In this way, by limiting the wavelength of the parallel light beams P incident to the mold 12, it is possible to easily detect a surface feature line 420 (see FIG. 14) included in the transmitted light beam pattern image 300, details of which will be described later. In this embodiment, the wavelength of the parallel light beams PL incident to the first surface 12A is determined by both of the light source 210 and the interference filter 220, but the wavelength of the parallel light beams PL may be determined by any one thereof.

As shown in FIG. 9 and FIG. 10B, the lens 230 that forms the imaging unit 250 is disposed under the mold 12, that is, at a position that faces the second surface 12B of the mold 12, and image-forms transmitted light beams of the parallel light beams PL that pass through the mold 12 on the imaging surface of the photodetector 240.

The photodetector 240 that forms the imaging unit 250 is disposed under the lens 230, that is, on a side opposite to a side of the lens 230 that faces the mold 12. The photodetector 240 is a charge coupled device (CCD) imaging element or a complementary metal oxide semiconductor (CMOS) imaging element, and images transmitted light beams formed on the imaging surface by the lens 230. The photodetector 240 is not particularly limited to the CCD imaging element or the CMOS imaging element.

Since the imaging unit 250 images the transmitted light beams of the parallel light beams PL that pass through the mold 12, imaging in the photodetector 240 is performed in a focused state on the second surface 12B of the mold 12. As a method for performing focus adjustment of the imaging unit 250 on the second surface 12B, for example, various methods such as a method for forming a mark (which may be an uneven character or symbol) which is a target of focus adjustment in the imaging unit 250 on the second surface 12B and performing focus adjustment of the imaging unit 250 using the mark as a target, or a method for performing focus adjustment of the imaging unit 250 using wastes, scars, or various scrapes on the second surface 12B as targets may be employed.

As shown in FIG. 10C, the imaging unit 250 generates image data on the transmitted light beam pattern image 300 corresponding to a transmitted light beam image of the invention using an image processing circuit (not shown) on the basis of an imaging signal output from the photodetector 240, and then outputs the image data to the computer 260 (see FIG. 9).

Returning to FIG. 9, the image processing system 26 and analyzes the image data on the transmitted light beam pattern image 300 to calculate the volume of the drug solution 24 that fills each needle-shaped recess 14 of the mold 12, which will be specifically described later.

As shown in FIG. 10C, the transmitted light beam pattern image 300 includes a shading image 310 having a circular shape (including an approximately circular shape) formed by the transmitted light beams that pass through the needle-shaped recess 14 at a position corresponding to each needle-shaped recess 14 of the mold 12. The shading image 310 corresponds to an image pattern, and includes a circular dark image 320 and an annular (ring-shaped) bright image 330 that surrounds an outer circumference of the dark image 320. The dark image 320 corresponds to a second image, and the bright image 330 corresponds to a first image.

A region other than the shading image 310 in the transmitted light beam pattern image 300 becomes a gray image 340 that is brighter than the dark image 320 but is darker than the bright image 330. Hereinafter, the reason why the above-mentioned transmitted light beam pattern image 300 is obtained will be described.

Figure 11A:
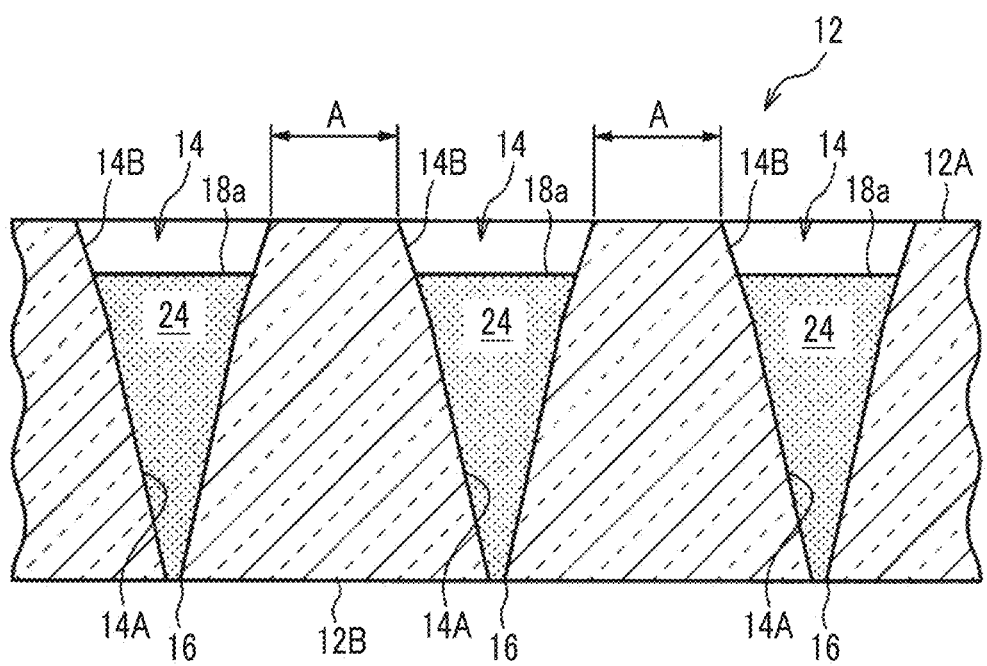
FIG. 11A is a cross-sectional view of a mold to which parallel light beams are incident.
Figure 11B:
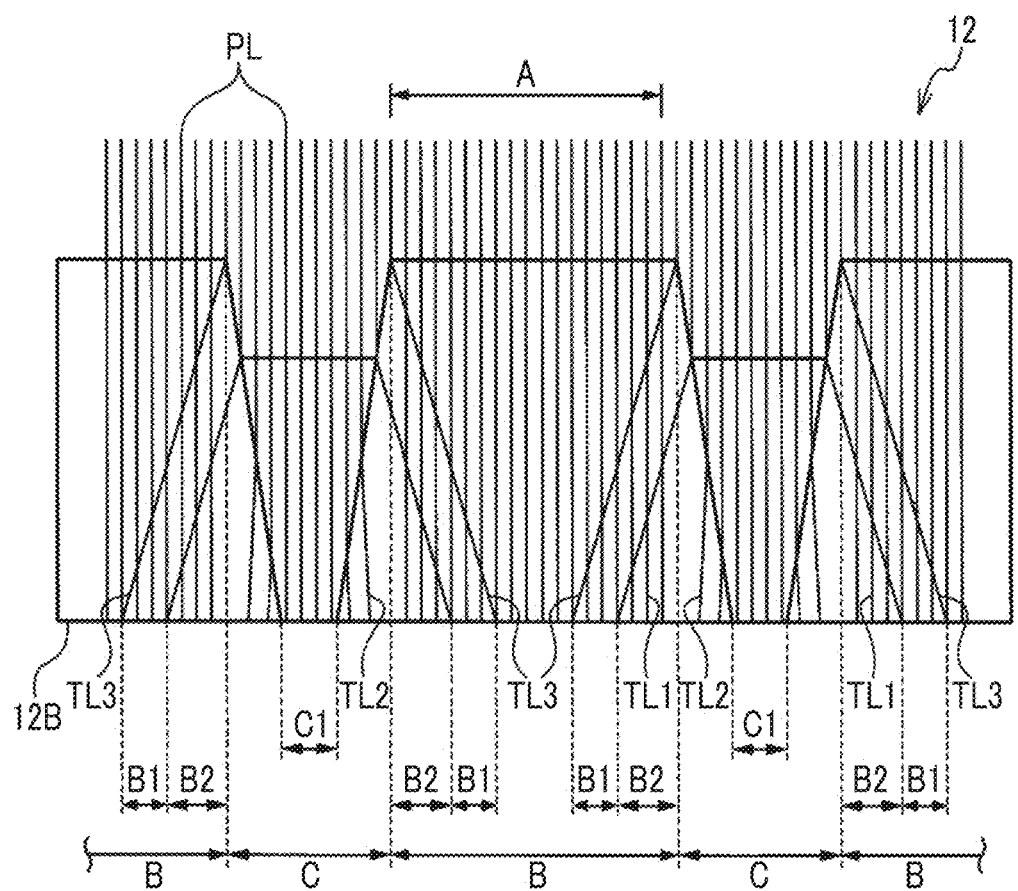
FIG. 11B is a diagram illustrating optical paths (traveling directions) of transmitted light beams of the parallel light beams which pass through the mold.

FIG. 11A is a cross-sectional view of the mold 12 to which the parallel light beams PL are incident, and FIG. 11B is a diagram illustrating optical paths (traveling directions) of transmitted light beams of the parallel light beams PL that pass through the mold 12. In FIG. 11B, for ease of illustration, the number of needle-shaped recesses 14 is reduced compared with FIG. 11A, and the needle-shaped recess 14 is enlarged in a transverse direction in the figure.

As shown in FIGS. 11A and 11B, parallel light beams PL incident to a non-formation region A which is a region where the needle-shaped recess 14 is not formed in the first surface 12A go straight ahead toward the second surface 12B as it is. Thus, a first transmitted light beam TL1 of the parallel light beams PL is emitted from a first region B of the second surface 12B disposed under the non-formation region A of the first surface 12A in the figure.

Parallel light beams PL incident to a first wall surface portion 14A which is disposed in the drug solution 24 among wall surfaces of the needle-shaped recess 14 are refracted at the first wall surface portion 14A. Here, a refractive index of a silicone rubber which is a material of the mold 12 is 1.40 to 1.50, which is a value close to a refractive index (1.35 to 1.50) of the drug solution 24. Thus, the degree of refraction of the parallel light beams PL refracted at the first wall surface portion 14A is weak. Thus, a second transmitted light beam TL2 of the parallel light beams PL refracted at the first wall surface portion 14A is output from a second region C of the second surface 12B disposed under the needle-shaped recess 14 in the figure. The second region C includes a communication hole region C1 corresponding to the communication holes 16.

Parallel light beams PL incident to a second wall surface portion 14B disposed on the side of the first surface 12A with reference to a surface 24A of the drug solution 24 among the wall surfaces of the needle-shaped recess 14, that is, disposed on the surface 24A in the figure are refracted at the second wall surface portion 14B. Here, the refractive index (1.40 to 1.50) of the silicone rubber which is the material of the mold 12 is larger than a refractive index (1.003) of air. Since the refractive indexes of the air and the silicone rubber are greatly different from each other in this way, the parallel light beams PL incident to the second wall surface portion 14B are greatly refracted than the parallel light beams PL incident to the first wall surface portion 14A. Thus, a third transmitted light beam TL3 of the parallel light beams PL refracted at the second wall surface portion 14B is output from a partial region B1 (corresponding to a part in the first region) which is a part of the first region B. Since the second wall surface portion 14B is an annular region around the center of the needle-shaped recess 14, the partial region B1 becomes an annular region around the needle-shaped recess 14. Further, a partial region B2 in the figure is an annular region between the partial region B1 and a second region C.

FIG. 12A is a cross-sectional view of the needle-shaped recess 14 of the mold 12. Here, in FIG. 12A, an aspect ratio of the needle-shaped recess 14 is different from those in FIGS. 11A and 11B. Further, FIG. 12B is a graph illustrating intensity distributions (transmitted light beam intensity distributions) of transmitted light beams (transmitted light beams TL1 to TL3) of the parallel light beams PL that pass through the mold 12. The transverse axis of the graph shown in FIG. 12B represents an axial position indicating a position in an arbitrary direction that is parallel to the first surface 12A and passes through the center of the needle-shaped recess 14 in a radial direction. Further, the longitudinal axis of the graph represents a transmitted light beam intensity.

As shown in FIG. 12A and FIG. 12B, a combined light beam TL4 of the first transmitted light beam TL1 and the third transmitted light beam TL3 is output from the partial region B1. Accordingly, a transmitted light beam intensity of the combined light beam TL4 output from the partial region B1 is higher than a transmitted light beam intensity of the first transmitted light beam TL1 output from the partial region B2 and a transmitted light beam intensity of the second transmitted light beam TL2 output from the second region C.

Further, the transmitted light beam intensity of the second transmitted light beam TL2 output from the second region C becomes lower than the transmitted light intensities of the first transmitted light beam TL1 and the combined light beam TL4 while passing through the drug solution 24. This is because the parallel light beams PL incident to the drug solution 24 are scattered by particles of the drug or the like contained in the drug solution 24. In addition, the transmitted light beam intensity of the second transmitted light beam TL2 output from the communication hole region C1 is higher than the transmitted light beam intensity of the second transmitted light beam TL2 that passes through the mold 12.

In this way, in the transmitted light beam intensity distributions of the transmitted light beams that pass through the mold 12, the transmitted light beam intensity of the combined light beam TL4 output from the partial region B1 is the highest, the transmitted light beam intensity of the first transmitted light beam TL1 output from the partial region B2 is the second highest, and the transmitted light beam intensity of the second transmitted light beam TL2 output from the second region C is the lowest.

In the transmitted light beam intensity distributions shown in FIG. 12B, a boundary position between the partial region B1 and the partial region B2, that is, a boundary position between the combined light beam TL4 and the first transmitted light beam TL1 represents a boundary position between the surface 24A and the second wall surface portion 14B. Since a refractive angle of the parallel light beams PL refracted at the second wall surface portion 14B and the thickness of the mold 12 are uniform, if the boundary position between the surface 24A and the second wall surface portion 14B is changed, the boundary position between the combined light beam TL4 and the first transmitted light beam TL1 is also changed. Hereinafter, details thereof will be specifically described with reference to FIG. 13A to 13C.

FIG. 13A is a cross-sectional view of a needle-shaped recess 14 and a needle-shaped recess 14X in which volumes of the drug solution 24 are different from each other. FIG. 13B is an enlarged view of a region M in FIG. 13A. FIG. 13C is an enlarged view in which a transmitted light beam intensity of a boundary portion on the left side in the figure of the partial regions B1 and B2 shown in FIG. 12B is enlarged, which respectively show a transmitted light beam intensity (in the figure, indicated by a solid line) corresponding to the needle-shaped recess 14X and a transmitted light beam intensity (in the figure, indicated by a dotted line) corresponding to the needle-shaped recess 14X. Here, a case where the volume of the drug solution 24 in the needle-shaped recess 14X is small by 3% compared with the volume of the drug solution 24 in the needle-shaped recess 14 which is a reference (100%) will be described as an example. In this embodiment, the surface 24A in the needle-shaped recess 14X is low by Δh (about 4 μm) compared with the surface 24A in the needle-shaped recess 14.

As shown in FIG. 13A to 13C, in the needle-shaped recess 14X, a boundary position between the surface 24A and the second wall surface portion 14B is low by Δh compared with the boundary position in the needle-shaped recess 14. As a result, a boundary position between the combined light beam TL4 and the first transmitted light beam TL1 corresponding to the needle-shaped recess 14X deviates by M on the side of the second region C with reference to the boundary position between the combined light beam TL4 and the first transmitted light beam TL1 corresponding to the needle-shaped recess 14. The deviation amount Δd is changed according to the thickness of the mold 12, the size of the refractive angle of the second wall surface portion 14B, or the like, and for example, in this embodiment, is a size corresponding to four pixels among pixels of the imaging element. Although not shown, in a case where the surface 24A of the needle-shaped recess 14X is higher than the surface 24A of the needle-shaped recess 14 by Δh, the boundary position between the combined light beam TL4 and the first transmitted light beam TL1 deviates in a reverse direction according to the size of Δh.

In this way, the boundary position between the surface 24A and the second wall surface portion 14B and the boundary position between the combined light beam TL4 and the first transmitted light beam TL1 satisfy one-to-one correspondence. Accordingly, the boundary position between the combined light beam TL4 and the first transmitted light beam TL1 represents the position of the surface 24A of the drug solution 24 that fills the needle-shaped recess 14.

FIG. 11B, FIG. 12B, and FIG. 13C are diagrams showing a one-dimensional transmitted light beam intensity distribution in a direction parallel to the first surface 12A of the mold 12, and an actual transmitted light beam intensity distribution of transmitted light beams that pass through the mold 12 are two-dimensionally expressed.

Figure 14:
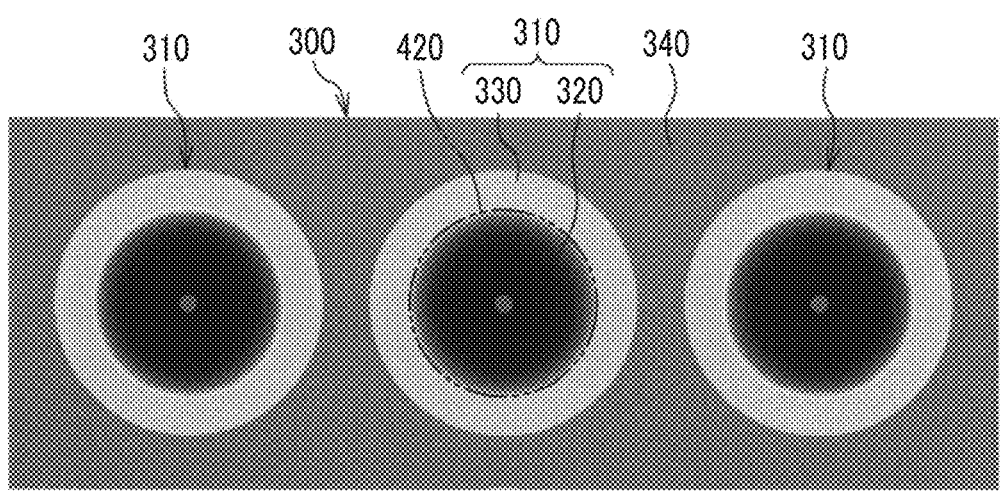
FIG. 14 is an enlarged view in which a part of the transmitted light beam pattern image shown in FIG. 10C is enlarged.

FIG. 14 is an enlarged view in which a part of the transmitted light beam pattern image 300 shown in FIG. 10C. As shown in FIG. 14, the bright image 330 of the shading image 310 is formed by the combined light beam TL4 output from the above-mentioned partial region B1. Further, the dark image 320 of the shading image 310 is formed by the first transmitted light beam TL1 output from the partial region B2 and the second transmitted light beam TL2 output from the second region C. In addition, the gray image 340 is formed by the first transmitted light beam TL1 output from the first region B other than the partial region B1 and the partial region B2. Accordingly, by imaging the transmitted light beams of the parallel light beams PL that pass through the mold 12 using the imaging unit 250, the transmitted light beam pattern image 300 including the shading image 310 is obtained at a position corresponding to each needle-shaped recess 14.

As shown in FIG. 12B, the transmitted light beam intensity of the first the transmitted light beam TL1 output from the partial region B2 is higher than the transmitted light beam intensity of the second the transmitted light beam TL2 output from the second region C. Further, the transmitted light beam intensity of the second transmitted light beam TL2 output from the communication hole region C1 is higher than the transmitted light beam intensity of another second transmitted light beam TL2. As a result, a central portion and a peripheral portion of the dark image 320 are brighter than the other portion of the dark image 320.

In this way, in the transmitted light beam pattern image 300, the bright image 330 is formed by the combined light beam TL4, and the dark image 320 is formed by the first transmitted light beam TL1 or the like. Thus, a boundary position between the dark image 320 and the bright image 330 in each shading image 310 of the transmitted light beam pattern image 300 becomes a surface feature line 420 indicating a boundary position between the surface 24A and the second wall surface portion 14B for each needle-shaped recess 14.

Figure 15A:
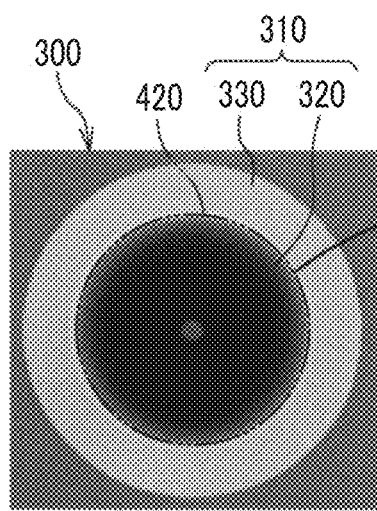
FIGS. 15A and 15B are a front view of a transmitted light beam pattern image in a case where a surface in a needle-shaped recess is parallel to a first surface and a cross-sectional view of a mold.
Figure 15B:
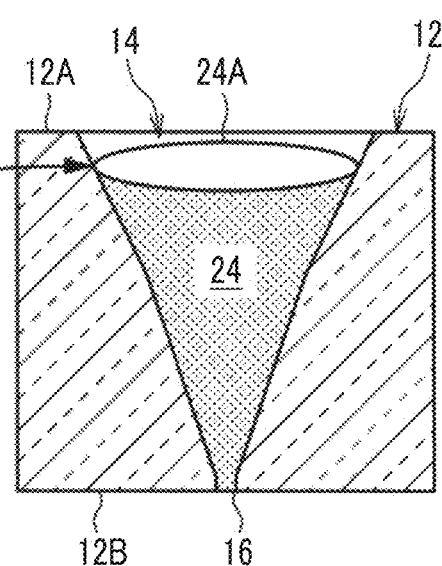
Figure 15C:
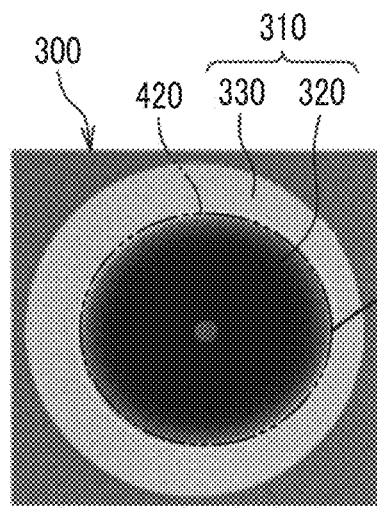
FIGS. 15C and 15D are a front view of a transmitted light beam pattern image in a case where a surface in a needle-shaped recess is inclined with respect to a first surface and a cross-sectional view of a mold.
Figure 15D:
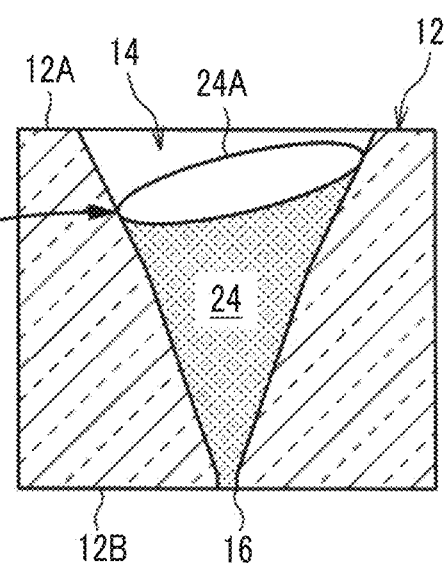

FIGS. 15A and 15B are a front view of the transmitted light beam pattern image 300 in a case where the surface 24A in the needle-shaped recess 14 is parallel to the first surface 12A, and a cross-sectional view of the mold 12. FIGS. 15C and 15D are a front view of the transmitted light beam pattern image 300 in a case where the surface 24A in the needle-shaped recess 14 is inclined with respect to the first surface 12A, and a cross-sectional view of the mold 12.

As shown in FIGS. 15A and 15B, in a case where the surface 24A in the needle-shaped recess 14 is parallel to the first surface 12A, a perfect circle-like surface feature line 420 is detected from the shading image 310 in the transmitted light beam pattern image 300 corresponding to the needle-shaped recess 14. On the other hand, as shown in FIGS. 15C and 15D, in a case where the surface 24A in the needle-shaped recess 14 is inclined with respect to the first surface 12A, an elliptical surface feature line 420 is detected from the shading image 310 in the transmitted light beam pattern image 300 corresponding to the needle-shaped recess 14.

Further, although not shown, the area of the dark image 320 surrounded by the surface feature line 420 increases as the height of the surface 24A in the needle-shaped recess 14 increases, and contrarily, the area of the dark image 320 surrounded by the surface feature line 420 decreases as the height of the surface 24A in the needle-shaped recess 14 decreases. Accordingly, by analyzing the transmitted light beam pattern image 300 to detect the surface feature line 420 for each needle-shaped recess 14, it is possible to detect the boundary position between the surface 24A and the second wall surface portion 14B for each needle-shaped recess 14, that is, the shape and the height of the surface 24A for each needle-shaped recess 14.

In this embodiment, as described above, the wavelength of the parallel light beams PL incident to the first surface 12A of the mold 12 is limited using the interference filter 220 or the like. Since the refractive angle of the parallel light beams PL refracted at the second wall surface portion 14B is changed according to the wavelength of the parallel light beams PL, deviation occurs at a light emitting position of the third transmitted light beam TL3 output from the second surface 12B according to the wavelength. Thus, in a case where the wavelength of the parallel light beams PL incident to the first surface 12A is not limited, there is a concern that the boundary of the bright image 330 becomes obscure due to deviation of an output position for each wavelength of the third transmitted light beam TL3 and the detection of the surface feature line 420 becomes difficult. On the other hand, in this embodiment, since the wavelength of the parallel light beams PL incident to the first surface 12A is limited, it is possible to easily detect the surface feature line 420 included in the transmitted light beam pattern image 300.

As shown in FIGS. 8A to 8D, by drying the mold 12 after each needle-shaped recess 14 is filled with the drug solution 24, water is evaporated from the drug solution 24 in a liquid state in each needle-shaped recess 14 to be solidified, so that the drug 26 is finally formed. An optical feature (a refractive index, a light absorbance, or the like) of the drug 26 which is a crystal of the drug solution 24 is changed according to the type of the drug 26.

On the other hand, the drug solution 24 contains water of about 80%, in which a ratio of the drug 26 is several %, and the remaining component is an HES (hydroxyethyl starch) drug solution, or the like. Accordingly, since the water, the HES drug solution, and the like occupy 95% in the drug solution 24, the water determines the optical feature of the drug solution 24. Thus, although the type of the drug 26 in the drug solution 24 is changed, the optical feature of the drug solution 24 is not greatly changed.

Accordingly, in the measurement apparatus 200, the volume of the drug solution 24 that fills each needle-shaped recess 14 is measured in consideration of the water included in the drug solution 24. A measurement time in the measurement apparatus 200 corresponds to a period before the water included in the drug solution 24 is evaporated and is solidified into the drug 26, and specifically, is immediately after the needle-shaped recess 14 is filled with the drug solution 24 (see FIG. 8A) and is during drying of the drug solution 24 (see FIGS. 8B and 8C).

As shown in FIG. 9 and FIGS. 10A-10C, image data of the transmitted light beam pattern image 300 input from the imaging unit 250 is analyzed, the surface feature line 420 is detected by the surface position detection unit 270, and the shape of the drug solution 24 is measured from the surface feature line 420 and previous measurement data (which will be described later) by the measurement unit 280. The shape data is output to the volume calculation unit 290 from the measurement unit 280, and is stored in the volume calculation unit 290 as shape data. The volume calculation unit 290 corresponds to the calculation unit 105 of the measurement system 100.

Information on the three-dimensional shape of the needle-shaped recess 14 of the mold 12 calculated from the confocal microscope 110 shown in FIG. 6 is stored in the volume calculation unit 290. The volume calculation unit 290 calculates a space (that is, the volume of the drug solution 24) formed by the three-dimensional shape of the surface of the drug solution 24 and the three-dimensional shape of the needle-shaped recess 14.

The surface position detection unit 270 analyzes the image data on the transmitted light beam pattern image 300 input from the photodetector 240 and detects the surface feature line 420 from the shading image 310 for each needle-shaped recess 14. For example, in the transmitted light beam pattern image 300, a brightness value of a white bright image 330 becomes the highest, and a brightness value of a black dark image 320 becomes the lowest. A brightness value of a gray image is lower than the brightness value of the bright image 330 and is higher than the brightness value of the dark image 320. Accordingly, the surface position detection unit 270 detects brightness values of all pixels of the image data of the transmitted light beam pattern image 300 for comparison, to thereby detect the bright image 330 and the dark image 320 from the transmitted light beam pattern image 300.

Then, the surface position detection unit 270 detects a boundary between the bright image 330 and the dark image 320 on the basis of detection results of the bright image 330 and the dark image 320, to thereby detect the surface feature line 420 for each needle-shaped recess 14. Further, the surface position detection unit 270 outputs the image data of the transmitted light beam pattern image 300 and the position information on the surface feature line 420 to the measurement unit 280. A method for detecting the surface feature line 420 is not particularly limited, and the detection may be performed using a known image analysis method.

In addition to the detection results of the measurement unit 280 and the surface position detection unit 270, previous measurement data is used. Next, the previous measurement data will be described. The previous measurement data is data obtained by measuring in advance the radiuses of the surface feature lines 420 of two kinds of surfaces 24A parallel to the first surface 12A and having different surface heights (hereinafter, may also be referred to as surface feature line radiuses") and the surface heights of the two kinds of surfaces 24A.

Figure 16A:
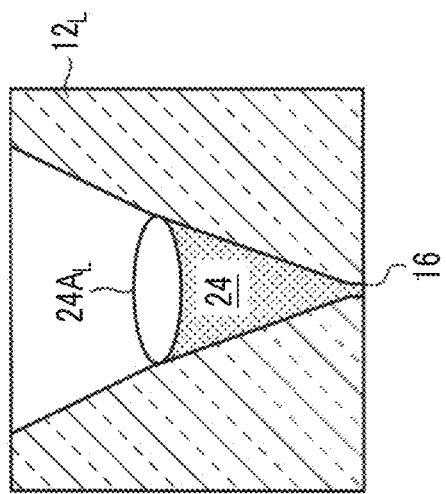
FIG. 16A is a cross-sectional view of a mold in which a first surface is formed in each needle-shaped recess.
Figure 16B:
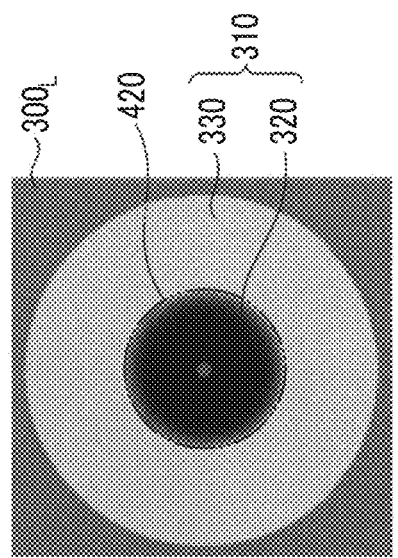
FIG. 16B is a cross-sectional view of a mold in which a second surface is formed in each needle-shaped recess.

Previous measurement data 52 are data obtained by measuring surface feature line radiuses and liquid surface heights of a first surface $24A_H$ and a second surface $24A_L$ parallel to the first surface 12A and having different liquid surface heights, as shown in FIGS. 16A and 16B. Here, FIG. 16A is a cross-sectional view of a mold $12_H$ in which the first surface $24A_H$ is formed in each needle-shaped recess 14 by filling of the drug solution 24. Further, FIG. 16B is a cross-sectional view of a mold $12_L$ in which the second surface $24A_L$ is formed in each needle-shaped recess 14 by filling of the drug solution 24. In this embodiment, the height of the first surface $24A_H$ is higher than the height of the second surface $24A_L$.

When the surface feature line radiuses of the first surface $24A_H$ and the second surface $24A_L$ are measured, first, the molds $12_H$ and $12_L$ are set in the measurement apparatus 200, and then, transmitted light beams that pass through the mold $12_H$ and $12_L$ are imaged by the imaging unit 250.

Figure 16C:
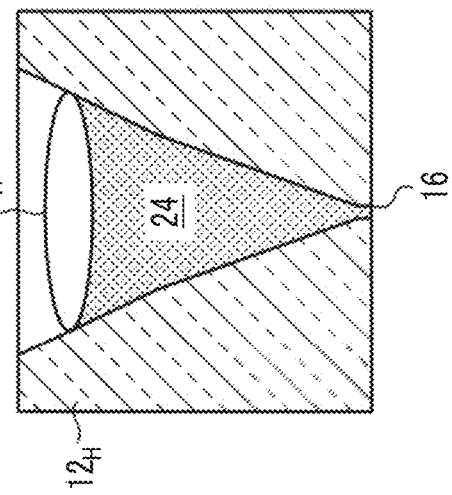
FIG. 16C is a front view of a transmitted light beam pattern image which is generated by imaging transmitted light beams in the mold shown in FIG. 16A.
Figure 16D:
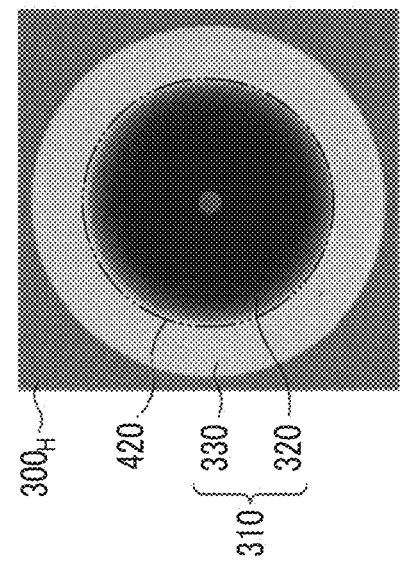
FIG. 16D is a front view of a transmitted light pattern image which is generated by imaging transmitted light beams in the mold shown in FIG. 16B.

FIG. 16C is a front view of a transmitted light beam pattern image $300_H$ which is generated by imaging the transmitted light beams of the mold $12_H$ shown in FIG. 16A using the imaging unit 250. Further, FIG. 16D is a front view of a transmitted light beam pattern image $300_L$ which is generated by imaging the transmitted light beams of the mold $12_L$ shown in FIG. 16B using the imaging unit 250. On the basis of image data of the transmitted light beam pattern images $300_H$ and $300_L$ shown in FIGS. 16C and 16D, as described later, the surface feature line radiuses of the first surface $24A_H$ and the second surface $24A_L$ are measured.

FIG. 17A is a diagram illustrating measurement of the radius of the surface feature line of the first surface $24A_H$, and FIG. 17B is a diagram illustrating measurement of the radius of the surface feature line of the second surface $24A_L$.

As shown in upper and middle parts of FIGS. 17A and 17B, in this embodiment, by acquiring the image data of the transmitted light beam pattern images 300H and 300L of the respective molds $12_H$ and $12_L$ generated by the imaging unit 250 using the above-mentioned photodetector 240 and analyzing both the pieces of image data using the surface position detection unit 270, the surface feature lines 420 of the respective molds $12_H$ and $12_L$ are detected.

Then, as shown in lower parts of FIGS. 17A and 17B, a surface feature line radius $R_H$ indicating a distance to each of a plurality of points on the surface feature line 420 of the mold $12_H$ from the center (including approximately the center) of the needle-shaped recess 14 is measured, and then, an average value of the surface feature line radius $R_H$ for each of the plurality of points is stored in the measurement unit 280 as previous measurement data. Further, a surface feature line radius $R_L$ indicating a distance to each of a plurality of points of the surface feature line 420 of the mold $12_L$ from the center (including approximately the center) of the needle-shaped recess 14 is measured, and then, an average value of the surface feature line radius $R_L$ for each of the plurality of points is stored in the measurement unit 280 as previous measurement data. The surface feature line radius $R_H$ corresponds to a first radius, and the surface feature line radius $R_L$ corresponds to a second radius. Further, in this embodiment, the surface feature line radiuses $R_H$ and $R_L$ are measured by a radius detection unit (which will be described later).

Here, the transmitted light beam intensity of the second transmitted light beam TL2 output from the center of the needle-shaped recess 14, that is, the communication hole 16 (communication hole region C1) is higher than the transmitted light beam intensity of the second transmitted light beam TL2 output from the second region C other than the communication hole region C1, as described above. Thus, it is possible to determine the center of the needle-shaped recess 14 on the transmitted light beam pattern image 300.

In addition, the average values of the surface feature line radiuses $R_H$ and $R_L$ may be, for example, average values of the surface feature line radiuses $R_H$ and $R_L$ to the plurality of points on all the surface feature lines 420 detected for each needle-shaped recess 14, or instead, may be average values of the surface feature line radiuses $R_H$ and $R_L$ to the plurality of points on a representative surface feature line 420.

FIGS. 18A and 18B are diagrams illustrating detection of the height of the liquid surface of the first surface $24A_H$ and detection of the height of the liquid surface of the second surface $24A_L$. As shown in FIGS. 18A and 18B, detection of a first surface height $D_H$ from the second surface 12B to the center (including approximately the center) of the first surface $24A_H$ and detection of a second surface height $D_L$ from the second surface 12B to the center (including approximately the center) of the second surface $24A_L$ may be performed by a known laser confocal microscope. Detection results of the first surface height $D_H$ and the second surface height $D_L$ are stored in the measurement unit 280 as previous measurement data.

The previous measurement data including the average values of the surface feature line radiuses $R_H$ and $R_L$ and the first surface height $D_H$ and the second surface height $D_L$ are measured in advance and are stored in the measurement unit 280.

Returning to FIG. 9, the measurement unit 280 measures the shape of the drug solution 24 on the basis of a detection result of the surface position detection unit 270 and the previous measurement data stored in the measurement unit 280. In the measurement unit 280, a radius detection unit (not shown) that detects the surface feature line radius of the surface 24A and a surface height detection unit (not shown) that detects the surface height of the surface 24A are provided.

FIG. 19A is a diagram illustrating a surface feature line radius detection process using the radius detection unit of the measurement unit 280, and FIG. 19B is a diagram illustrating a liquid surface height detection process using the liquid surface height detection unit of the measurement unit 280.

As shown in FIG. 19A, the radius detection unit detects a surface feature line radius $R_X$ indicating a distance from the center (including approximately the center) of the needle-shaped recess 14 to each point $C_X$ (only one point is shown in the figure) of one circle of the surface feature line 420 is detected on the basis of the detection result of the surface feature line 420 input from the surface position detection unit 270 and the image data of the transmitted light beam pattern image 300. The surface feature line radius $R_X$ corresponds to a third radius. Further, the radius detection unit outputs a detection result of the surface feature line radius $R_X$ of each point $C_X$ on the surface feature line 420 to the liquid surface height detection unit.

As shown in FIG. 19B, the surface height detection unit detects a third surface height $D_X$ from the second surface 12B with respect to each point $C_X$ on the surface feature line 420. The surface height detection unit performs a surface height calculation process for detecting the third liquid surface height $D_X$ of each point $C_X$ on the basis of the detection result of the surface feature line radius $R_X$ of each point CX input from the radius detection unit and the previous measurement data 52 ($R_H$, $R_L$, $D_H$, and $D_L$) stored in the measurement unit 280.

Figure 20:
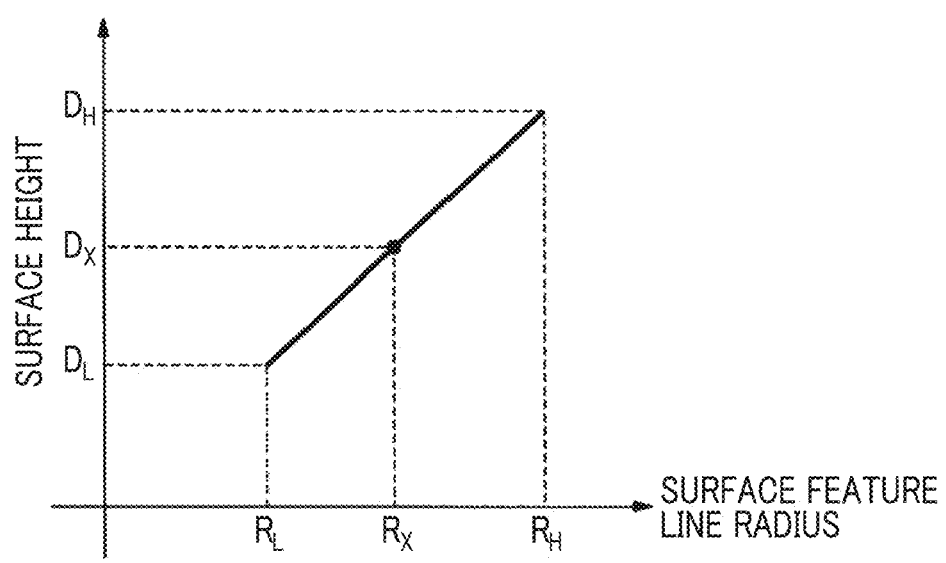
FIG. 20 is a diagram illustrating a surface height calculation process in the surface height detection unit.

FIG. 20 is a diagram illustrating the surface height calculation process in the surface height detection unit. Since the shape of the needle-shaped recess 14 is uniform, as shown in FIG. 20, a one-to-one correspondence is established between the "surface feature line radius" and the "surface height", and the correspondence is expressed as a primary function defined by the previous measurement data 52 ($R_H$, $R_L$, $D_H$, and $D_L$). Thus, the surface height detection unit can substitute the detection result of the surface feature line radius $R_X$ of each point $C_X$ in Expression (1), thereby calculating the third liquid surface height $D_X$ of each point $C_X$. Thus, the surface height of one circle of the surface feature line 420 is measured. Further, the liquid surface height detection unit outputs the measurement result of the third liquid surface height $D_X$ of each point $C_X$ on the surface feature line 420 to the volume calculation unit 290 as shape data of the drug solution 24.

[Expression 1]

$$D_X = [(R_X - R_L) \times (D_H - D_L)]/(R_H - R_L) + D_L \qquad (1)$$

In this embodiment, the measurement apparatus 200 including the components up to the surface position detection unit 270 forms the second detection unit 103. Further, since the measurement target is the drug solution 24 that fills the needle-shaped recess 14, the measurement unit 280 that includes the radius detection unit and the surface height detection unit forms the second measurement unit 104.

Returning to, FIG. 9 and FIGS. 19A-19B, the volume calculation unit 290 calculates the volume of the drug solution 24 that fills the needle-shaped recess 14 on the basis of the shape data of the surface feature line radius $R_X$ of each point $C_X$ on the surface feature line 420 and the third liquid surface height $D_X$, input from the measurement unit 280, and the shape data of the needle-shaped recess acquired by the confocal microscope 110 in FIG. 6.

The shape (including an inclination) and the surface height of the surface 24A of the needle-shaped recess 14 may be detected on the basis of detection results of the surface feature line radius $R_X$ and the liquid surface height $D_X$ of each point $C_X$. Further, the shape of the needle-shaped recess 14 is also known on the basis of the shape data of the needle-shaped recess. Accordingly, the volume calculation unit 290 can detect the volume of the drug solution 24 that fills the needle-shaped recess 14 on the basis of the shape and the liquid surface height of the surface 24A of the needle-shaped recess 14 and the shape of the needle-shaped recess 14.

Using the above-described method, it is possible to calculate the volume of the drug solution 24 that fills all the needle-shaped recesses 14 of the mold 12. The calculation result of the volume of the drug solution 24 is stored in a storage unit (not shown) as a measurement result of the volume of the drug solution 24 for each needle-shaped recess 14 of the mold 12.

Further, the volume calculation unit 290 can calculate the amount of the drug 26 included in the drug solution 24 in the needle-shaped recess 14 on the basis of the measurement result of the volume of the drug solution 24 in the needle-shaped recess 14.

<Third Aspect>

[Overall Configuration of Measurement Apparatus]

Figure 21:
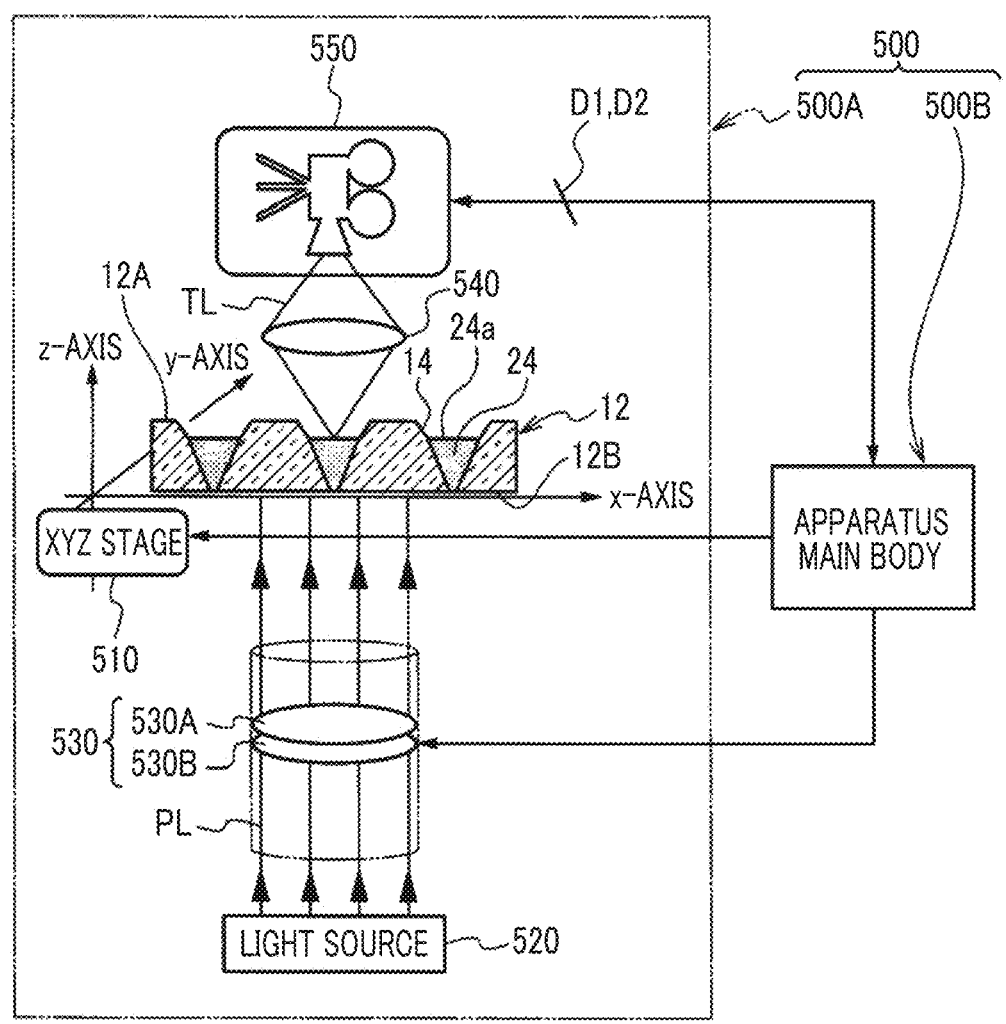
FIG. 21 is a schematic view of a measurement apparatus relating to a measurement method and a measurement apparatus of the invention.

A third aspect relates to a method using absorption of light incident to a drug solution. FIG. 21 is a schematic view of a measurement apparatus 500 according to a measurement method and a measurement apparatus of the invention. The measurement apparatus 500 measures the volume of the drug solution 24 which is a water solution of the drug 26 that fills the needle-shaped recess 14 of the mold 12. The measurement apparatus 500 includes an imaging unit 500A and an apparatus main body 500B, as main components.

A plurality of communication holes 16 respectively connected to the respective needle-shaped recesses 14 are formed on the second surface 12B of the mold 12. After each needle-shaped recess 14 is filled with the drug solution 24, the mold 12 is set in the imaging unit 500A in a state where the first surface 12A is disposed upward in the figure and the second surface 12B is disposed downward in the figure.

Figure 22:
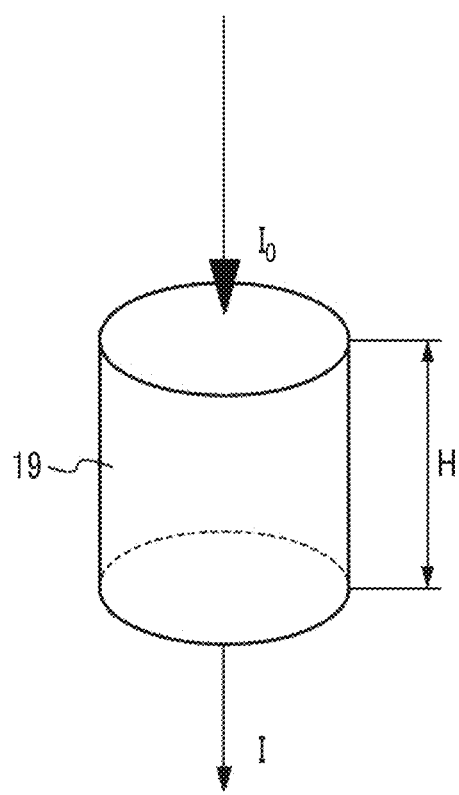
FIG. 22 is a diagram illustrating a light absorption feature of water included in a drug solution.

FIG. 22 is a diagram illustrating a light absorption feature of water 19 included in the drug solution 24. As shown in FIG. 22, in a case where the intensity of light incident to the water 19 is represented as $I_0$ the intensity of light that passes through water is represented as $I$ ($I<I_0$), a distance of light passage through the water 19 is represented as H, and a light absorption coefficient of the water 19 with respect to light of a wavelength $\lambda$ is represented as $\alpha_\lambda$, the light absorption feature of the water 19 is expressed as the following expression.

$$\frac{I}{Io} = 10^{-\alpha_\lambda H} \qquad [\text{Expression 2}]$$

According to Expression 1 described above, since a predetermined relationship is established between absorption of light in the water 19 and a distance H of light passage through the water 19, the distance H may be calculated by measuring the absorption of the light in the water 19.

Figure 23:
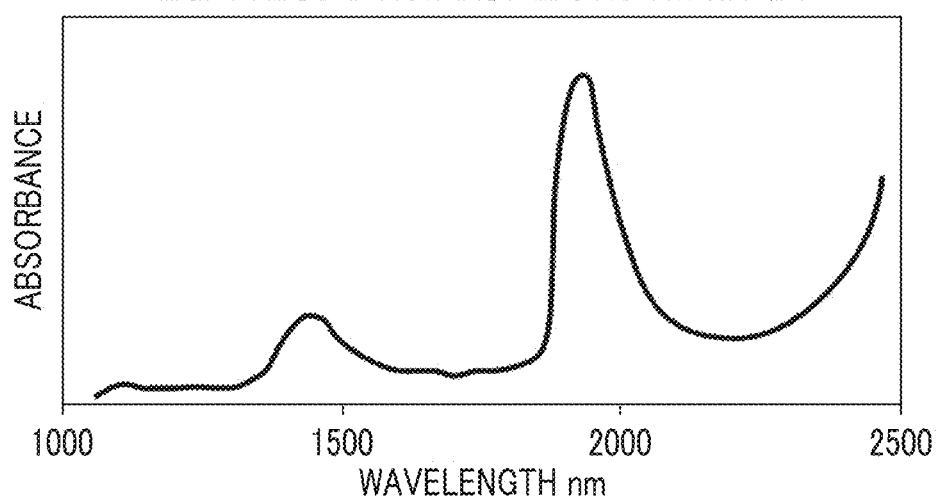
FIG. 23 is a graph of a light absorption distribution indicating a distribution of light absorption of water.

FIG. 23 is a graph of a light absorption distribution indicating a distribution of light absorption of the water 19. In the graph, a transverse axis represents a wavelength band $\lambda$ (nm) of light, and a longitudinal axis represents an absorption factor [log ($I_0/I$)]. As shown in FIG. 23, in a case where the wavelength $\lambda$ (nm) of light is about 1400 nm and about 1900 nm, light absorption in the water 19 becomes large. Accordingly, for example, focusing on light having a wavelength $\lambda$ of about 1400 nm, in a case where the amount of the water 19 is small (in a case where the distance H is short"), the absorption factor of the light becomes small, and contrarily, in a case where the amount of the water 19 is large (in a case where the distance H is long), the absorption factor of light becomes large.

Figure 24:
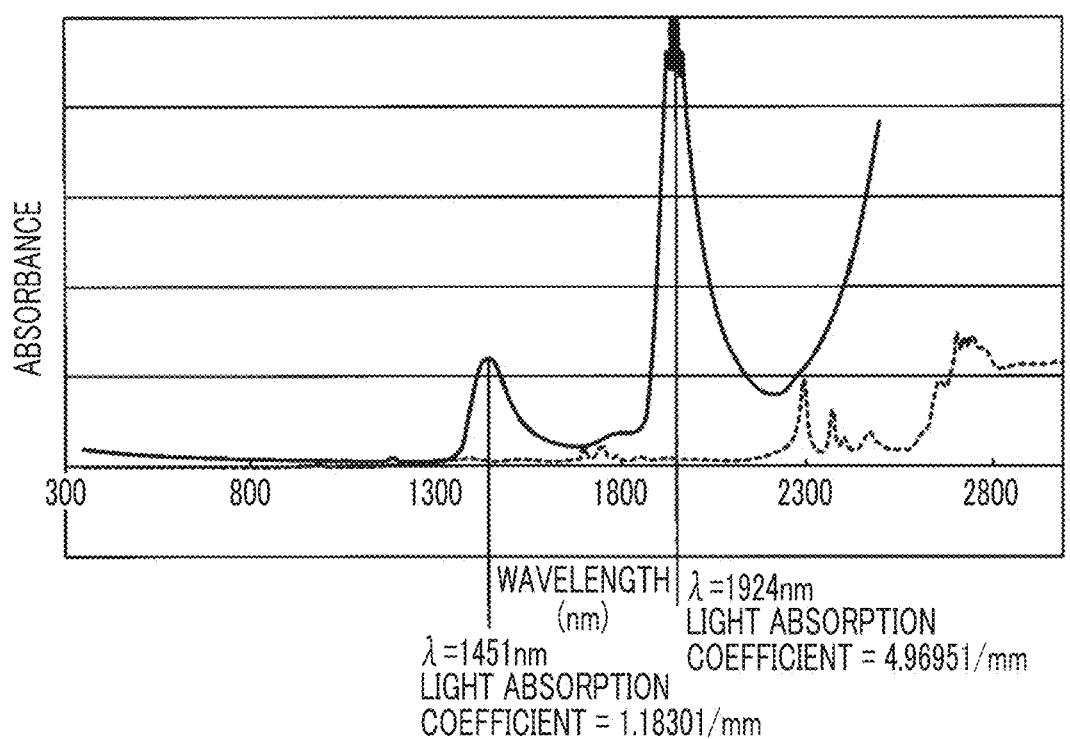
FIG. 24 is a graph of a light absorption distribution indicating a distribution of light absorption of a drug solution.

FIG. 24 is a graph of a light absorption distribution (indicated by a solid line in the figure) indicating a distribution of light absorption of the drug solution 24. In the graph, a transverse axis and a longitudinal axis are the same as those shown in FIG. 23. Further, a light absorption distribution (indicated by a dotted line in the figure) of the mold 12 is also shown in FIG. 24.

As shown in FIG. 24, the light absorption distribution of the drug solution 24 is basically the same as the light absorption distribution in the water 19 shown in FIG. 23, and the wavelength $\lambda$ has a light absorption factorratio which is high in the vicinity of about 1400 nm and about 1900 nm. Accordingly, components (the drug 26 or the like) other than the water 19 included in the drug solution 24 does not basically affect the light absorption in the water 19 included in the drug solution 24. Thus, the measurement apparatus 500 measures the volume of the drug solution 24 that fills the needle-shaped recess 14 focusing on the light absorption in the water 19 included in the drug solution 24, regardless of the kind of the drug 26 included in the drug solution 24.

The drug solution 24 contains water of about 80%, in which a ratio of the drug 26 is several %, and the remaining component is an HES (hydroxyethyl starch) solution or the like. Accordingly, since the drug solution 24 is occupied by water, an HES solution, and the like by 95%, the water included in the drug solution 24 determines an optical feature of the drug solution 24. Thus, even if the kind of the drug 26 in the drug solution 24 is changed, the optical feature of the drug solution 24 is not greatly changed. Thus, the measurement apparatus 500 measures the volume of the drug solution 24 that fills each needle-shaped recess 14 focusing on the light absorption feature of the water included in the drug solution 24.

Accordingly, a measurement time in the measurement apparatus 500 corresponds to a time before the water included in the drug solution 24 is evaporated and is solidified into the drug 26, and specifically, it is preferable that the measurement time is a time immediately after the needle-shaped recess 14 is filled with the drug solution 24 (see FIG. 8A) during which drying of the drug solution 24 is being performed (see FIGS. 8B and 8C).

In a case where measurement is performed while the mold 12 is being dried, it is preferable to perform the measurement at a predetermined period of time when the state of the drug solution 24 is stable. The predetermined period of time when the state of the drug solution 24 is stable is changed according to manufacturing conditions of the MNA 29 (the kind of the drug 26, the shape of the needle-shaped recess 14, a temperature in drying, or the like), the period of time may be determined by performing a test or simulation for each manufacturing condition.

Returning to FIG. 21, in the measurement in the measurement apparatus 500, the imaging unit 500A images transmitted light beams that are vertically incident to the second surface 12B of the mold 12 as measurement light beams, pass through respective portions (drug solution 24 or the like) of the mold 12, and are output from the first surface 12A to obtain captured image data of the transmitted light beams. Then, the apparatus main body 500B analyzes the captured image data to detect a transmitted light beam intensity of a transmitted light beam and detects the distance H at which the transmitted light beam passes through the drug solution 24 in the needle-shaped recess 14. By detecting the distance H from each position of the surface 24A with respect to the output transmitted light beam in each needle-shaped recess 14, it is possible to detect the volume of the drug solution 24 that fills each needle-shaped recess 14.

Here, the calculation of the distance H using Expression 1 can be applied to only transmitted light beams of measurement light beams that do not pass through the mold 12, that is, transmitted light beams of measurement light beams that are directly incident to the drug solution 24 in the needle-shaped recess 14 from the communication hole 16. The transmitted light beams of the measurement light beams that pass through the mold 12 and are incident to the drug solution 24 in the needle-shaped recess 14 are influenced by refraction on a boundary surface of an inner surface of the needle-shaped recess 14 and the drug solution 24, or the like. Thus, the transmitted light beam intensity of each transmitted light beam becomes a value subjected to an influence other than the light absorption in the drug solution 24 (water 19), and thus, the distance H cannot be correctly calculated by Expression 1.

Accordingly, in the measurement apparatus 500, the imaging unit 500A images the transmitted light beams of the mold 12 using two kinds of measurement light beams having different wavelength bands to obtain two kinds of captured image data, and the apparatus main body 500B analyzes the two kinds of captured image data to detect the distance H of each transmitted light beam output from each position of the surface 24A in each needle-shaped recess 14.

<Configuration of Imaging Unit>

Figure 25:
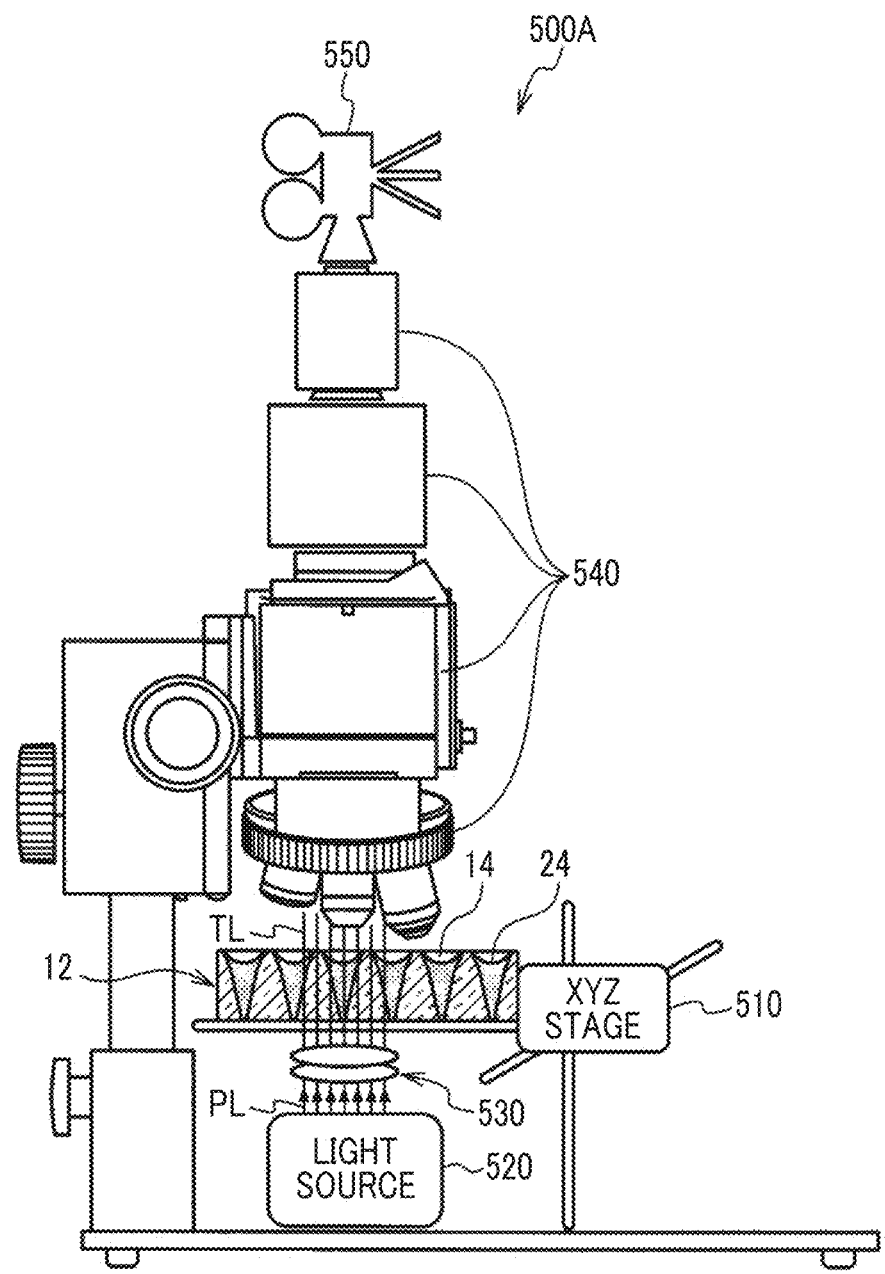
FIG. 25 is a side view of an imaging unit indicating an example of a specific configuration of the imaging unit shown in FIG. 21.

FIG. 25 is a side view of the imaging unit 500A indicating an example of a specific configuration of the imaging unit 500A shown in FIG. 21.

As shown in FIGS. 21 and 25, the imaging unit 500A includes an XYZ stage 510, a light source 520, a wavelength selection filter 530, an imaging optical system 540, and a photodetector 550, as main components.

The XYZ stage 510 is an optically transparent stage having a light transmission feature. The XYZ stage 510 supports the mold 12 in which the needle-shaped recess 14 is filled with the drug solution 24 to be movable in each direction of the X-axis, the Y-axis, and the Z-axis (see FIG. 21). Further, the position of the XYZ stage 510 is adjusted in each direction of the X, Y, and Z axes by a stage driving mechanism (not shown) under the control of an apparatus main body 500B (which will be described later). Thus, the position of the mold 12 may be adjusted in a parallel direction that is parallel to the first surface 12A and the second surface 12B (hereinafter, simply referred to as a parallel direction) and a height direction that is vertical to the first surface 12A and the second surface 12B (hereinafter, simply referred to as a height direction).

The light source 520 corresponds to a first incidence unit and a second incidence unit, and is disposed on the side of the second surface 12B of the mold 12, that is, under the mold 12 (in the figure). The light source 520 emits measurement light beams PL (corresponding to a first measurement light beam and a second measurement light beam) toward the second surface 12B of the mold 12 after being filled with the drug solution 24. The measurement light beams PL are parallel light beams orthogonal (including approximately orthogonal) to the second surface 12B (first surface 12A). It is preferable that the measurement light beams PL are light beams of a wavelength band at which an absorption factor of light in the above-mentioned water 19 becomes high, that is, infrared light beams (IR light beams).

The wavelength selection filter 530 is disposed between the light source 520 and the XYZ stage 510. The wavelength selection filter 530 includes a first interference filter 530A corresponding to a first filter and a second interference filter 530B corresponding to a second filter, and one of the interference filters 530A and 530B is selectively inserted into an imaging optical path (corresponding to an optical path of the invention) which is an optical path of each measurement light beam PL. The wavelength selection filter 530 performs switching between the interference filters (the first interference filter 530A and the second interference filter 530) to be inserted into the imaging optical path under the control of the apparatus main body 500B.

In the figure, for ease of illustration, a state where the interference filters 530A and 530B are inserted into the imaging optical path is shown. Further, the imaging optical path refers to an optical path until the measurement light beams PL output from the light source 520 reach the photodetector 550 (which will be described later).

As the first interference filter 530A and the second interference filter 530B, for example, a band pass filter that limits a wavelength band of measurement light beams PL to be transmitted is used. The first interference filter 530A transmits measurement light beams PL of a first wavelength band (hereinafter, simply referred to as a "wavelength band $\lambda 1$") of the invention in which a central wavelength is a wavelength $\lambda 1$, in the measurement light beams PL incident from the light source 520. Thus, the measurement light beams PL of the wavelength band $\lambda 1$ is incident to the second surface 12B of the mold 12. On the other hand, the second interference filter 530B transmits measurement light beams PL of a second wavelength band (hereinafter, simply referred to as a "wavelength band $\lambda 2$") of the invention in which a central wavelength is a wavelength $\lambda 2$ different from the wavelength $\lambda 1$, in the measurement light beams PL incident from the light source 520. Thus, the measurement light beams PL of the wavelength band $\lambda 2$ is incident to the second surface 12B of the mold 12. The intensities of the measurement light beams PL of the wavelength band $\lambda 1$ and the measurement light beams PL of the wavelength band $\lambda 2$ are the same.

By performing switching between the interference filters (the first interference filter 530A and the second interference filter 530B) to be inserted into the imaging optical path in this way, it is possible to allow two kinds (the wavelength band $\lambda 1$ and the wavelength band $\lambda 2$) of measurement light beams PL having different wavelength bands to be incident to the second surface 12B of the mold 12. The measurement light beam PL output from the light source 520 in a state where the first interference filter 530A is inserted into the imaging optical path corresponds to the first measurement light beam, and the measurement light beam PL output from the light source 520 in a state where the second interference filter 530B is inserted into the imaging optical path corresponds to the second measurement light beam.

Selection of the wavelength band $\lambda 1$ and the wavelength band $\lambda 2$ will be described in detail later, but the measurement light beams PL of the wavelength band $\lambda 1$ are light beams of a wavelength band in which an absorption level in the water 19 is lower than that of the measurement light beams PL of the wavelength band $\lambda 2$ (in which a light absorption factor is small). Contrarily, the measurement light beams PL of the wavelength band $\lambda 2$ are light beams of a wavelength band in which the absorption level in the water 19 is higher than that of the measurement light beams PL of the wavelength band $\lambda 1$ (in which the light absorption factor is large).

The imaging optical system 540 is disposed on the side of the first surface 12A of the mold 12, that is, above the mold 12 in the figure. The imaging optical system 540 respectively guides transmitted light beams TL of the measurement light beams PL of the wavelength band $\lambda 1$ that passes through the mold 12 (including the drug solution 24 in the needle-shaped recess 14) and transmitted light beams TL of the measurement light beams PL of the wavelength band $\lambda 2$ up to the photodetector 550, and image-forms the transmitted light beams TL on an imaging surface of the photodetector 550. Here, the transmitted light beam TL of the wavelength band $\lambda 1$ corresponds to the first transmitted light beam of the invention, and the transmitted light beam TL of the wavelength band $\lambda 2$ corresponds to the second transmitted light beam of the invention.

The photodetector 550 is disposed above the imaging optical system 540. The photodetector 550 includes a charge coupled device (CCD) imaging element or a complementary metal oxide semiconductor (CMOS) imaging element. The photodetector 550 is an infrared camera capable of imaging transmitted light beams TL with sensitivity in a wavelength band including the wavelength band $\lambda 1$ and the wavelength band $\lambda 2$, that is, in the infrared band. The photodetector 550 respectively images the transmitted light beams TL of the wavelength band $\lambda 1$ and the transmitted light beams TL of the wavelength band $\lambda 2$ image-formed on an imaging surface of an imaging element using the imaging optical system 540 under the control of the apparatus main body 500B.

Here, since the photodetector 550 images the transmitted light beams TL that pass through the first surface 12A of the mold 12, the imaging is performed in a state where the transmitted light beams TL form a focus on the first surface 12A (hereinafter, referred to as an imaging focus) after passing through the imaging optical system 540. As a method for forming the imaging focus on the first surface 12A, for example, various methods such as a method for forming a mark (which may be an uneven character or symbol) which is a focus adjustment target on the first surface 12A and performing focus adjustment using the mark as a target or a method for performing focus adjustment using wastes, scars, or various scrapes on the first surface 12A as targets may be employed.

In a case where the transmitted light beams TL of the wavelength band $\lambda 1$ are image-formed on an imaging surface of an imaging element after passing through the imaging optical system 540, the photodetector 550 images the transmitted light beams TL of the wavelength band $\lambda 1$ to generate first captured image data D1, and outputs the first captured image data D1 to the apparatus main body 500B. On the other hand, in a case where the transmitted light beams TL of the wavelength band $\lambda 2$ is image-formed on the imaging surface of the imaging element after passing through the imaging optical system 540, the photodetector 550 images the transmitted light beams TL of the wavelength band $\lambda 2$ to generate second captured image data D2, and outputs the second captured image data D2 to the apparatus main body 500B. The first captured image data D1 and the second captured image data D2 have the same size and the same number of pixels.

Figure 26:
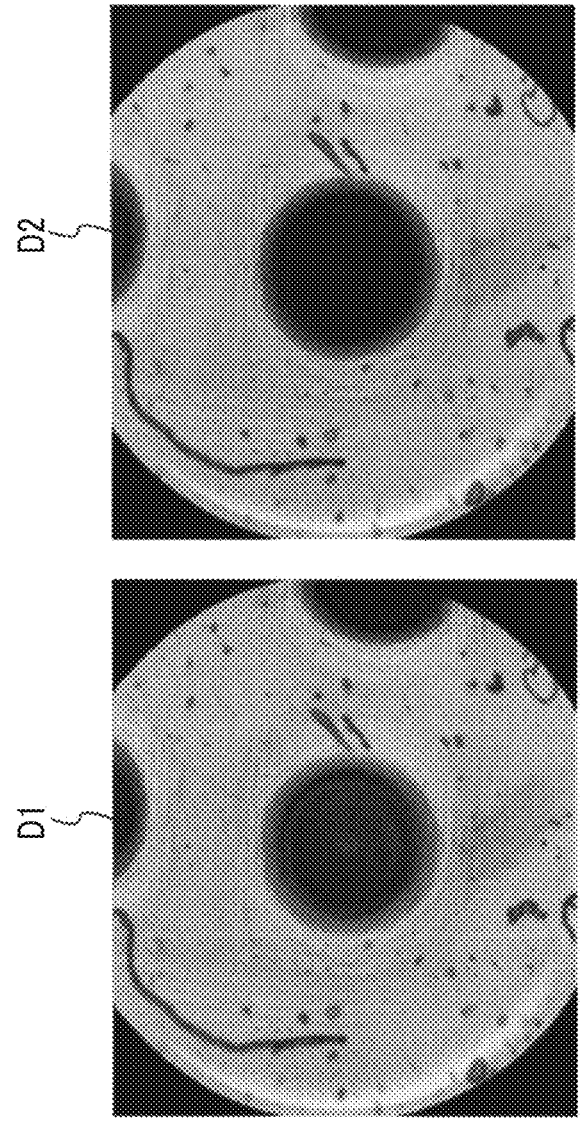
FIG. 26A is a front view of an image based on first captured image data.
FIG. 26B is a front view of an image based on second captured image data.

In this embodiment, the number of needle-shaped recess 14 included in an image based on the first captured image data D1 and an image based on the second captured image data D2 obtained through one-time imaging from the relationship of the resolution of the imaging element of the photodetector 550 is one or several (see FIGS. 26A and 26B). Accordingly, in this embodiment, the transmitted light beams TL of the wavelength band $\lambda 1$ and the transmitted light beams TL of the wavelength band $\lambda 2$ that pass through the drug solution 24 in each needle-shaped recess 14 of the mold 12 are individually imaged by the photodetector 550 while the mold 12 is being moved in a parallel direction (an XY axial direction) in the XYZ stage 510. Thus, the first captured image data D1 and the second captured image data D2 for each needle-shaped recess 14 are output to the apparatus main body 500B from the photodetector 550.

FIG. 26A is a front view of an image based on the first captured image data D1, and FIG. 26B is a front view of an image based on the second captured image data D2. As described above, the measurement light beams PL of the wavelength band $\lambda 1$ represent light beams of a wavelength band that is not easily absorbed by the water 19 in the drug solution 24 compared with the measurement light beams PL of the wavelength band $\lambda 2$, and contrarily, the measurement light beams PL of the wavelength band $\lambda 2$ represent light beams of a wavelength band that is strongly absorbed by the water 19 in the drug solution 24 compared with the measurement light beams PL of the wavelength band $\lambda 1$. As shown in FIGS. 26A and 26B, the image based on the first captured image data D1 becomes an image brighter than the image based on the second captured image data D2, and contrarily, the image based on the second captured image data D2 becomes an image darker than the image based on the first captured image data D1.

Since the transmitted light beams TL that pass through the drug solution 24 in the needle-shaped recess 14 among the transmitted light beams TL of the wavelength band $\lambda 1$ and the transmitted light beams TL of the wavelength band $\lambda 2$ that pass through the mold 12 are absorbed into the water 19 in the drug solution 24, a transmitted light beam intensity thereof becomes lower than the intensity of the transmitted light beams TL that pass through a region other than the drug solution 24 in the mold 12. Thus, in the image based on the first captured image data D1 and the image based on the second captured image data D2, a region corresponding to the drug solution 24 that fills the needle-shaped recess 14 becomes a dark image, and a region other than the above-mentioned region becomes a bright image.

Here, as described above, the transmitted light beams TL that pass through the drug solution 24 through the communication hole 16 are not influenced by refraction or the like on the boundary surface between the inner surface of the needle-shaped recess 14 and the drug solution 24, differently from the transmitted light beams TL that pass through the mold 12 and the drug solution 24. Thus, the transmitted light beam intensity of the transmitted light beams TL that pass through the drug solution 24 through the communication hole 16 becomes higher than the transmitted light beam intensity of the transmitted light beams TL that pass through the mold 12 and the drug solution 24. As a result, in the image based on the first captured image data D1 which is brighter than the image based on the second captured image data D2, a central portion of the dark image corresponding to the drug solution 24, that is, a region corresponding to the communication hole 16 becomes bright (the luminance becomes high).

In this way, in at least the image based on the first captured image data D1, it is possible to recognize the region corresponding to the communication hole 16. Thus, on the image based on the first captured image data D1, position matching between the center of the imaging element of the photodetector 550 and the communication hole 16 which is the center of the needle-shaped recess 14 becomes possible.

Since the measurement light beams PL are not absorbed in a region (silicone rubber region) other than the drug solution 24 in the needle-shaped recess 14 in the mold 12, in the image based on the first captured image data D1 and the image based on the second captured image data D2, the brightness (luminance) of the region other than the drug solution 24 is uniform or approximately uniform.

Figure 27:
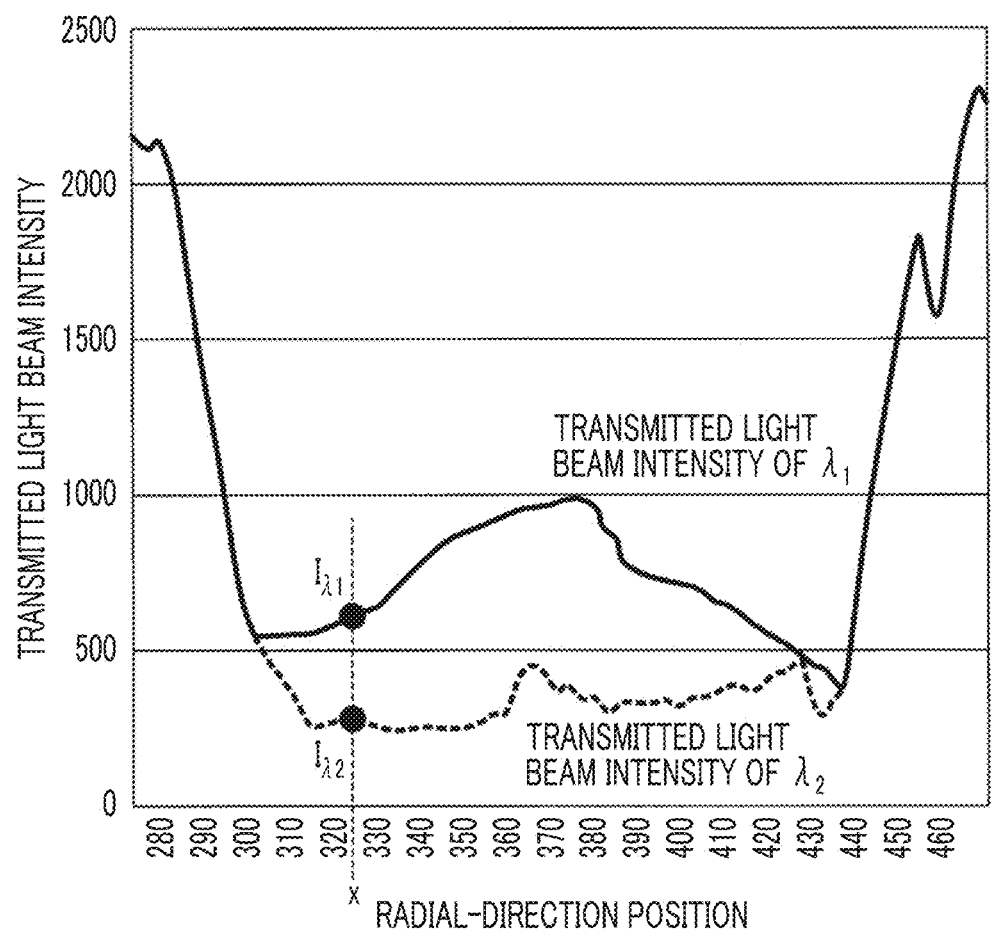
FIG. 27 is a graph showing a distribution of a transmitted light beam intensity $I_{\lambda 1}$ of a transmitted light beam of a wavelength band $\lambda 1$ and a distribution of a transmitted light beam intensity $I_{\lambda 2}$ of a transmitted light beam of a wavelength band $\lambda 2$, corresponding to one needle-shaped recess.

Then, a principle of this embodiment will be described. FIG. 27 is a graph showing a distribution (indicated by a solid line in the figure) of a transmitted light beam intensity $I_{\lambda 1}$ of the transmitted light beams TL of the wavelength band $\lambda 1$ corresponding to one needle-shaped recess 14 and a distribution (indicated by a dotted line in the figure) of a transmitted light beam intensity $I_{\lambda 2}$ of the transmitted light beams TL of the wavelength band $\lambda 2$. In the graph, a transverse axis represents a radial position of the needle-shaped recess 14 along an arbitrary axis that passes through the center of the needle-shaped recess 14 in a radial direction (the center of each piece of the imaging data D1 and D2 shown in FIGS. 26A and 26B) and is parallel to the second surface 12B. Accordingly, the center on the transverse axis of the graph corresponds to the position of the above-mentioned communication hole 16. Further, a longitudinal axis of the graph represents the transmitted light beam intensity of the transmitted light beams TL. In FIG. 27, the distribution of the transmitted light beam intensity is one-dimensionally shown, but a distribution of an actual transmitted light beam intensity obtained by analyzing the imaging data D1 and D2 is two-dimensionally shown.

As described above, the transmitted light beams TL of the wavelength band $\lambda 1$ and the transmitted light beams TL of the wavelength band $\lambda 2$ that pass through the drug solution 24 in the needle-shaped recess 14 are absorbed by the water 19 included in the drug solution 24, but the transmitted light beams TL of the wavelength band $\lambda 2$ is more easily absorbed by the water 19 than the transmitted light beams TL of the wavelength band $\lambda 1$. Thus, as shown in FIG. 27, the transmitted light beam intensity $I_{\lambda 2}$ of the transmitted light beams TL of the wavelength band $\lambda 2$ that pass through the drug solution 24 in the needle-shaped recess 14 becomes lower than the transmitted light beam intensity $I_{\lambda 1}$ of the transmitted light beams TL of the wavelength band $\lambda 1$ that pass through the same optical path in the drug solution 24 and is output from the surface 24A. Accordingly, in a case where an arbitrary radial position is represented as "x", the radial position x that satisfies $I_{\lambda 1} > I_{\lambda 2}$ represents a region in which the drug solution 24 is provided in the needle-shaped recess 14. Thus, it is possible to determine the region of the surface 24A of the drug solution 24 in the needle-shaped recess 14 from the distributions of the two-dimensional transmitted light intensities $I_{\lambda 1}$ and $I_{\lambda 2}$ which are obtained by analyzing the imaging data D1 and D2.

On the other hand, in the region (silicone rubber region) other than the drug solution 24 of the mold 12, light absorption in the water 19 included in the drug solution 24 does not occur. Thus, the transmitted light intensities of the transmitted light beams TL of the wavelength band $\lambda 1$ and the wavelength band $\lambda 2$ output from the same position of the mold 12 through the same optical path in the region become approximately the same value. Accordingly, the radial position x that satisfies $I_{\lambda 1} \cong I_{\lambda 2}$ represents the position (silicone rubber region) other than the drug solution 24 of the mold 12.

Figure 28A:
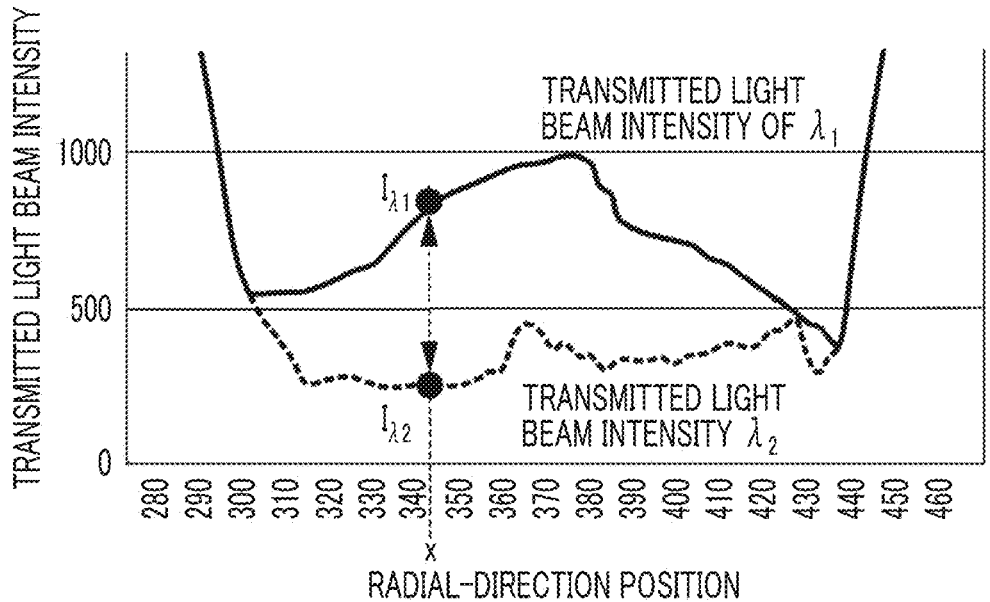
FIG. 28A is an enlarged view in which a part of the graph shown in FIG. 27 is enlarged.
Figure 28B:
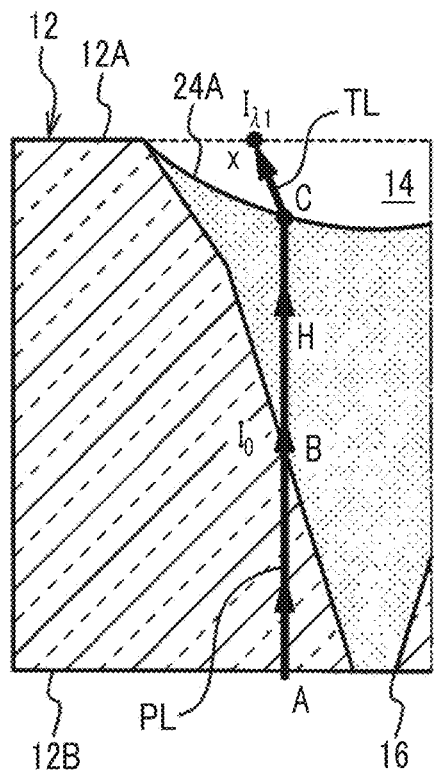
FIG. 28B is a diagram illustrating an optical path, in a mold, of a measurement light beam of the wavelength band $\lambda 1$ incident to a radial position x shown in FIG. 28A.
Figure 28C:
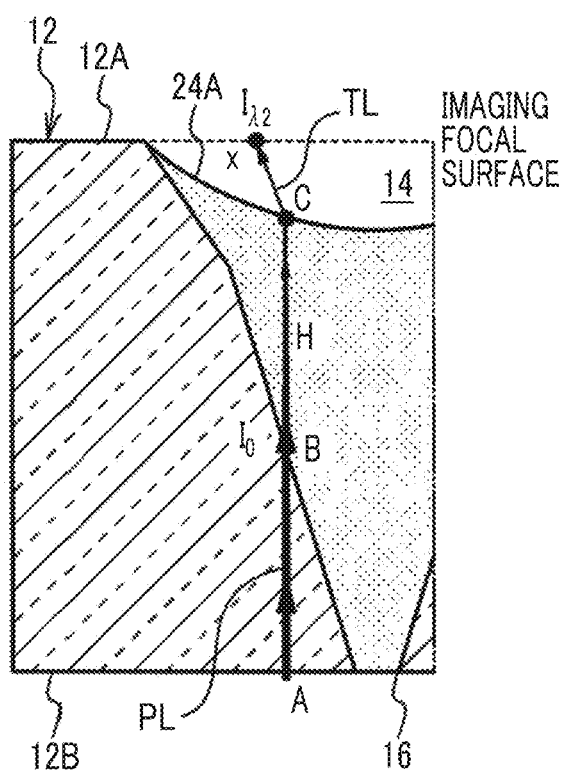
FIG. 28C is a diagram illustrating an optical path, in a mold, of a measurement light beam of the wavelength band $\lambda 2$ incident to the radial position x shown in FIG. 28A.

FIG. 28A is an enlarged view in which a part of the graph shown in FIG. 27 is enlarged. FIG. 28B is a diagram illustrating an optical path, in the mold 12 (including the drug solution 24 in the needle-shaped recess 14), of the measurement light beams PL (the transmitted light beams TL) of the wavelength band $\lambda 1$ incident to the radial position x shown in FIG. 28A. FIG. 28C is a diagram illustrating an optical path in the mold 12 of the measurement light beams PL (the transmitted light beams TL) of the wavelength band $\lambda 2$ incident to the radial position x shown in FIG. 28A. In the figure, "$I_0$" represents the intensity of the measurement light beams PL of each of the wavelength band $\lambda 1$ and the wavelength band $\lambda 2$ incident to the mold 12, and "H" represents a distance of passage of each measurement light beam PL of the wavelength band $\lambda 1$ and the wavelength band $\lambda 2$ through the drug solution 24, which are basically the same as $I_0$ and H in Expression 1.

As shown in FIGS. 28A to 28C, the measurement light beams PL of the wavelength band $\lambda 1$ and the wavelength band $\lambda 2$ incident to the same (including approximately the same) position A on the second surface 12B of the mold 12 go straight through the silicone rubber region of the mold 12 toward the first surface 12A as they are, and are incident to the same position B in the boundary surface between the inner surface of the needle-shaped recess 14 and the drug solution 24.

Here, since a refractive index (about 1.40 to 1.50) of a silicone rubber is a value close to a refractive index (about 1.35 to 1.50) of the drug solution 24, refractive angles of the parallel light beams PL of the wavelength band $\lambda 1$ and the wavelength band $\lambda 2$ which are respectively refracted at the position B become small. Thus, the measurement light beams PL of the wavelength band $\lambda 1$ and the wavelength band $\lambda 2$ which are incident to the position B approximately go straight inside the drug solution 24 toward the first surface 12A, and then, are incident to the same position C in the surface 24A.

The measurement light beams PL of the wavelength band $\lambda 1$ and the wavelength band $\lambda 2$ incident to the position C are refracted on the surface 24A (that is, a boundary surface between the drug solution 24 and air), and are output from the surface 24A as the transmitted light beams TL of the wavelength band $\lambda 1$ and the wavelength band $\lambda 2$, respectively. Further, the transmitted light beams TL of the wavelength band λ1 and the wavelength band λ2 from the position C are incident to the radial position x, respectively, and are imaged by the photodetector 550 that forms a focus on the first surface 12A which is an imaging focal surface.

Here, refractive angles at which the transmitted light beams TL of the wavelength band λ1 and the wavelength band λ2 are refracted on the surface 24A are different from each other, and the distance from the position C to the position of the imaging focal surface is extremely short. Thus, the transmitted light beams TL of the wavelength band λ1 and the wavelength band λ2 output from the position C are incident to the above-mentioned radial position x, that is, approximately the same position in the imaging focal surface.

Accordingly, it can be said that the transmitted light beams TL of the wavelength band λ1 indicating the transmitted light beam intensity $I_{\lambda 1}$ and the transmitted light beams TL of the wavelength band λ2 indicating the transmitted light beam intensity $I_{\lambda 2}$ incident to the radial position x are light beams passing through the same optical path in the mold 12 (the drug solution 24 in the needle-shaped recess 14). That is, the distances H of passages of both the transmitted light beams TL through the drug solution 24 are also the same.

Since light absorption of the mold 12 in the silicone rubber region is not present (or is extremely little), a difference between the transmitted light beam intensity $I_{\lambda 1}$ and the transmitted light beam intensity $I_{\lambda 2}$ at the radial position x is caused only by a difference of light absorptions of both transmitted light beams TL in the water 19 included in the drug solution 24. Thus, as the distances H of passages of both the transmitted light beams TL through the drug solution 24 become longer, the difference between the transmitted light beam intensity $I_{\lambda 1}$ and the transmitted light beam intensity $I_{\lambda 2}$ becomes larger. Accordingly, the transmitted light beam intensity $I_{\lambda 1}$ and the transmitted light beam intensity $I_{\lambda 2}$ represent the distances H of passage of the transmitted light beams TL output from the position C in the surface 24A through the drug solution 24. As a result, by detecting the transmitted light beam intensity $I_{\lambda 1}$ and the transmitted light beam intensity $I_{\lambda 2}$ for each pixel from the captured image data D1 and D2, it is possible to detect the distance H between the position B and the position C at each position in the surface 24A. If the shape information of the needle-shaped recess 14 is already known on the basis of the needle-shaped recess data, the distance H represents a liquid surface height (for example, a liquid surface height with reference to the second surface 12B) at each position of the surface 24A.

As described above, the distance H at each position in the surface 24A can be detected is a case where the light source 520 is disposed on the side of the second surface 12B of the mold 12 and the photodetector 550 is disposed on the side of the first surface 12A, but in a case where a positional relationship between the light source 520 and the photodetector 550 is reversed, the distance between the position B and the position C cannot be detected.

FIG. 29A is a diagram illustrating an optical path in a comparative example in which the measurement light beams PT (transmitted light beams TL) of the wavelength band λ1 passes through the drug solution 24 in the needle-shaped recess 14 of the mold 12 in a case where the positional relationship between the light source 520 and the photodetector 550 is reversed from this embodiment. FIG. 29B is a diagram illustrating an optical path in a comparative example in which the measurement light beams PL (transmitted light beams TL) of the wavelength band λ2 passes through the drug solution 24 in the needle-shaped recess 14 of the mold 12 in a case where the positional relationship between the light source 520 and the photodetector 550 is reversed.

As shown in FIGS. 29A and 29B, the measurement light beams PL of the wavelength band λ1 and the wavelength band λ2 which are vertically incident to the same position $B_x$ on the surface 24A from the same position $A_x$ on the surface 24A are refracted on the surface 24A and are incident to approximately the same position $C_x$ on the inner surface of the needle-shaped recess 14, and then, go straight through the silicone rubber region to be then incident to the radial position x on the second surface 12B (imaging focal surface). Accordingly, in this case, the distance H is a distance between the position $B_x$ and the position $C_x$, and is not a distance between the position $B_x$ as shown in FIGS. 11A and 11B and the position $D_x$ which is vertically disposed under the position B. That is, the positional relationship between the light source 520 and the photodetector 550 is reversed from this embodiment, the distance H does not represent a liquid surface height of the surface 24A at each position. Accordingly, as in this embodiment, it is necessary that the light source 520 is disposed on the side of the second surface 12B of the mold 12, and the photodetector 550 is disposed on the side of the first surface 12A.

Next, the distance H at each portion in the surface 24A for each needle-shaped recess 14 is measured on the basis of detection results (the transmitted light beam intensity $I_{\lambda 1}$ and the transmitted light beam intensity $I_{\lambda 2}$) of two kinds (the wavelength band λ1 and the wavelength band λ2) of transmitted light intensities for each needle-shaped recess 14. Hereinafter, the measurement of the distance H will be described.

The transmitted light beam intensity $I_{\lambda 1}$ and the transmitted light beam intensity $I_{\lambda 2}$ are respectively expressed as the following expressions in a case where the intensities of the measurement light beams PL of the wavelength band λ1 and the wavelength band λ2 are represented as "$I_0$", attenuation factors of light intensities when the measurement light beams PL of the wavelength band λ1 and the wavelength band λ2 are respectively refracted on the surface 24A are represented as "η", a light absorption coefficient of the water 19 with respect to light of the wavelength band λ1 is represented as "$\alpha_{\lambda 1}$", and a light absorption coefficient of the water 19 with respect to light of the wavelength band λ2 is represented as "$\alpha_{\lambda 2}$".

$$I_{\lambda 1} = \eta \cdot I_0 \cdot 10^{-\alpha_{\lambda 1} H} \qquad [\text{Expression 3}]$$

$$I_{\lambda 2} = \eta \cdot I_0 \cdot 10^{-\alpha_{\lambda 2} H} \qquad [\text{Expression 4}]$$

[Expression 4] is obtained from [Expression 2] and [Expression 3], and [Expression 5] indicating a relationship between the "transmitted light beam intensity $I_{\lambda 1}$ and the transmitted light beam intensity $I_{\lambda 2}$" and the "distance H" is obtained from [Expression 4].

$$\frac{I_{\lambda 2}}{I_{\lambda 1}} = 10^{-(\alpha_{\lambda 2} - \alpha_{\lambda 1})H} \qquad [\text{Expression 5}]$$

-continued $$H = \frac{\log_{10}I_{\lambda_1} - \log_{10}I_{\lambda_2}}{\alpha_{\lambda_2} - \alpha_{\lambda_1}} \quad \text{[Expression 6]}$$

By respectively substituting the transmitted light beam intensity $I_{\lambda_1}$ and the transmitted light beam intensity $I_{\lambda_2}$, and the light absorption coefficient $\alpha_{\lambda_1}$ and the light absorption coefficient $\alpha_{\lambda_2}$ in [Expression 5], it is possible to calculate the distance H at one point (position C) in the surface 24A. A method for determining the light absorption coefficient $\alpha_{\lambda_1}$ and the light absorption coefficient $\alpha_{\lambda_2}$ will be described later.

For example, by sequentially substituting the transmitted light beam intensity $I_{\lambda_1}$ and the transmitted light beam intensity $I_{\lambda_2}$ for each pixel in [Expression 5] from an upper left pixel of each of the imaging data D1 and D2 corresponding to a first needle-shaped recess 14 using a raster scanning method, it is possible to detect the distance H for each pixel. Since the transmitted light beam intensity $I_{\lambda_1}$ is larger than the transmitted light beam intensity $I_{\lambda_2}$ in pixels in a region corresponding to the surface 24A of each of the imaging data D1 and D2, the distance H becomes larger than 0. On the other hand, in pixels in a silicone rubber region other than the surface 24A of each of the imaging data D1 and D2, since the transmitted light beam intensity $I_{\lambda_1}$ is approximately equal to the transmitted light beam intensity $I_{\lambda_2}$, it is detected that the distance H is approximately equal to 0. Accordingly, the detection result of the distance H for each pixel of each of the imaging data D1 and D2 represents the distance H at each position of the surface 24A in the first needle-shaped recess 14.

Similarly, the distance H for each pixel is measured with respect to each of the imaging data D1 and D2 corresponding to a second needle-shaped recess 14 and thereafter. Thus, it is possible to measure the distance H at each position in the surface 24A for each needle-shaped recess 14.

With respect to the three-dimensional shape of the drug solution 24, on the basis of the detection results of distances H of all pixels for each needle-shaped recess 14 and the needle-shaped recess data, the three-dimensional shape of the surface 24A for each needle-shaped recess 14 is calculated. In consideration of a smooth shape of the inner surface of the needle-shaped recess 14 and a surface tension of the surface 24A, the distance between the radial position x and the position C shown in FIGS. 28B and 28C extremely becomes small. Thus, as described above, if the shape information of the needle-shaped recess 14 is already known on the basis of the needle-shaped recess data, the liquid surface height (for example, the liquid surface height with reference to the second surface 12B) at each position of the surface 24A for each needle-shaped recess 14 is calculated from the detection results of the distances H of all the pixels for each needle-shaped recess 14. Accordingly, the three-dimensional shape calculation unit 61 can calculate the three-dimensional shape of the surface 24A for each needle-shaped recess 14 on the basis of the detection results of the distances H for each needle-shaped recess 14 and the needle-shaped recess data.

Figure 30:
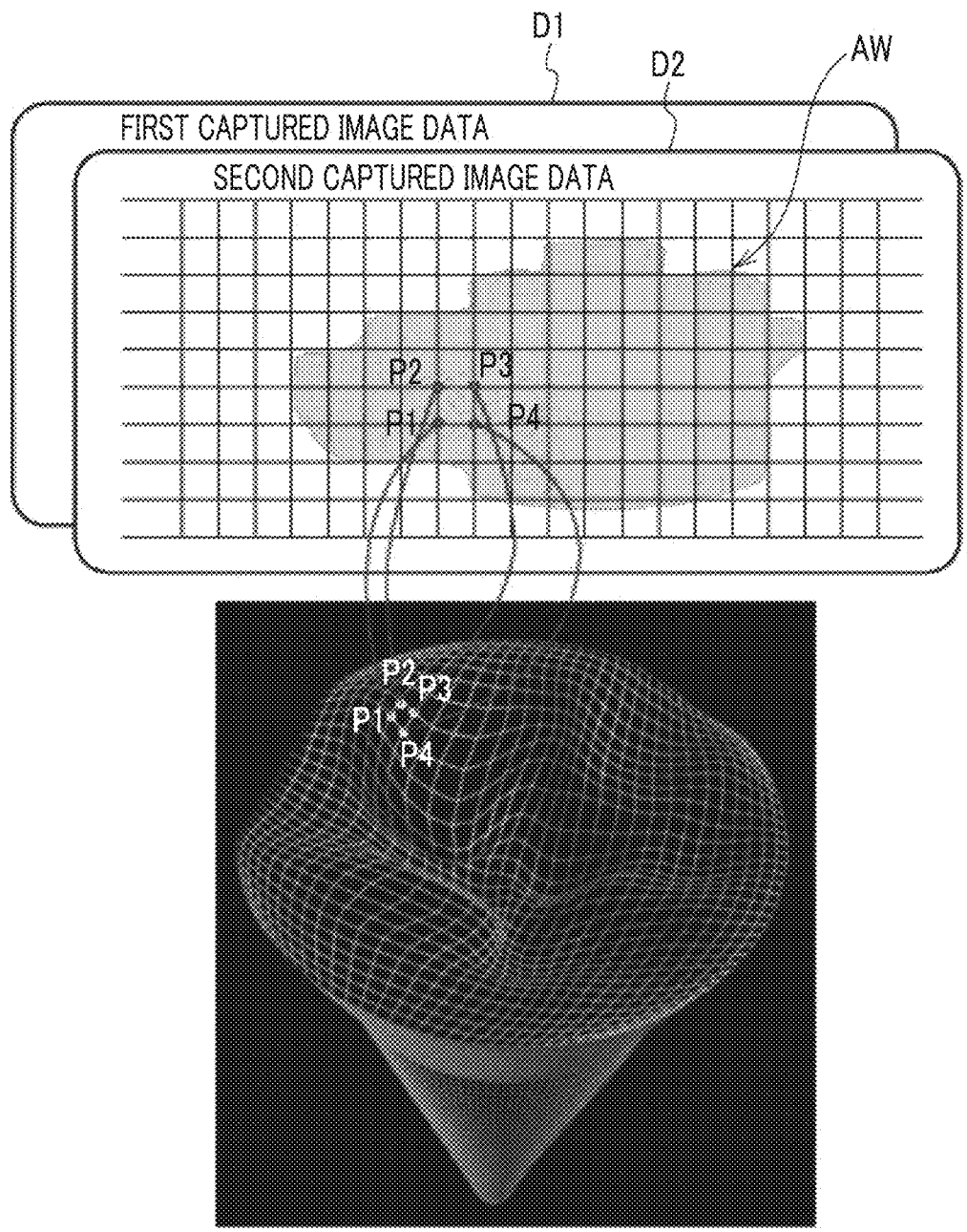
FIG. 30 is a diagram illustrating an example of a calculation process of a three-dimensional shape of a liquid surface in a three-dimensional shape calculation unit.

FIG. 30 is a diagram illustrating an example of a three-dimensional shape calculation process of the surface 24A. In FIG. 30, a region AW in each of the imaging data D1 and D2 is a region where "the transmitted light beam intensity $I_{\lambda_1}$ is larger than the transmitted light beam intensity $I_{\lambda_2}$" is satisfied, that is, a region corresponding to the surface 24A of the needle-shaped recess 14.

First, coordinates of each pixel that is present in the region AW of each of the imaging data D1 and D2 corresponding to the first needle-shaped recess 14 are registered in a peak list of a mesh shown in the figure. Further, a liquid surface height (for example, a distance between the position A and the position C shown in FIGS. 28B and 28C) of each pixel in the region AW is calculated on the basis of the shape information of the needle-shaped recess 14 based on the needle-shaped recess data and the detection results of the distances H of all the pixels.

Then, with respect to peaks (three points: p2, p3, and p4 in the figure) adjacent to an arbitrary peak (p1 in the figure) of the mesh, a triangle formed by the three points is registered in the mesh. By repeatedly executing the registration process for each mesh peak, the three-dimensional shape of the surface 24A in the first needle-shaped recess 14 is calculated.

Similarly, the three-dimensional shape of the surface 24A of the second needle-shaped recess 14 and thereafter is also calculated. Since the shape of each needle-shaped recess 14 is already known, the entire three-dimensional shape of the drug solution 24 that fill each needle-shaped recess 14 can also be calculated on the basis of the three-dimensional shape of the surface 24A of each needle-shaped recess 14.

[Selection of First Interference Filter (Wavelength Band λ1) and Second Interference Filter (Wavelength Band λ2)]

Next, selection of the first interference filter 530A (the wavelength band λ1) and the second interference filter 530B (wavelength band λ2) will be described. As shown in FIG. 5, the water 19 has a high light absorbance with respect to light having a wavelength of about 1450 nm and light having a wavelength of about 1945 nm, in which the light absorbance with respect to the light having the wavelength of about 1945 nm is higher than the light absorbance with respect to the light having the wavelength of about 1450 nm. Thus, in this embodiment, a wavelength band in which 1450 nm is a central wavelength is defined as $\lambda_{low}$, and a wavelength band in which 1945 nm is a central wavelength is defined as $\lambda_{high}$.

In the measurement apparatus 500 that measures the volume of the drug solution 24 on the basis of the difference between the transmitted light beam intensity and transmitted light beam intensity $I\lambda_2$, in order to increase measurement accuracy, it is preferable to appropriately select the first interference filter 530A (wavelength band λ1) and the second interference filter 530B (wavelength band λ2) according to the volume of the drug solution 24 that fills the needle-shaped recess 14.

Specifically, in this embodiment, in a case where a mold 12 (corresponding to a first mold in the invention) having a thickness (a thickness in a vertical direction with respect to the first surface 12A and the second surface 12B) larger than a predetermined reference value is a measurement target as the mold 12, that is, in a case where the volume of the drug solution 24 that fills one needle-shaped recess 14 is large, a wavelength band $\lambda_{low}$ at which light absorption in the water 19 is low is selected as the wavelength band λ2 of the second interference filter 530B. On the other hand, in a case where a mold 12 (corresponding to a second mold in the invention) of which a thickness is equal to or smaller than the predetermined reference value) is a measurement target as the mold 12, that is, in a case where the volume of the drug solution 24 that fills one needle-shaped recess 14 is small, a wavelength band $\lambda_{high}$ at which light absorption in the water 19 is high is selected as the wavelength band λ2 of the second interference filter 530B.

Then, the wavelength band λ1 of the first interference filter 530A suitable for the wavelength band λ2 of the selected second interference filter 530B is performed.

Figure 31:
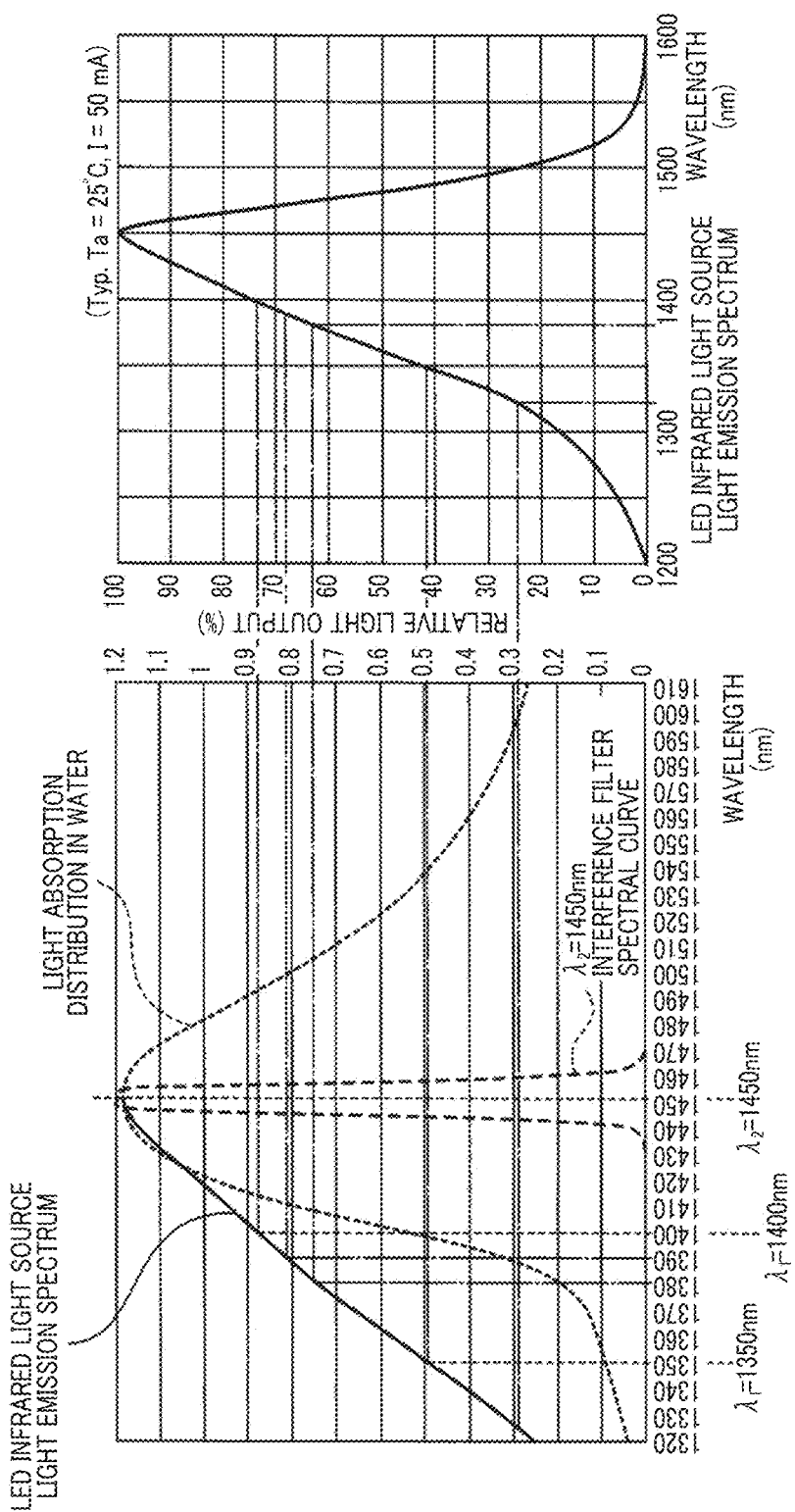
FIG. 31A is a diagram illustrating a method for selecting a wavelength band $\lambda 1$ of a first interference filter in a case where an LED infrared light source which is commercially available is used as a light source of a wavelength band $\lambda 2 = \lambda_{low}$.
FIG. 31B is a graph showing an emission spectrum of the LED infrared light source used as the light source.

FIG. 31A is a diagram illustrating a method for selecting the wavelength band λ1 of the first interference filter 530A in a case where an LED infrared light source which is commercially available is used as the light source 520 of the wavelength band λ2=$λ_{low}$. FIG. 31B is a graph showing an emission spectrum of the LED infrared light source used as the light source 520. As shown in FIGS. 31A and 31B, in a case where the wavelength band λ2 is $λ_{low}$, 1350 nm or 1400 nm is selected as a central wavelength of the wavelength band λ1 in consideration of emission efficiency of the light source 520 and light absorption in the water 19.

[Determination of Light Absorption Coefficient $α_{λ1}$ and Light Absorption Coefficient $α_{λ2}$]

Next, determination of the light absorption coefficient $α_{λ1}$ and the light absorption coefficient $α_{λ2}$ will be described. If the measurement light beams PL incident to the mold 12 are single-wavelength light beams, the light absorption coefficient $α_{λ1}$ and the light absorption coefficient $α_{λ2}$ may be simply determined on the basis of the graph shown in FIG. 5. However, since bandwidths of the first interference filter 530A and the second interference filter 530B (band pass filter) are uniform, the measurement light beams PL that pass through the first interference filter 530A and the second interference filter 530B have a plurality of wavelengths instead of a single wavelength. According to the light absorption distribution in the water 19 shown in FIG. 23, if the wavelength of the light (measurement light beams PL) is changed, the light absorption coefficient is also changed. Accordingly, with respect to light having a uniform width (measurement light beams PL), it is preferable to totally consider full widths at half maximum of the first interference filter 530A and the second interference filter 530B, or an emission spectrum of the light source 520, and a light absorption distribution in the water 19 for the light absorption coefficient.

Specifically, a central wavelength of the interference filter (the first interference filter 530A and the second interference filter 530B) is represented to as "$λ_f$", and the above-mentioned full width at a half maximum (FWHM) is represented to as "fwhm". A spectral feature of light (measurement light beams PL) that passes through the interference filter is an integration of a spectral feature of the light source 520 and a spectral feature of the interference filter, the light that passes through the interference filter is defined as light output from a "light source with a filter" corresponding to a light source that outputs light of a central wavelength band λf and a full width at a half minimum FWHM=fmwh.

Figure 32:
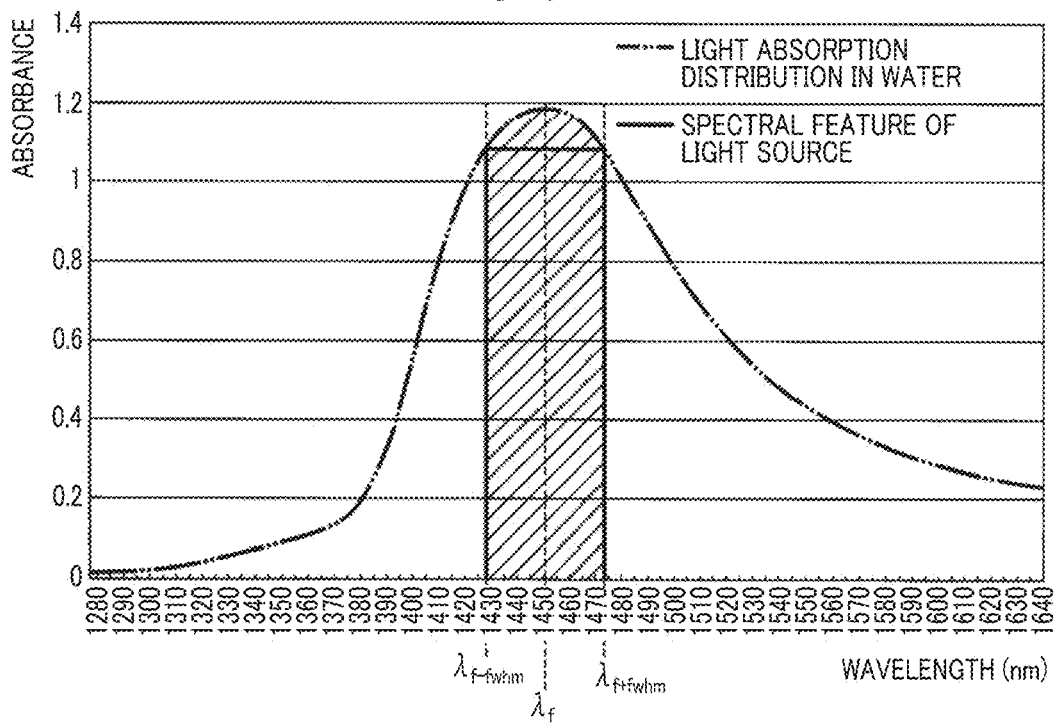
FIG. 32 is a diagram illustrating calculation of a light absorption coefficient.

FIG. 32 is a diagram illustrating the calculation of a light absorption coefficient in a case where a spectrum of the "light source with the filter" is uniform between "λf−fwhm" and "λf+fwhm". In FIG. 32, a two-dot chain line represents a light absorption distribution in the water 19, a solid line represents a spectral characteristic of the light source 520 with a filter of a central wavelength band λf, and a full width at a half minimum of FWHM=fwhm. With respect to light (measurement light beams PL) output from the light source 520, the light absorption coefficient $α_f$ of the water 19 is calculated by the following expression.

$$α_{λ_f} = \frac{\int_{λ_f-fwhm}^{λ_f+fwhm} W(λ)dλ}{2 \times fwhm}$$ [Expression 7]

In [Expression 7], W(λ) represents a light absorption distribution in the water 19. The light absorption coefficient $α_f$ is a value obtained by dividing the area of an oblique line portion in FIG. 15D by "2×fwhm".

Figure 33:
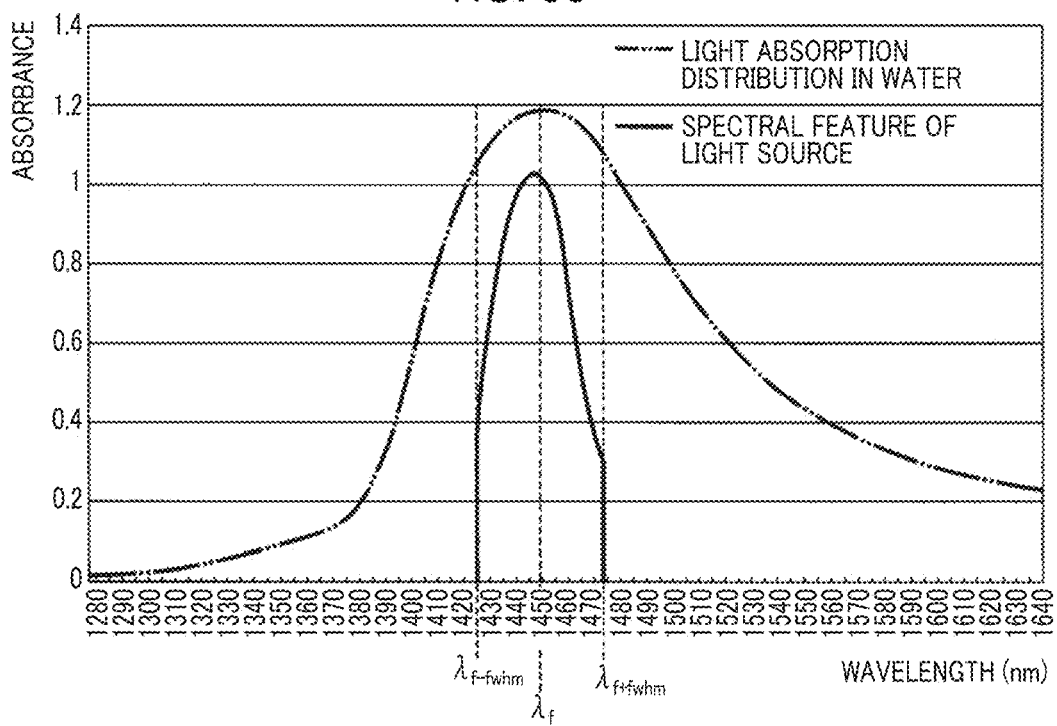
FIG. 33 is a diagram illustrating calculation of a light absorption coefficient different from that of FIGS. 12A and 12B.

FIG. 33 is a diagram illustrating the calculation of a light absorption coefficient in a case where a spectrum of the "light source with the filter" is not uniform between "$λ_f$−fwhm" and "$λ_f$+fwhm". In FIG. 33, a two-dot chain line represents a light absorption distribution in the water 19, a solid line represents a spectral feature of the light source 520 (with a filter) of a central wavelength band of λf and a full width at a half minimum of FWHM=fwhm. With respect to the light (measurement light beams PL) output from the light source 520, the light absorption coefficient $α_f$ of the water 19 is calculated by the following expression.

$$α_{λ_f} = \frac{\int_{λ_f-fwhm}^{λ_f+fwhm} W(λ)F(λ)dλ}{\int_{λ_f-fwhm}^{λ_f+fwhm} F(λ)dλ}$$ [Expression 8]

In [Expression 8], W(λ) represents a light absorption distribution in the water 19, and F(λ) represents a spectral feature of a light source.

As described above, in this embodiment, the light absorption coefficient $α_{λ1}$ and the light absorption coefficient $α_{λ2}$ are determined using [Expression 7] or [Expression 8].

Figure 34:
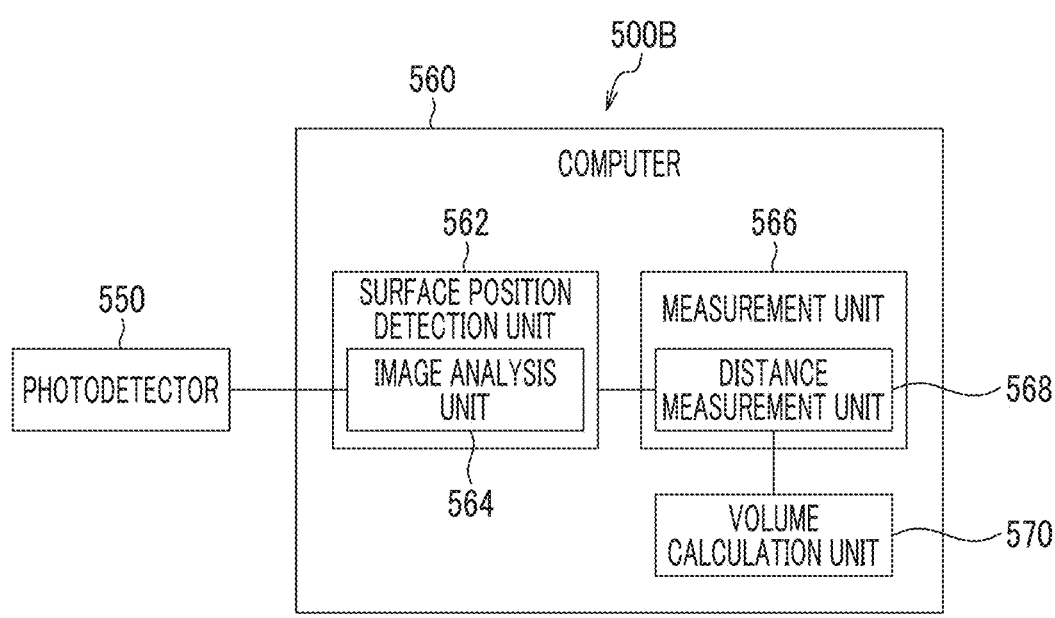
FIG. 34 is a block diagram of an apparatus main body.

FIG. 34 is a block diagram of the apparatus main body 500B according to this embodiment. The apparatus main body 500B includes a computer 560, a surface position detection unit 562, a measurement unit 566, and a volume calculation unit 570.

The surface position detection unit 562 acquires first captured image data D1 and second captured image data D2 from the photodetector 550. When the photodetector 550 acquires the first captured image data D1, position matching of the center of an imaging element of the photodetector 550 and the communication hole 16 of the first needle-shaped recess 14 is performed. At this position, the second captured image data D2 is acquired.

The surface position detection unit 562 includes an image analysis unit 564. The image analysis unit 564 analyzes the respective imaging data D1 and D2 for each needle-shaped recess 14 acquired from the photodetector 550, and detects transmitted light intensities of the transmitted light beams TL of the wavelength band λ1 and the wavelength band λ2 that pass through the drug solution 24 in the needle-shaped recess 14 and output from each position of the surface 24A to each needle-shaped recess 14. The transmitted light beam intensity of each transmitted light beam TL can be detected based on a luminance value (luminance information) of each pixel of the imaging data D1 and D2, for example. Further, the surface position detection unit 562 outputs detection results of two kinds (the wavelength band λ1 and the wavelength band λ2) of transmitted light intensities for each needle-shaped recess 14, detected by the image analysis unit 564, to the measurement unit 566.

The measurement unit 566 includes a distance measurement unit 568. The distance H at each position of the surface 24A for each needle-shaped recess 14 is measured according to the above-mentioned method on the basis of the detection results of two kinds (the wavelength band λ1 and the wavelength band λ2) of transmitted light intensities for each needle-shaped recess 14 (the transmitted light beam intensity $I_{\lambda 1}$ and the transmitted light beam intensity $I_{\lambda 2}$) in the distance measurement unit 568.

The measurement apparatus 500 including the surface position detection unit 562 that includes the image analysis unit 564 forms the second detection unit 103, and the measurement unit 566 that includes the distance measurement unit 568 forms the second measurement unit 104. The volume calculation unit 570 forms the calculation unit 105.

The volume calculation unit 570 calculates the volume of the drug solution 24 that fills the needle-shaped recess 14 for each needle-shaped recess 14 on the basis of the detection results of the distances of all the pixels for each needle-shaped recess 14. Specifically, the volume calculation unit 570 adds up the detection results of the distances H of all the pixels corresponding to the first needle-shaped recess 14. As described above, since the distances H are approximately 0 at the pixels in the silicone rubber region other than the surface 24A, addition results of the distances H for all the pixels are obtained by adding up the distances H at the respective positions on the surface 24A in the first needle-shaped recess 14, and corresponds to the volume V1 of the drug solution 24 that fills the first needle-shaped recess 14. Thus, the volume of the drug solution 24 in the first needle-shaped recess 14 is calculated.

Similarly, the volume calculation unit 570 calculates the volume of the drug solution 24 in the second needle-shaped recess 14 and thereafter. Thus, it is possible to calculate the volume of the drug solution 24 that fills all the needle-shaped recesses 14. Further, on the basis of the calculation result, the volume calculation unit 60 can calculate the volume of the drug solution 24 that fills one mold 12 (all the needle-shaped recesses 14). In a case where the volume of the drug solution 24 in an i-th needle-shaped recess 14 is represented as $V_i$, the entire volume $V_{total}$ of the drug solution 24 that fills one mold 12 is expressed as follows.

$$V_{total} = \sum_{i=1}^{N} V_i \qquad \text{[Expression 9]}$$

The volume of the drug solution 24 for each needle-shaped recess 14 calculated by the volume calculation unit 570 and the entire volume of the drug solution 24 in the mold 12 are stored in a storage unit (not shown) as a measurement result of the volume of the drug solution 24.

Information of the three-dimensional shape of the needle-shaped recess 14 of the mold 12 calculated from the confocal microscope 110 shown in FIG. 6 is stored in the volume calculation unit 570. The volume calculation unit 570 may execute a calculation process of the three-dimensional shape in FIG. 30 on the basis of the shape data (distance H) of the drug solution 24 and the three-dimensional shape (shape data) of the needle-shaped recess 14, to thereby create the three-dimensional shape of the drug solution 24.

Effects of the Embodiment

As described above, in the measurement apparatus 500 of this embodiment, since the volume of the drug solution 24 in each needle-shaped recess 14 is measured on the basis of the two kinds of imaging data D1 and D2 obtained by individually imaging two kinds of transmitted light beams TL having different wavelength bands that pass through the mold 12 (the drug solution 24 in the needle-shaped recess 14), it is possible to measure the volume of the drug solution 24 for each needle-shaped recess 14 of the mold 12 with high accuracy in a non-destructive manner. Further, the measurement apparatus 500 can perform measurement without changing a basic measurement method even if the kind of the drug 26 included in the drug solution 24 is changed.

Another Embodiment

<Another Embodiment of the Imaging Unit>
In the imaging unit 500A of the above-mentioned embodiment, the wavelength selection filter 530 is disposed between the light source 520 and the second surface 12B of the mold 12, but the position at which the wavelength selection filter 530 is disposed is not particularly limited as long as it is disposed between the light source 520 and the photodetector 550 (that is, on an imaging optical path).

Figure 35:
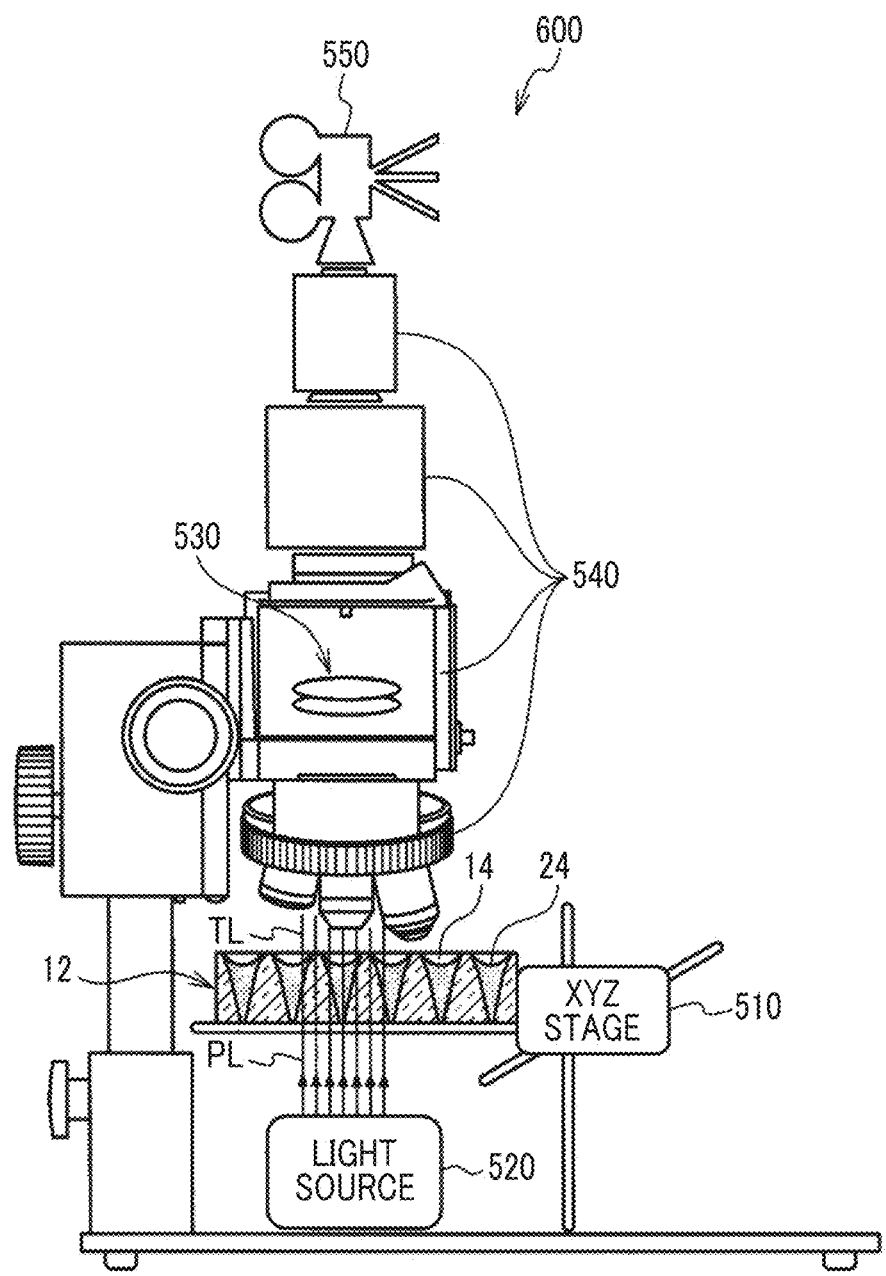
FIG. 35 is a side view of an imaging unit of another embodiment in which a position where a wavelength selection filter is disposed is different from that in the above-described embodiment.

FIG. 35 is a side view of an imaging unit 600 of another embodiment in which a position where the wavelength selection filter 530 is disposed is different from that in the above-described embodiment. As shown in FIG. 35, in the imaging unit 600, the wavelength selection filter 530 is disposed inside the imaging optical system 540 (for example, inside a small vertical illuminating light projection tube), that is, between the light source 520 and the first surface 12A of the mold 12. In this case, similarly, since the transmitted light beams TL of the wavelength band λ1 and the wavelength band λ2 are respectively incident to the imaging element of the photodetector 550, each of the imaging data D1 and D2 which are the same as in the above-described embodiment is obtained. As a result, similar to the above-mentioned embodiment, the volume of the drug solution 24 in each needle-shaped recess 14 may be measured.

<Another Embodiment of the Measurement Apparatus>
In the above-mentioned embodiment, the needle-shaped recess 14 of the mold 12 are imaged one by one from the relationship of the resolution of the imaging element of the photodetector 550, but all the needle-shaped recesses 14 in one mold 12 may be simultaneously imaged in a case where the resolution of the imaging element is sufficiently high.

Figure 36:
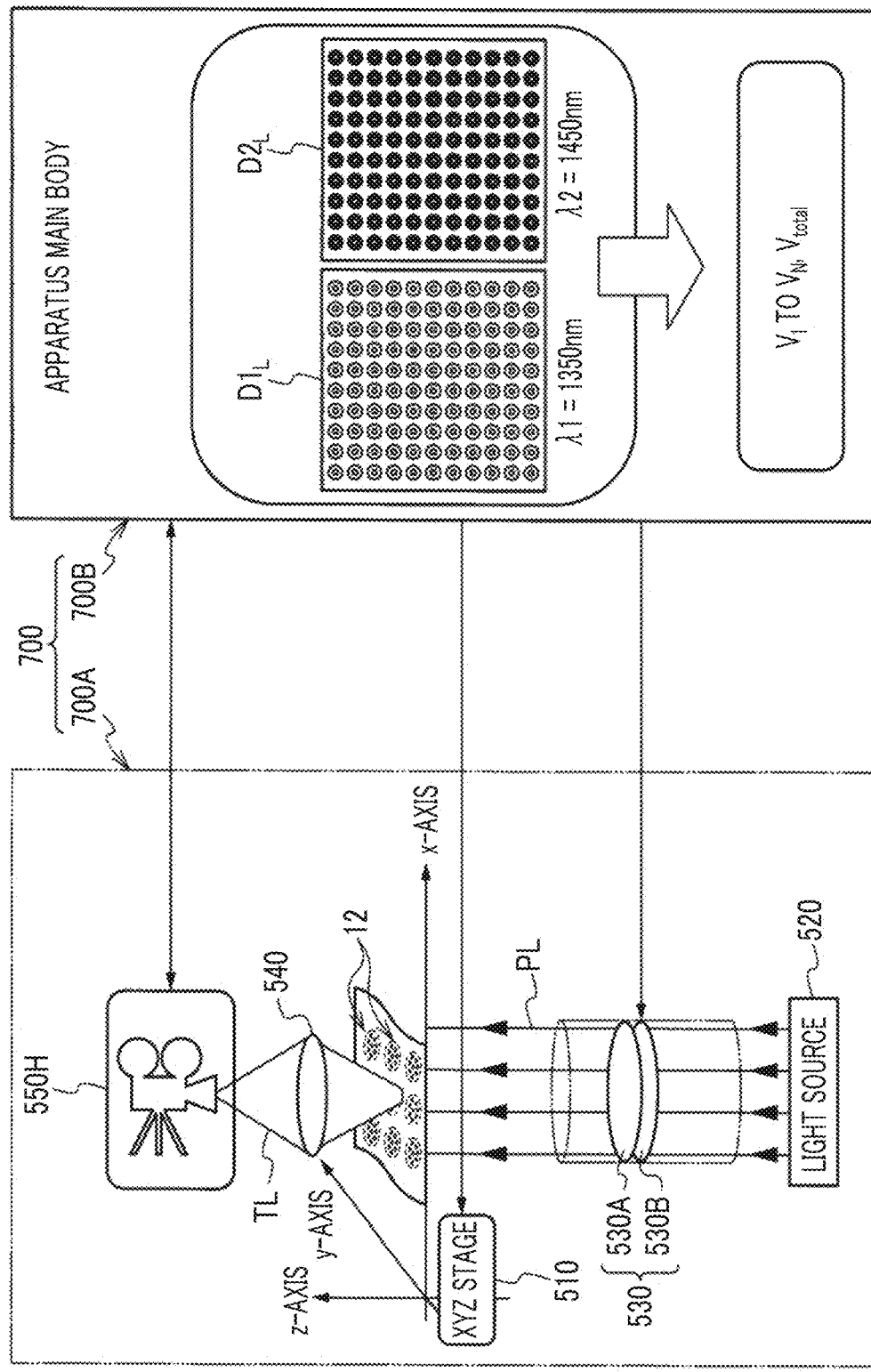
FIG. 36 is a schematic diagram of a measurement apparatus of another embodiment in which all needle-shaped recesses in one mold are simultaneously imaged and each piece of captured image data obtained through the imaging is analyzed to calculate the volume of a drug solution in each needle-shaped recess.

FIG. 36 is a schematic diagram of a measurement apparatus 700 of another embodiment in which all the needle-shaped recesses 14 in one mold 12 are simultaneously imaged, and each of the imaging data D1 and D2 obtained through the imaging is analyzed to calculate the volume of the drug solution 24 in each needle-shaped recess 14.

As shown in FIG. 36, the measurement apparatus 700 has basically the same configuration as that of the measurement apparatus 500 of the above-described embodiment except that all the needle-shaped recesses 14 in one mold 12 are simultaneously imaged and the first captured image data $D1_L$ and the second captured image data $D2_L$ obtained through the imaging are analyzed. Thus, the same reference numerals are given to components having the same functions and configurations as those of the above-described embodiment, description thereof will not be repeated.

The measurement apparatus 700 includes an imaging unit 700A and an apparatus main body 700B. The imaging unit 700A has basically the same configuration as that of the imaging unit 500A of the embodiment except that a plurality of molds 12 are set on an XYZ stage 510 and a photodetector 550H instead of the photodetector 550 of the above-described embodiment is provided. Here, in the imaging unit 700A, measurement light beams PL are incident to an entire surface (including an approximately entire surface) of the second surface 12B of one mold 12, transmitted light beams TL are output from the entire surface of the first surface 12A, and the transmitted light beams TL are incident to an imaging surface of an imaging element of the photodetector 550H through the imaging optical system 540.

The photodetector 550H includes a high-resolution imaging element which is capable of simultaneously imaging all the needle-shaped recesses 14 in the mold 12. In a case where the first interference filter 530A is inserted into an optical path by the wavelength selection filter 530, the photodetector 550H images transmitted light beams TL of a wavelength band λ1 to generate first captured image data $D1_L$, and to output the first captured image data $D1_L$ to the apparatus main body 700B. Further, in a case where the second interference filter 530B is inserted into the optical path by the wavelength selection filter 530, the photodetector 550H images transmitted light beams TL of a wavelength band λ2 to generate second captured image data $D2_L$, and to output the second captured image data $D2_L$ to the apparatus main body 700B.

Images of all the needle-shaped recesses 14 in each mold 12 are included in each of an image based on the first captured image data $D1_L$ and an image based on the second captured image data $D2_L$ (hereinafter, simply referred to as imaging data $D1_L$ and $D2_L$).

In the imaging unit 700A, after generation and output of each of the imaging data $D1_L$ and $D2_L$ of one mold 12 are completed, the XYZ stage 510 is driven so that a mold 12 which is the next imaging target is set at a measurement position (imaging optical path). Then, the imaging unit 700A images each of the transmitted light beams TL of the wavelength band λ1 and the transmitted light beams TL of the wavelength band λ2 that pass through the mold 12 which is the next imaging target using the photodetector 550H to generate each of the imaging data $D1_L$ and $D2_L$ and outputs the generated imaging data $D1_L$ and $D2_L$ to the apparatus main body 700B.

Similarly, the imaging unit 700A images the transmitted light beams TL of the wavelength band λ1 and the transmitted light beams TL of the wavelength band λ2 that pass through individual molds 12 on the XYZ stage 510 using the photodetector 550H, and outputs the imaging data $D1_L$ and $D2_L$ for each mold 12 to the apparatus main body 700B.

The apparatus main body 700B analyzes the imaging data $D1_L$ and $D2_L$ for each mold 12 to detect the transmitted light beam intensity $I_{\lambda 1}$ and the transmitted light beam intensity $I_{\lambda 2}$ in each needle-shaped recess 14 for each mold, and then, detects the distances H of all pixels for each needle-shaped recess 14. Then, the apparatus main body 700B calculates volumes $V_1$ to $V_N$ of the drug solution 24 in each needle-shaped recess 14, an entire volume $V_{total}$ of the drug solution 24, and a three-dimensional shape of the surface 24A or the like in each needle-shaped recess 14, respectively, for each mold. Since a method for detecting the transmitted light beam intensity $I_{\lambda 1}$ and the transmitted light beam intensity $I_{\lambda 2}$, a method for detecting the distance H, and a method for calculating the volume of the drug solution 24, and a method for calculating the three-dimensional shape are basically the same methods as those of the above-described embodiment, specific description thereof will not be repeated.

In this way, in the measurement apparatus 700, since all the needle-shaped recesses 14 in the mold 12 are simultaneously imaged, and the volume of the drug solution 24 in each needle-shaped recess 14 is measured on the basis of the imaging data D1L and D2L obtained through the imaging, it is possible to obtain the same effects as in the embodiment, and to achieve high-speed measurement compared with the above-described embodiment. Thus, it is possible to produce an MNA (for example, using a Roll-to-Roll method) with high efficiency when assembling the measurement apparatus 700 in an MNA manufacturing process.

<With Respect to Refraction of Measurement Light Beams at Position B>

In the above-described embodiment, an example in which the measurement light beams PL of the wavelength band λ1 and the wavelength band λ2 incident to the position B go straight inside the drug solution 24 toward the first surface 12A (see FIGS. 11A and 11B) is shown, but the measurement light beams PL of the wavelength band λ1 and the wavelength band λ2 incident to the position B are respectively refracted due to a difference between the refractive index of the silicone rubber and the refractive index of the drug solution 24. A refractive angle of each measurement light beam PL is changed due to the concentration of the drug 26 in the drug solution 24, which is 15° at the maximum. Since the refractive angle is uniform if an inclination angle of the inner surface of the needle-shaped recess 14 is uniform, the distance H may be corrected according to the following expression. In the following expression, "$H_R$" represents a distance after correction, and "θ" represents a refractive angle.

[Expression 10]

$$H_g = H \times \cos\theta$$

<Surface Treatment of the First Surface of Mold>

Figure 37A:
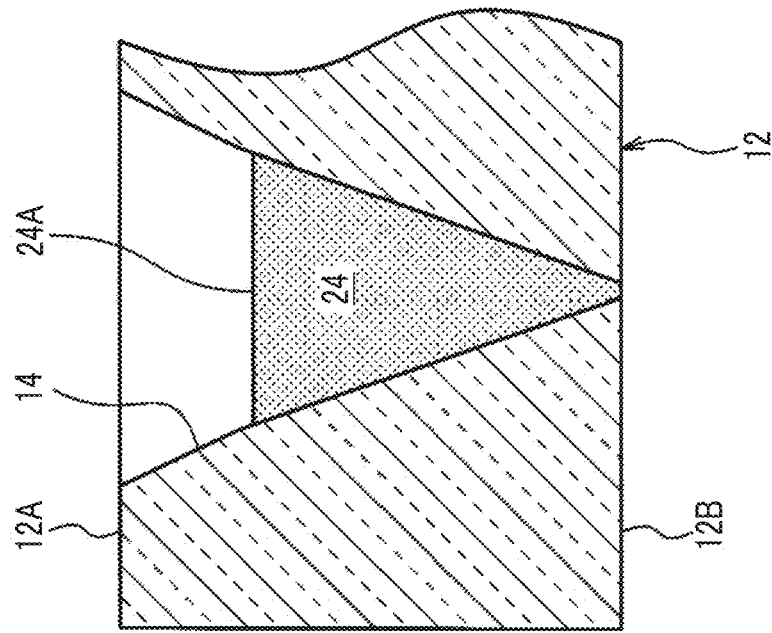
FIG. 37A is a cross-sectional view of a mold for which hydrophilic treatment is not performed with respect to a first surface.
Figure 37B:
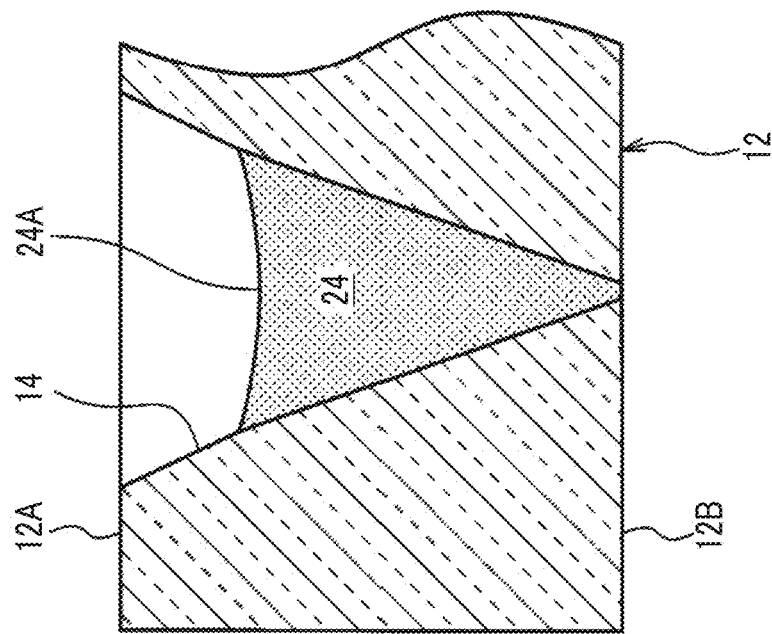
FIG. 37B is a cross-sectional view of a mold for which hydrophilic treatment is performed with respect to the first surface.

In the above-described embodiment, surface treatment is not performed with respect to the first surface 12A of the mold 12, but for example, hydrophilic treatment such as Teflon (registered trademark) treatment may be performed with respect to the first surface 12A in advance before the needle-shaped recess 14 is filled with the drug solution 24. FIG. 37A is a cross-sectional view of the mold 12 for which the hydrophilic treatment is not performed with respect to the first surface 12A, and FIG. 37B is a cross-sectional view of the mold 12 for which the hydrophilic treatment is performed with respect to the first surface 12A.

As shown in FIG. 37A, in the mold 12 for which the hydrophilic treatment is not performed with respect to the first surface 12A, a meniscus occurs on the surface 24A in the needle-shaped recess 14. On the other hand, as shown in FIG. 37B, in the mold 12 for which the hydrophilic treatment is performed with respect to the first surface 12A in advance before the needle-shaped recess 14 is filled with the drug 26, it is possible to prevent the occurrence of a meniscus on the surface 24A of the needle-shaped recess 14, and to form the surface 24A in a planar shape. Thus, it is possible to reduce the refractive angle at the position C of both the transmitted beams TL shown in FIGS. 28B and 28C, and thus, it is possible to reduce an error in the positions C (the radial positions x) of both the transmitted light beams TL. As a result, it is possible to measure the volume of the drug solution 24 or the three-dimensional shape of the surface 24A with high accuracy.

<Calculation of Volume of Drug>

The volume calculation unit 570 of the above-described embodiment calculates the volume of the drug solution 24 in the needle-shaped recess 14, but may calculate the volume of the drug 26 included in the drug solution 24 in the needle-shaped recess 14 on the basis of the calculation result of the volume of the drug solution 24 in the needle-shaped recess 14.

<Fourth Aspect>

Figure 38:
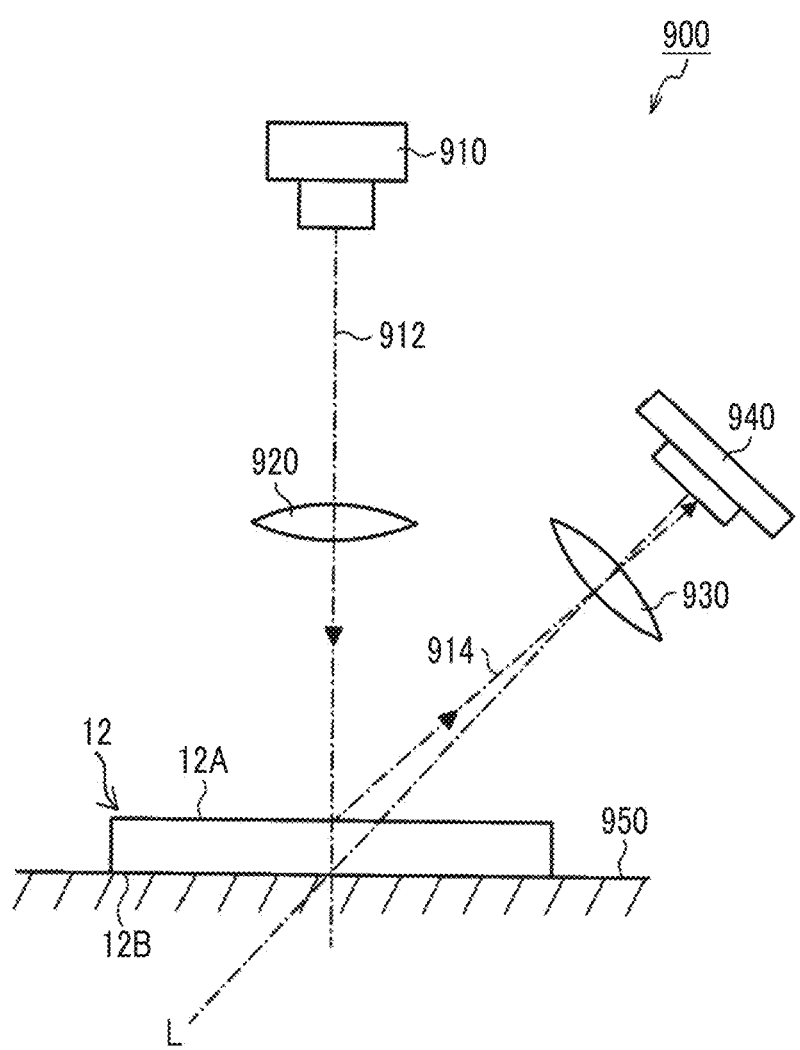
FIG. 38 is a diagram showing a measurement principle based on a triangulation method of a triangulation type displacement meter.

A fourth aspect relates to an aspect in which a triangulation method is applied. FIG. 38 is a diagram showing a measurement principle based on a triangulation method of a triangulation type displacement meter 900.

As shown in FIG. 38, a measurement head unit of the triangulation type displacement meter 900 includes a semiconductor laser 910, a light projection lens 920, a light receiving lens 930, and a light position sensor 940, on the side of a mold 12A. The semiconductor laser 910 outputs laser light 912 in a direction (vertical direction) orthogonal to a horizontal table 950. The laser light 912 output from the semiconductor laser 910 is incident to a measurement point of a surface of a drug solution that fills a mold 12, which is a measurement target surface, as spotlight through the light projection lens 920, and part of the spotlight is reflected at the surface of the drug solution.

Reflected light 914 which is reflected from the measurement point of the surface of the drug solution is image-formed on a light receiving surface of the light position sensor 940 through the light receiving lens 930. A light receiving unit formed by the light receiving lens 930 and the light position sensor 940 in this example is disposed so that an optical axis L of the light receiving unit intersects the laser light 912 on the table 950.

The triangulation type displacement meter 900 reads a light receiving position of the reflected light 914 in the light position sensor 940, and measures the height of the surface of the drug solution based on the surface (a second surface 12B of the mold 12) of the table 950 on the basis of the red light receiving position.

The triangulation type displacement meter 900 may also be applied to a case where the shape of the needle-shaped recess 14 is calculated.

[Relationship Between Drug Solution and Elapsed Time]

Figure 39:
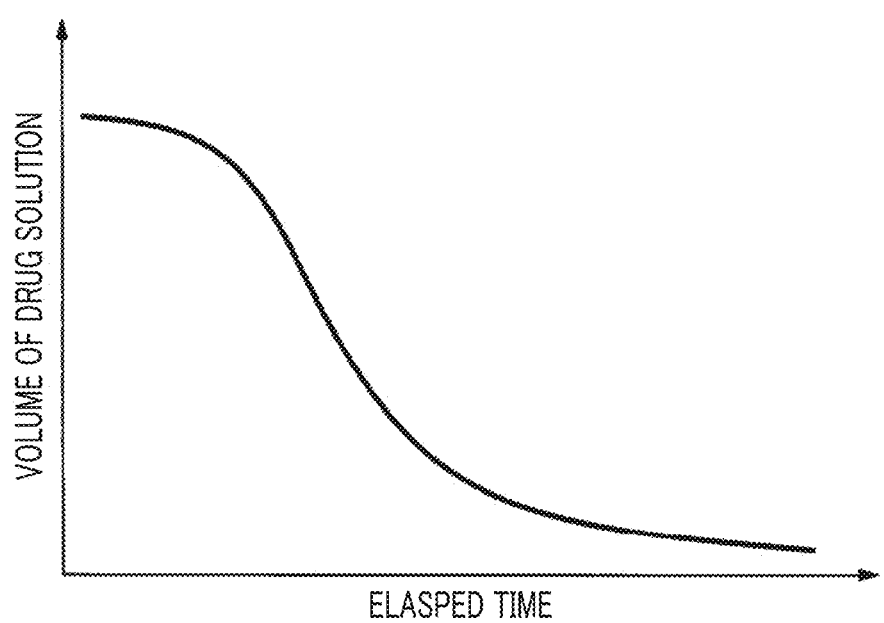
FIG. 39 is a graph showing a relationship between the volume of a drug solution that fills a needle-shaped recess and an elapsed time immediately after the filling.

FIG. 39 is a graph showing a relationship between the volume of the drug solution 24 that fills the needle-shaped recess 14 and an elapsed time after the filling. As shown in FIG. 21, the volume of the drug solution 24 in the needle-shaped recess 14 is reduced with the lapse of time due to evaporation of water included in the drug solution 24 as shown in the above-described FIGS. 8A to 8D. On the other hand, the amount of the drug 26 included in the drug solution 24 in the needle-shaped recess 14 is not changed. Thus, the concentration of the drug solution 26 in the drug solution 24 increases with the lapse of time. Accordingly, by calculating a temporal change of the volume of the drug solution 24 in the needle-shaped recess 14 as shown in FIG. 39, it is possible to calculate a temporal change of the concentration of the drug 26 in the drug solution 24 in the needle-shaped recess 14.

By storing the temporal change of the concentration of the drug 26 in a storage unit (not shown), the volume calculation unit 290 can calculate the concentration of the drug 26 in the drug solution 24 in the needle-shaped recess 14 in the measurement of the volume of the above-described drug solution 24. Thus, the volume calculation unit 290 can calculate the amount of the drug 26 for each needle-shaped recess 14 on the basis of the concentration of the drug 26 in the drug solution 24 and the measurement result of the volume of the drug solution 24 for each needle-shaped recess 14. The calculation result of the amount of the drug 26 is also stored in the storage unit (not shown) as the measurement result of the amount of the drug 26 for each needle-shaped recess 14 of the mold 12.

Figure 40:
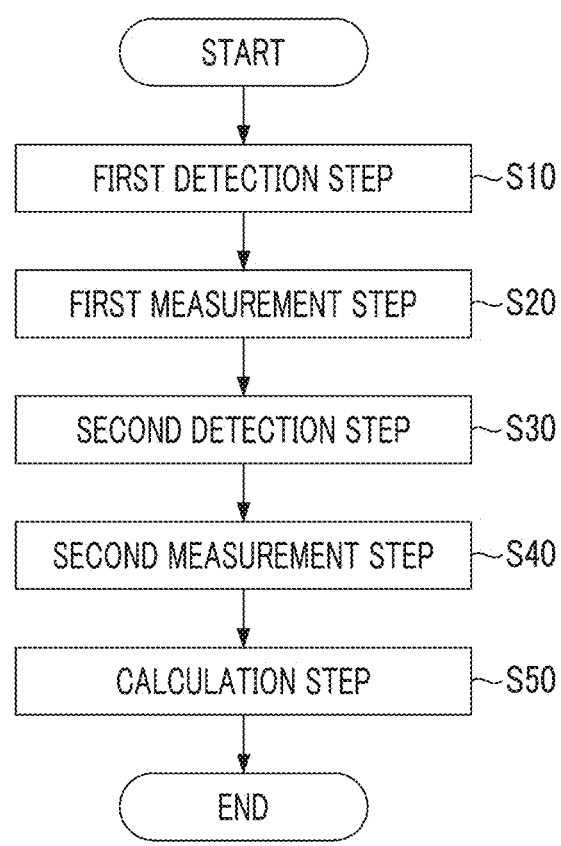
FIG. 40 is a flowchart showing a procedure of a measurement method.

A measurement method of this embodiment will be briefly described. FIG. 40 is a flowchart showing a procedure of the measurement method. The measurement method includes a first detection step (step S10) of detecting position information on a needle-shaped recess of a mold in a state where a first needle-shaped recess is not filled with a drug solution, a first measurement step (step S20) of measuring the shape of the needle-shaped recess on the basis of a detection result in the first detection step (step S10), a second detection step (step S30) of detecting position information on a surface of the drug solution that fills the needle-shaped recess or a dried drug after the filling, a second measurement step (step S40) of measuring the shape of the drug solution or the drug on the basis of the detection result based on the second detection step (step S30), and a calculation step (step S50) of calculating the volume of the drug solution that fills the needle-shaped recess or the dried drug after the filling on the basis of the shape of the needle-shaped recess measured in the first measurement step (step S20) and the shape of the drug solution or the drug measured in the second measurement step (step S40).

[Others]

Further, the shape of an MNA (that is, the shape of a needle-shaped recess formed in a mold) is not limited to a conical shape, and for example, may be a polygonal pyramid shape such as a quadrangular pyramid. Further, it is preferable to perform surface treatment for enhancing a hydrophilic property on the surface of the mold. According to this configuration, a contact angle of the drug solution that fills the needle-shaped recess is reduced, and thus, it is possible to form the surface of the drug solution to be close to horizontal.

In addition, in order to enhance an optical feature of a drug solution according to each embodiment, it is preferable to add a pigment (for example, Evans' Blue) harmless to a human body to the drug solution.

Further, in a case where the shape of the drug solution is measured, it is preferable to measure positions of a plurality of measurement points under an environment that the humidity is 100% so that the drug solution is not naturally dried, or in a state where an upper side of the mold that is filled with the drug solution is covered by a transparent cover.

Furthermore, the respective functional configurations of the above-described measurement system may be appropriately realized by arbitrary hardware, software, or a combination thereof. For example, the invention may also be applied to a measurement program that causes a computer to execute measurement methods (measurement processing procedures) in the above-described respective devices and processing units (the first detection unit 101, the first measurement unit 102, the detection unit 103, the second measurement unit 104, and the calculation unit 105), a computer-readable recording medium (non-transitory tangible medium) on which the measurement program is recorded, or a computer in which the measurement program can be installed.

Further, it is preferable that the measurement results measured by the measurement systems in the embodiments are fed back to the MNA sheet manufacturing process.

For example, in a case where a total volume of the drug solution 24 is smaller than a target value (or a lower limit value in a target range), a method for decreasing the speed of the nozzles 20 and 30 or increasing the amount of the drug solution 24 to be supplied to the mold 12 may be considered, and in a case where the total volume of the drug solution 24 is larger than the target value (or an upper limit value in the target range), a method for increasing the speed of the nozzles 20 and 30 or decreasing the amount of the drug solution 24 to be supplied to the mold 12.

EXPLANATION OF REFERENCES

10: MNA sheet
10A: MNA patch

12: mold
12A: first surface
12B: second surface
14: needle-shaped recess
16: communication hole
18: gas transmission sheet
20: nozzle
22: discharge port
24: drug solution
24A: surface
26: drug
28: support
30: nozzle
32: discharge port
34: base solution
36: base
100: measurement system
101: first detection unit
102: first measurement unit
103: second detection unit
104: second measurement unit
105: calculation unit
110: confocal microscope
112: base
114: table
116: table movement unit
118: table tilt unit
120: light source
122: measurement unit main body
123: surface position detection unit
124: Z-axis movement unit
125: measurement unit
132: computer
134Z: Z-axial direction position detection unit
136: volume calculation unit
144: beam splitter
147: pinhole plate
148: objective lens
150: photodetector
200: measurement apparatus
210: light source
220: interference filter
230: lens
240: photodetector
250: imaging unit
260: computer
270: surface position detection unit
280: measurement unit
290: volume calculation unit
300: transmitted light beam pattern image
310: shading image
320: dark image
330: bright image
340: gray image
420: surface feature line
500: measurement apparatus
500A: imaging unit
500B: apparatus main body
510: XYZ stage
520: light source
560: computer
562: light source
530: wavelength selection filter
540: imaging optical system
550: photodetector
560: computer
562: surface position detection unit
564: image analysis unit
566: measurement unit
568: distance measurement unit
570: volume calculation unit

What is claimed is:

1. A measurement system that measures an amount of a drug solution that fills each needle-shaped recess of a mold in which a plurality of needle-shaped recesses are formed and which includes a first surface and a second surface, the needle-shaped recess being an inverted type of a microneedle, or an amount of a drug after the filled drug solution is dried, the system comprising:
   a first detection unit that detects position information regarding each needle-shaped recess of the mold in a state where the drug solution does not fill the needle-shaped recess;
   a first measurement unit that measures a shape of the needle-shaped recess based on a detection result of the first detection unit;
   a second detection unit that detects position information regarding a surface of the drug solution that fills the needle-shaped recess or the drug after the filled drug solution is dried;
   a second measurement unit that measures a shape of the surface of the drug solution or the drug based on a detection result of the second detection unit; and
   a calculation unit that calculates a volume of the drug solution that fills the needle-shaped recess or the drug after the filled drug solution is dried based on the shape of the needle-shaped recess measured by the first measurement unit and the shape of the surface of the drug solution or the drug measured by the second measurement unit.

2. The measurement system according to claim 1, wherein the first detection unit is a confocal microscope that includes at least a confocal optical system and a photodetector.

3. The measurement system according to claim 1, wherein the first detection unit includes at least a triangulation type displacement meter.

4. The measurement system according to claim 1, wherein the second detection unit is a confocal microscope that includes a confocal optical system and a photodetector.

5. The measurement system according to claim 1, wherein the second detection unit includes at least a triangulation type displacement meter.

6. The measurement system according to claim 1, wherein the second detection unit includes a light source that allows parallel light beams to be vertically incident to the first surface of the mold on a side where the drug solution is filled, and a photodetector that images transmitted light beams of the parallel light beams emitted from the second surface on a side opposite to the first surface, and
wherein the transmitted light beams include a first transmitted light beam that goes straight inside the mold and is output from a first region of the second surface, a second transmitted light beam that is incident to a first wall surface portion in the mold, is refracted by the first wall surface portion, and is output from a second region, corresponding to the needle-shaped recess, of the second surface, and a third transmitted light beam that is incident to a second wall surface in the mold, is refracted by the second wall surface portion at a refractive angle larger than that of the first transmitted light beam, and is output from a part of the first region.

7. The measurement system according to claim 1,
wherein the second detection unit includes a light source that allows parallel light beams having a first wavelength band and a second wavelength band to be vertically incident to the second surface, a photodetector that images a first transmitted light beam of the first wavelength band and a second transmitted light beam of the second wavelength band output from the first surface on a side opposite to the second surface, and an image analysis unit that analyzes images of the first transmitted light beam and the second transmitted light beam, and wherein the second measurement unit includes a distance measurement unit that measures a distance at each position in the surface of the drug solution based on a detection result of the image analysis unit.

8. A measurement method for measuring an amount of a drug solution that fills each needle-shaped recess of a mold in which a plurality of needle-shaped recesses are formed, the needle-shaped recess being an inverted type of a microneedle, or an amount of a drug after the filled drug solution is dried, the method comprising:
  a first detection step of detecting position information regarding each needle-shaped recess of the mold in a state where the drug solution does not fill the needle-shaped recess;
  a first measurement step of measuring a shape of the needle-shaped recess based on a detection result in the first detection step;
  a second detection step of detecting position information regarding a surface of the drug solution that fills the needle-shaped recess or the drug after the filled drug solution is dried;
  a second measurement step of measuring a shape of the surface of the drug solution or the drug based on a detection result in the second detection step; and
  a calculation step of calculating a volume of the drug solution that fills the needle-shaped recess or the drug after the filled drug solution is dried based on the shape of the needle-shaped recess measured in the first measurement step and the shape of the surface of the drug solution or the drug measured in the second measurement step.

9. A computer-readable non-transitory tangible recording medium which records a program for causing a computer to execute a method for measuring an amount of a drug solution that fills each needle-shaped recess of a mold in which a plurality of needle-shaped recesses are formed, the needle-shaped recess being an inverted type of a microneedle, or an amount of a drug after the filled drug solution is dried, the program causing a computer to execute:
  a first detection step of detecting position information regarding each needle-shaped recess of the mold in a state where the drug solution does not fill the needle-shaped recess;
  a first measurement step of measuring a shape of the needle-shaped recess based on a detection result in the first detection step;
  a second detection step of detecting position information regarding a surface of the drug solution that fills the needle-shaped recess or the drug after the filled drug solution is dried;
  a second measurement step of measuring a shape of the surface of the drug solution or the drug based on a detection result in the second detection step; and
  a calculation step of calculating a volume of the drug solution that fills the needle-shaped recess or the drug after the filled drug solution is dried based on the shape of the needle-shaped recess measured in the first measurement step and the shape of the surface of the drug solution or the drug measured in the second measurement step.

* * * * *